(12) United States Patent
Knipe et al.

US009937256B2

(10) Patent No.: US 9,937,256 B2
(45) Date of Patent: Apr. 10, 2018

(54) HYDROGELS FOR DELIVERY OF THERAPEUTIC COMPOUNDS

(71) Applicant: Board of Regents, the University of Texas System, Austin, TX (US)

(72) Inventors: Jennifer M. Knipe, Austin, TX (US); Laura E. Strong, Austin, TX (US); Nicholas A. Peppas, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/994,704

(22) Filed: Jan. 13, 2016

(65) Prior Publication Data

US 2016/0206741 A1 Jul. 21, 2016

Related U.S. Application Data

(60) Provisional application No. 62/103,446, filed on Jan. 14, 2015.

(51) Int. Cl.

| | | |
|---|---|---|
| A61K 47/32 | (2006.01) | |
| A61K 38/06 | (2006.01) | |
| A61K 38/08 | (2006.01) | |
| A61K 38/10 | (2006.01) | |
| A61K 38/16 | (2006.01) | |
| A61K 9/50 | (2006.01) | |
| A61K 38/28 | (2006.01) | |
| C08L 33/02 | (2006.01) | |
| C08L 39/06 | (2006.01) | |
| C12N 15/113 | (2010.01) | |
| A61K 9/16 | (2006.01) | |
| A61K 9/51 | (2006.01) | |
| C12N 15/11 | (2006.01) | |

(52) U.S. Cl.
CPC ............ *A61K 47/32* (2013.01); *A61K 9/1635* (2013.01); *A61K 9/5026* (2013.01); *A61K 9/5138* (2013.01); *A61K 38/06* (2013.01); *A61K 38/08* (2013.01); *A61K 38/10* (2013.01); *A61K 38/16* (2013.01); *A61K 38/28* (2013.01); *C08L 33/02* (2013.01); *C08L 39/06* (2013.01); *C12N 15/111* (2013.01); *C12N 15/113* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| | | |
|---|---|---|
| 2007/0190084 A1 | 8/2007 | Hilt et al. |
| 2010/0197041 A1* | 8/2010 | Hermann ............ C12Q 1/6818 436/501 |
| 2012/0040397 A1 | 2/2012 | Luo et al. |

FOREIGN PATENT DOCUMENTS

| | | |
|---|---|---|
| WO | WO 2008/055254 | 5/2008 |
| WO | WO 2012/109068 | 8/2012 |

OTHER PUBLICATIONS

Carr et al. "Assessment of poly(methacrylic acid-co-N-vinyl pyrrolidone) as a carrier for the oral delivery of therapeutic proteins using Caco-2 and HT29-MTX cell lines", Journal of Biomedical Materials Research Part A, 2010; 504-512.*
Ulbrich et al. "Polymers Containing Enzymatically Degradable Bonds, 3a) by Oligopeptide Sequences Cleavable by Trypsin", Makromol. Chem., 1981; 1917-1928.*
Knipe et al. "Multiresponsive Polyanionic Microgels with Inverse pH Responsive Behavior by Encapsulation of Polycationic Nanogels", Journal of Applied Polymer Science, 2014; 40098 (1-8); first published Nov. 6, 2013.*
Forbes et al., "Oral delivery of small RNA and DNA", Journal of Controlled Release, 2012; 438-445.*
Lee et al. ,"Proteolytically Degradable Hydrogels with a Fluorogenic Substrate for Studies of Cellular Proteolytic Activity and Migration", Biotechnol. Prog., 2005, 1736-1741 (Year: 2005).*
Aouadi et al., "Orally delivered siRNA targeting macrophage map4k4 suppresses systemic inflammation", Nature,. 458(7242): 1180-1184, 2009.
Bhavsar and Amiji, "Development of novel biodegradable polymeric nanoparticles-in-microsphere formulation for local plasmid DNA delivery in the gastrointestinal tract", AAPS PharmSciTech, 9(1): 288-294, 2008.
Bhavsar et al., "Formulation optimization for the nanoparticles-in-microsphere hybrid oral delivery system using factorial design", J Controlled Release, 110(2): 422-430, 2006.
Bouchie, "Companies in footrace to deliver RNAi", Nat Biotechnol, 30(12): 1154-1157, 2012.
Fattal and Bochot, "State of the art and perspectives for the delivery of antisense oligonucleotides and siRNA by polymeric nanocarriers", Int. J. Pharm., 364(2): 237-248, 2008.
Glangchai et al., "Nanoimprint lithography based fabrication of shape-specific, enzymatically-triggered smart nanoparticles", J Controlled Release,. 125(3): 263-272, 2008.
Guo et al., "Cholinesterase-responsive supramolecular vesicle", J Am Chem Soc, 134(24): 10244-10250, 2012.
International Search Report and Written Opinion issued in International Application No. PCT/US2016/013222, dated May 6, 2016.
Kim and Rossi, "Strategies for silencing human disease using RNA interference", Nature Reviews Genetics, 8(3): 173-184, 2007.
Knipe et al., "Enzymatic biodegration of hydrogels for protein delivery targeted to the small intestine", Biomacromolecules, 16: 962-972, 2015.
Knipe et al., "Enzyme- and pH-responsive microencapsulated nanogels for oral delivery of siRNA to induce TNF-α knockdown in the intestine", Biomacromolecules, 17: 788-797, 2016.

(Continued)

*Primary Examiner* — Lianko G Garyu
(74) *Attorney, Agent, or Firm* — Parker Highlander PLLC

(57) ABSTRACT

In some aspects, methacrylate co-polymers crosslinked with an enzymatically cleavable peptide linker are provided and may be used for the oral delivery of a therapeutic. The peptide linker may be cleavable by an enzyme in the small intestine and may allow for the delivery of a therapeutic protein or nucleic acid to the small intestine. Also provided are methods of using the polymers for the treatment of a disease.

22 Claims, 31 Drawing Sheets

(56) References Cited

OTHER PUBLICATIONS

Laroui et al., "Functional tnfα gene silencing mediated by polyethyleneimine/tnfα sirna nanocomplexes in inflamed colon", *Biomaterials*, 32(4): 1218-1228, 2011.
Olsen et al., "Trypsin cleaves exclusively c-terminal to arginine and lysine residues", *Mol Cell Proteomics*, 3: 608-14, 2004.
Schiffelers et al., "Pharmaceutical prospects for RNA interference", *Pharm Res*, 21: 1-7, 2003.
Strong et al., "pH responsive nanoparticles-in-microparticles system for oral delivery of siRNA", *Biomaterials 2015 Annual Meeting*, Program Abstracts, 2015.
Subr et al., "Release of macromolecules from hydrophlilic gels containing enzymatically degradable bonds", *J. Biomater. Sci. Polymer Edn*, 1: 261-278, 1990.
Thornton et al., "Enzyme-responsive polymer hydrogel particles for controlled release ", *Adv Mater*, 19(9): 1252-1256, 2007.
Ulbrich et al., "Polymers containing enzymatically degradable bonds Vi. Hydrophilic gels cleavable by chymotrypsin", *Biomaterials*, 3: 150-154, 1982.
Vlieghe et al., "Synthetic therapeutic peptides: Science and market", *Drug Discovery Today*, 15(1-2): 40-56, 2010.
Wanakule et al., "Nano-inside-micro: Disease-responsive microgels with encapsulated nanoparticles for intracellular drug delivery to the deep lung", *J Controlled Release*, 162: 429-437, 2012.
Whitehead et al., "Knocking down barriers: Advances in siRNA delivery", *Nat. Rev. Drug Discovery*, 8(2): p. 129-138, 2009.
Wilson et al., "Orally delivered thioketal nanoparticles loaded with tnf-alpha-sirna target inflammation and inhibit gene expression in the intestines", *Nat Mater*, 9: 923-928, 2010.

\* cited by examiner

HYDROGELS FOR DELIVERY OF THERAPEUTIC COMPOUNDS

CROSS-REFERENCE TO RELATED APPLICATIONS

This application claims the benefit of U.S. Provisional Patent Application No. 62/103,446, filed Jan. 14, 2015, the entirety of which is incorporated herein by reference.

STATEMENT OF GOVERNMENT SUPPORT

The invention was made with government support under Grant No. CBET1033746 and DGE1110007 awarded by the National Science Foundation. The government has certain rights in the invention.

INCORPORATION OF SEQUENCE LISTING

The sequence listing that is contained in the file named "UTSBP1052US_ST25.txt", which is 10 KB (as measured in Microsoft Windows®) and was created on Jan. 7, 2016, is filed herewith by electronic submission and is incorporated by reference herein.

BACKGROUND OF THE INVENTION

1. Field of the Invention

The present invention relates generally to the field of polymer chemistry and drug delivery. More particularly, it concerns hydrogel polymers that may be used for the oral delivery of therapeutic compounds.

2. Description of Related Art

Environmentally-responsive hydrogels, or hydrophilic, crosslinked polymer networks that undergo physicochemical changes in response to one or more environmental stimuli, offer the specificity of highly tunable materials combined with excellent biocompatibility (Peppas et al., 2006; Hoffman, 1991; Qiu and Park, 2001; Caldorera-Moore and Peppas, 2009). As the next generation of biomaterials, these "intelligent" networks are able to respond to or mimic biological environments and processes such as vascularization (Bae et al., 2012; Phelps et al., 2009), tumor physiology (Lin et al., 2013; Liechty et al., 2012), endosomal compartments (Wong et al., 2014; Forbes and Peppas, 2014; Liang et al., 2014), or the extracellular matrix (Guvendiren et al., 2013; Kirschner et al., 2013). This capability could be instrumental in achieving various biomedical advances, including tissue regeneration and controlled delivery of biological therapeutics (Knipe et al., 2014a; Holzapfel et al., 2013).

Some hydrogels with pH-responsive behavior may be used as hydrogel systems for drug delivery applications (Peppas et al., 2000). Polyanionic hydrogels such as poly(methacrylic acid) (PMAA) exhibit complexation via hydrogen bonding at low pH conditions, such as that of gastric fluid, and undergo increased swelling due to ionization of the carboxylic groups at neutral pH conditions, such as that of the intestine (Kost et al., 2012). Thus, PMAA copolymers have been utilized as oral drug delivery carriers or coatings for their ability to protect a loaded therapeutic from denaturation and enzymatic degradation as it travels through gastric conditions yet swell and release the therapeutic at the site of absorption in the small intestine (Torres-Lugo et al., 2002; Torres Lugo et al., 1999; Knipe et al., 2014; Lowman et al., 1999; Carr et al., 2009; Carr and Peppas., 2010).

Biodegradation is another possible environmental response of hydrogels designed for drug delivery applications (Knipe et al., 2014; Hu et al., 2012). Polymers that degrade by hydrolysis, such as polyanhydrides (Torres et al., 2007; Lopac et al., 2009), poly(orthoesters) (Hoffman, 1991; Thombre et al., 1985), poly(caprolactone), and poly(lactic acid) and poly(glycolic acid) (Lao et al., 2008; Anderson et al., 2012) have been used for drug delivery.

Oral delivery of siRNA might be used for treating diseases of the gastrointestinal (GI) tract, such as inflammatory bowel diseases, and intestinal absorption could offer a route to systemic delivery. However, there are many extracellular and intracellular barriers to oral siRNA delivery such as proteolytic degradation (Fattal et al., 2008), harsh pH environments (Bouchie et al., 2012), and the necessity to achieve intracellular delivery and endosomal escape while maintaining the integrity of the siRNA (Whitehead et al., 2009; Schiffelers et al., 2003), making successful oral delivery of siRNA a daunting task. The current strategies for oral delivery of siRNA to the intestine are relatively few in number, and they employ approaches that are only effective in a limited capacity. Clearly there exists a need for improved methods for oral delivery of therapeutic nucleotides Despite improvements in oral delivery of therapeutic proteins using hydrogel polymers, there nonetheless exists a significant need for improved control over release of the therapeutic in the small intestine from the hydrogel. Additionally, there remains a need for hydrogel polymers that are optimized for delivery of particular therapeutics.

SUMMARY OF THE INVENTION

In some aspects, the present invention overcomes limitations in the prior art by providing pH-sensitive polymers that may be used for the improved oral delivery of therapeutic compounds such as, e.g., therapeutic proteins or nucleotides. In some embodiments, the polymer is crosslinked with a peptide that is cleavable by an enzyme present in the small intestine of a mammal or human such as, e.g., trypsin. In some embodiments, it has been observed that crosslinking with an enzyme-cleavable peptide linker can result in significant improvements in the release of a therapeutic from the pH-sensitive polymer in the small intestine. In some aspects, pH-sensitive polymers that may be used for the oral delivery of a nucleotide or modified nucleotide therapeutic such as, e.g., a siRNA or a miRNA, are also provided. In some embodiments, the pH-sensitive polymer may contain the therapeutic nucleotide in a polycationic nanoparticle such as, e.g., poly(2-(diethylaminoethyl) methacrylate) (PDEAEMA).

As shown in the below examples, poly(methacrylic acid-co-N-vinylpyrrolidone) (P(MAA-co-NVP)) polymer chains were used to impart hydrophilic and pH-responsive behavior that controlled diffusion of enzymes into the polymer network due to pH-responsive complexation. The polymer chains were crosslinked by a facile bioconjugation reaction with an oligopeptide rich in arginine and lysine groups targeted for degradation specifically by the enzyme trypsin. Data regarding the synthesis, degradation, cytocompatibility, and therapeutic loading and release using the pH-responsive P(MAA-co-NVP) crosslinked by the biodegradable peptide are provided.

An aspect of the present invention relates to a hydrogel polymer, wherein the polymer comprises a P(MAA-co-NVP) copolymer that is crosslinked with an enzymatically cleavable peptide linker, wherein the peptide linker is 3-25 amino acid residues in length and contains at least one lysine amino acid. The peptide linker may be cleavable by a serine protease (e.g., a trypsin, chymotrypsin, or elastase), carboxypeptidase, or aminopeptidase. In some embodiments, the peptide linker is cleavable by trypsin, wherein the trypsin is trypsin 1, trypsin 2, or mesotrypsin. In some embodiments, the peptide is 4-20, 5-15, or 5-10 amino acid residues in length. The peptide may comprise or consists of GRRRGK (SEQ ID NO: 1). The peptide may comprises the structure:

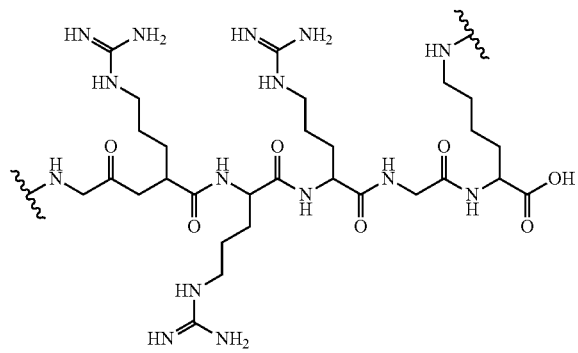 [SMILES: *NCCCCC(NC(=O)CNC(=O)C(CCCNC(=N)N)NC(=O)C(CCCNC(=N)N)NC(=O)C(CCCNC(=N)N)CC(=O)CN*)C(=O)O]

In some embodiments, the polymer comprises the structure:

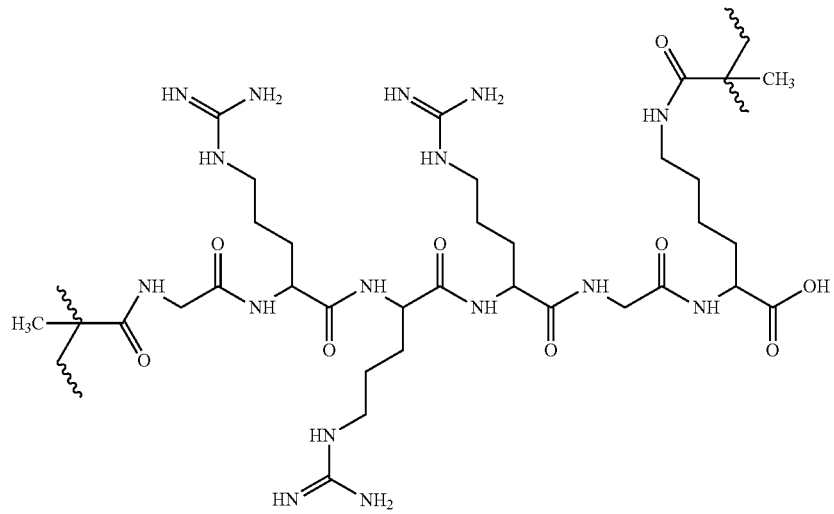

In some embodiments, the polymer has been crosslinked with the peptide through the use of a coupling reagent. The coupling reagent may be a carbodiimide. In some embodiments, the polymer has been crosslinked with the peptide via an EDC-NHS reaction.

The polymer may comprise a polycationic nanoparticle. The polycationic nanoparticle may be substantially encapsulated within the polymer. In some embodiments, the polycationic nanoparticle comprises or consists of poly(2-methoxy ethyl acrylate) (PMEA), poly(2-(diethylaminoethyl) methacrylate) (PDEAEMA), chitosan, poly(ethyleneimine) (PEI), poly(amidoamine) (PAMAM), poly(dimethylaminopropyl methacrylate) (PDMAPMA), poly(2-aminoethyl methacrylate) (PAEMA), or poly(2-(dimethylaminoethyl) methacrylate) (PDMAEMA).

The polymer may comprise a therapeutic protein such as, e.g., insulin. In some embodiments, the polymer comprises a therapeutic nucleic acid or polynucleotide. The nucleic acid may be a small interfering RNA (siRNA), a micro RNA (miRNA), a short hairpin RNA (shRNA), or an antisense oligonucleotide. In some embodiments, the nucleic acid comprises at least one modified nucleic acid. In some embodiments, the modified nucleic acid is a locked nucleic acid (LNA). Alternately, the nucleic acid may consist of non-modified or naturally occurring nucleotides. In some embodiments, the modified nucleic acid is a locked nucleic acid (LNA). In some embodiments, the therapeutic nucleic acid is comprised within or associated with the polycationic nanoparticle, wherein at least part of the polymer forms a coating around at least part of the polycationic nanoparticle. The polymer may be comprised in a pharmaceutical composition. In some embodiments, the pharmaceutical composition is formulated for oral delivery (e.g., as a tablet, capsule, or liquid preparation). In some embodiments, the nucleic acid (e.g., siRNA, miRNA, shRNA) is loaded or embedded in the polymer by a method comprising incubating the nucleic acid in a loading solution (e.g., containing about 0.25 μM to about 4 μM of the nucleic acid in nuclease-free or essentially nuclease-free PBS at about pH 5.5), and the incubating may be for a period of time sufficient to allow the nucleic acid to enter the polymer. In some embodiments, the nucleic acid is loaded into the copolymer before or during crosslinking with the peptide linker. As shown in the below examples, loading the nucleic acid into the copolymer prior to crosslinking resulted in improved synthesis of the hydrogels and improved loading of the nucleic acid in the polymer, and these methods were also observed to achieve gene knockdown in cells in experiments where the nucleic acid was a siRNA.

Another aspect of the present invention relates to a method for loading a nucleic acid into a crosslinked hydrogel polymer, comprising: (i) incubating a copolymer comprising an acrylic acid, an acrylate monomer, or methacrylic acid in a loading solution comprising the nucleic acid; and subsequently (ii) crosslinking the copolymer with a crosslinker. In some embodiments, the crosslinker is an enzymatically cleavable peptide crosslinker. In some embodiments, the copolymer comprises methacrylic acid and N-vinylpyrrolidone. The nucleic acid may be a siRNA, an miRNA, or an shRNA. In some embodiments, the copolymer is a P(MAA-co-NVP) copolymer; and wherein the linker is an enzymatically cleavable peptide linker, wherein the peptide linker is 3-25 amino acid residues in length and contains at least one lysine amino acid. The crosslinked hydrogel polymer may be a hydrogel polymer of the present invention or as described above.

Another aspect of the present invention relates to a method of treating a disease comprising administering a pharmacologically relevant amount of a polymer of the present invention to a mammalian subject in need of such treatment. In some embodiments, said administration is oral. The subject may be a human. In some embodiments, the disease is inflammatory bowel disease, Crohn's disease, diabetes, a complication from diabetes, or celiac disease.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) scale bar=10 µm; (FIG. 1B) scale bar=5 µm (HV=15.00 kV, WD=9.6 mm).

FIG. 4B) SIF (scale=10 µm); FIG. 4C) PBS (scale=10 µm); FIG. 4D) SGF (scale=5 µm); FIG. 4E) SIF (scale=5 µm); FIG. 4F) PBS (scale=5 µm); (EHT=5.00 kV, WD=15.6 mm). Following incubation, microgels were lyophilized and dusted onto a carbon-tape coated aluminum stub, then coated with 5 nm Pt/Pd.

(FIG. 9B) 70° C. or 80° C. (degradation at 37° C., pH 7.4, N=3). Incubation at either 70° C. or 80° C. was sufficient to deactivate trypsin.

(FIG. 10A) Murine fibroblast L929 and (FIG. 10B) murine macrophage RAW 264.7 cells were incubated with degraded microgel solutions ranging from 0.43-2 mg/mL in culture media for 8 h. Following removal of the microgel solutions, the MTS assay was allowed to incubate for 90 min. Cell proliferation is relative to the positive control (N=3). Negative control (bleach) (■), positive control (culture media) (□), microgels (※), microgels with trypsin (※).

FIG. 12A, Nanogels labeled with NBD-Cl (green); FIG. 12B, P(MAA-co-NVP) microgel matrix labeled with TAMRA-cadaverine (red); FIG. 12C, green and red overlay showed nanogel distribution in microgel; FIG. 12D, bright field image of microgel. (Scale bar=30 µm).

FIG. 15A, 1.2 mg/ml trypsin; FIG. 15B, 0.6 mg/ml trypsin in PBS (37° C., pH 7.4, N=3). Initial decrease in relative turbidity was fitted with a linear fit ($R^2$>0.98).

FIG. 17B, 0.6 mg/ml trypsin incubated with various concentrations of P(MAA-co-NVP) microgels containing degradable crosslinks for 90 minutes, and then deactivated by 5 minutes incubation at 70° C. or addition of 2× volume of DMEM (degradation at 37° C., pH 7.4, N=3).

FIG. 26B) 1 mg/ml in DMEM; or FIG. 26C) 0.4 mg/ml in OptiMEM for 18 hours. Following microgel incubation, the MTS assay was allowed to incubate for 90 min. Absorbance at 490 nm is relative to the positive control (culture media only, patterned bar) (N=3).

FIG. 27B) 1 mg/ml in DMEM; or FIG. 27C) 0.4 mg/ml in OptiMEM for 18 hours. Following microgel incubation, the LDH assay was used to evaluate cell viability (N=3).

(FIG. 30A), PAGE evaluation of siRNA degradation after 1) siRNA-loaded microgels; 2) siRNA and nanogels; 3) microgels with nanogels and siRNA; and 4) microgels with nanogels and siRNA were incubated with 0.6 mg/ml trypsin for 90 minutes; after 5) siRNA-loaded microgels; 6) siRNA and nanogels; 7) microgels with nanogels and siRNA; and 8) microgels with nanogels and siRNA were incubated with 0.6 mg/ml trypsin for 90 minutes followed by 15 minutes incubation with heparin; and 9-10) incubation of siRNA with different concentrations RNase. (FIG. 30B), PAGE evaluation of siRNA degradation after 1) siRNA on ice; 2) siRNA at room temperature; 3) siRNA in pH 5.5 PBS; 4) siRNA in pH 8.5 PBS; 5) siRNA loaded with microgels; 6) siRNA in 1.2 mg/ml trypsin; 7) siRNA in 0.6 mg/ml trypsin; 8) siRNA and microgels in 1.2 mg/ml trypsin; 9) siRNA and microgels in 0.6 mg/ml trypsin.

FIG. 33B) fluorescently-tagged nanogels with fluorescently tagged siRNA; and FIG. 33C) fluorescently-tagged degraded microgels containing fluorescently-tagged nanogels and fluorescently-tagged siRNA (Scale bar=10 μm).

FIG. 35A, Hydrodynamic diameter of nanogels at pH 5.5 (~122 nm) and pH 7.4 (~110 nm). The nanogels display pH-responsive behavior in which they swell under pH conditions seen in the endosome (n=3, Student's t-test, *p≤0.001). FIG. 35B, Zeta potential measurements indicate a positive surface charge of ~19 mV, which decreases slightly after loading with negatively charged RNA (n=3, Student's t-test, *p<0.01). FIG. 35C, Encapsulation and FIG. 35D, weight efficiency of siRNA loading into nanogels. Concentration of nanogels in loading solution was 0.125 mg/ml. Encapsulation efficiency was calculated by measuring the concentration of siRNA remaining in solution after particle loading ($c_f$) and expressed as ($c_0-c_f$)/$c_0$*100 (n=3).

DESCRIPTION OF ILLUSTRATIVE EMBODIMENTS

Figures 1A, 1B:
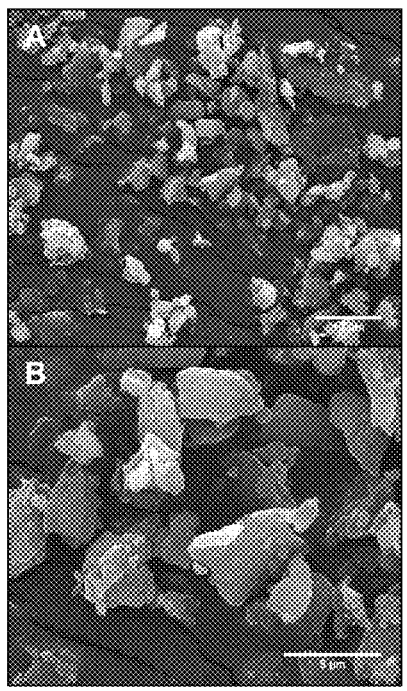
FIGS. 1A-1B: P(MAA-co-NVP) microgels with peptide crosslinks in the dry state, crushed and sieved to <30 Particles were dusted onto a carbon-tape coated aluminum stub then coated with 10 nm Pt/Pd.

In some aspects, the present invention provides a P(MAA-co-NVP) copolymer that is crosslinked with an enzymatically cleavable peptide linker. The enzymatically cleavable peptide linker may be cleaved by a protease in the small intestine such as trypsin or chymotrypsin. In some embodiments, little or no cleavage of the peptide linker occurs due to proteases present in the stomach (e.g., pepsin, etc.), but the peptide linker remains intact during passage through the stomach and is selectively enzymatically cleaved after entry into the small intestine. In some aspects, the polymers may be used to deliver a therapeutic such as protein or nucleotide to the small intestine, with significantly reduced degradation from the stomach. In some embodiments and as shown in the below examples, the polymers provided herein can result in improved release of the therapeutic (e.g., the therapeutic protein or nucleotide) in the small intestine.

I. HYDROGEL COPOLYMERS

In some aspects of the present invention, improved hydrogel polymers are provided. In some embodiments, the hydrogel polymer compositions may be used to for oral delivery of a drug, such as a therapeutic polynucleotide or protein. The therapeutic polynucleotide or protein may require at least some protection from degradation in the digestive system; for example, the therapeutic polynucleotide or protein may need protection from the acid conditions (e.g., pH ~2) found in the stomach. As shown in the below examples, hydrogel polymers are provided that may protect the drug (e.g., therapeutic polynucleotide or protein) while it is in transit through the acidic conditions in the stomach, and then the polymer can swell in the more basic conditions of the small intestine and allow for release of the drug or therapeutic protein in the small intestine. In some embodiments, the drug is a siRNA. In other embodiments, the drug is a therapeutic protein such as insulin. The polymers provided herein may be included in or used as a variety of pharmaceutical compositions, such as compositions for oral delivery, e.g., particles, tablets, capsules, caplets, gel-seals, lozenges, syrups, sprays, and other liquid dosage forms.

Generally, the hydrogels may comprise hydrophilic polymers or copolymers in the form of networks that can swell due to a high affinity for water; however, the hydrogel may be substantially insoluble due to the incorporation of chemical or physical crosslinks or other tie-points that keep the chains together and do not allow them to dissolve in water. In some embodiments, the crosslinker is an enzymatically cleavable peptide linker. Polymers or copolymer hydrogels may be responsive to pH changes. For example, in a solution with a lower pH (e.g., pH ~1-2), pH-sensitive hydrogel networks may be largely hydrated, similar to other hydrophilic copolymers; however, at higher pHs (e.g., at pH ~6-7), carboxylic acid groups present in the polymer or copolymer may deprotonate, and thus the polymer may attract more water into the polymer network. Thus, the increased absorption of water into the polymer or copolymer may result in swelling, thus increasing the distance between the copolymer chains. This increase in size, or swelling, can allow increased release of a drug or therapeutic nucleotide or protein from the hydrogel network. The hydrogels may thus be used to orally deliver a therapeutic nucleotide or protein to a mammalian subject such as a human (e.g., such that the therapeutic nucleotide or therapeutic protein is substantially protected from acidic conditions, denaturation, or degradation in the stomach, and then is released in the small intestine).

In some embodiments, the copolymer comprises a polymer of only the monomers referred to in the copolymer name; for example, the P(MAA-co-NVP) copolymer may be composed of a polymer made from only methacrylic acid (MAA) and N-vinylpyrrolidone (NVP). Nonetheless, as would be recognized by one of skill in the art, other monomers such as, e.g., an acrylic acid monomer may be included in the copolymer, without substantially altering one or more of the properties (e.g., loading and release of a therapeutic polynucleotide or protein, etc.) of the copolymer. As used herein, the term "copolymer" refers to a polymer that comprises at least about 75%, more preferably at least about 80%, more preferably at least about 85%, more preferably at least about 90%, or at least about 91, 92, 93, 94, 95, 96, 97, 98, 99, or 99.5% of the monomers stated in the name of the copolymer (e.g., methacrylic acid and N-vinylpyrrolidone monomers in P(MAA-co-NVP). Additional monomers that may be included in a copolymer include:

(i) acrylic acid or acrylate monomers such as, e.g., acrylic acid, itaconic acid (IA), ethacrylic acid, propacrylic acid, crotonic acid ((E)-but-2-enoic acid), methacrylate (2-methylprop-2-enoate), methyl methacrylate, (Z)-3-cyclohexylbut-2-enoic acid, butylmethacrylate (butyl 2-methylprop-2-enoate), (ii) N-vinylpyrrolidone (1-Ethenyl-2-pyrrolidone or 1-ethenylpyrrolidin-2-one, NVP), isobetadyne (1-ethenylpyrrolidin-2-one; molecular iodine); N-vinyl succinimide (1-ethenylpyrrolidine-2,5-dione), 1-ethenylpyrrolidin-2-one, trimethyl-[3-(2-methylprop-2-enoylamino)propyl]azanium; chloride), P(VA-co-NVP) (ethenol; 1-ethenylpyrrolidin-2-one), and/or (iii) poly(ethylene glycol) (P(EG) or PEG), poly(ethylene glycol) methyl ether monomethacrylate (PEGMMA), and/or poly(ethylene glycol) methacrylate (PEGMA).

In some aspects of the present disclosure, the hydrogel polymers or copolymers are partially crosslinked. In some embodiments, the polymer or copolymer hydrogels may be from about 5-75% weight percent crosslinker. In some embodiments, the polymer or hydrogel may be from about 10-75%, 20-65%, 30-55%, 40-50%, 25%, 30%, 35%, 40%, 45%, 50%, 55%, 60%, 65%, or any range derivable therein, weight percent crosslinker. In some embodiments, copolymers comprising a range of crosslinking (e.g., at least 10% weight percent, more preferably at least 25% weight percent, or about 30-50% crosslinking, etc.) may display advantageous properties (e.g., improved adsorption and release of a therapeutic protein, nanoparticle, or nucleotide in solutions of differing pH, etc.). A variety of crosslinkers are known and may be used in hydrogel polymers or copolymers of the present invention. In one particular embodiment, the crosslinker is an enzymatically cleavable peptide.

The ratio of monomers present in a copolymer may vary. For example, when two monomers comprise the majority of a copolymer (e.g., the methacrylic acid and N-vinylpyrrolidone monomers present in a P(MAA-co-NVP) copolymer, etc.), the ratio of the monomers may vary, e.g., from about 5:1-1:5, 3:1-1:3, or about 3:1, 2:1, 1:1, 1:2, or about 1:3; or any range derivable therein (e.g., for the ratio of MAA:NVP present in a P(MAA-co-NVP) copolymer). As shown in the below examples, particularly beneficial properties were observed for P(MAA-co-NVP) copolymers that comprised a ratio of from about 2:1 to about 1:2 of MAA:NVP present in the copolymer displayed significantly improved properties (e.g., loading and release of a therapeutic protein).

Polymerization reactions to polymerize monomers may be performed using methods known to one of skill in the art such as, e.g., using UV light to promote polymerization. In some embodiments, the following reaction may be used to polymerize monomers. Polymerizations may be carried out in a 1:1 mixture of water and ethanol. The weight ratio of total monomers to solvent is from about 1:1 to about 1:10. In some embodiments, the weight ratio of total monomers to solvent is about 1:3. Within this cosolvent, monomers may be added at various molar ratios along with 1 mol % initiator with respect to monomer. In some embodiments, the initiator is a photoinitiator such as, e.g., Irgacure 184®. The monomer solution may then be introduced into a nitrogen environment and purged with nitrogen to remove oxygen, a free radical scavenger. In some embodiments, the mixture is homogenized in a flask and then polymerized, e.g., for 30 minutes in 100 mW/cm$^2$ UV light using a UV source. After the polymerization, the polymer is purified from the unreacted monomer. In some aspects, the purification includes the addition of an acid to precipitate the polymer. The polymer may be centrifuged and the resuspended in water. In some embodiments, the polymer is washed three times and then lyophilized over the course of 24 hours. In some embodiments, the polymers are crosslinked and crushed into microparticles (e.g., with a mortar and pestle), and sieved to a desired size (e.g., less than 2000 μm in size). Depending on the particular formulation, it may be desired to sieve the microparticles of dried hydrogel copolymer into a range of desired sizes, e.g., about 10-2000 μm, 25-1000 μm, 10-500 μm, 10-100 μm, 10, 20, 30, 35, 40, 45, 50, 55, 60, 65, 70, 75, 80, 85, 90, 100, 200, 300, 400, 500, 1000, 1500, 2000 μm or any range derivable therein.

In some embodiments, the hydrogel copolymers may be used as or included in a pharmaceutical composition. It is envisioned that the pharmaceutical composition may include one or more additional agent such as a starch, cellulose, or flavoring, etc. As such, these compositions may be formulated with an inert diluent or with an assimilable edible carrier, or they may be enclosed in hard- or soft-shell gelatin capsule, or they may be compressed into tablets, or they may be incorporated directly with the food of the diet. In certain embodiments, the hydrogel copolymer may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings can reduce denaturation of the composition in the stomach or upper bowel where the pH is acidic. See, e.g., U.S. Pat. No. 5,629,001. Upon reaching the small intestines, the basic pH therein can substantially or completely dissolve the coating and permits the composition to be released. A syrup may contain a hydrogel copolymer and a sweetening agent (e.g., sucrose), a preservative (e.g., methyl or propylparabens), a dye, and/or flavoring (e.g., cherry or orange flavor, etc.). Typically, any material used in preparing a dosage unit form should be substantially pharmaceutically pure and substantially non-toxic in the amounts employed.

II. ENZYMATICALLY CLEAVABLE LINKERS

In some aspects, the polymer of the present disclosure includes an enzymatically cleavable peptide as a linker. In some embodiments, the enzymatically cleavable peptide crosslinks the carboxylic acid groups of the polymer or hydrogel. A number of different protease cleavable peptides may be used as linkers for the polymer of the present disclosure. In some embodiments, the peptide comprises a protease cleavable site which is cleaved in the small intestine. In some embodiments, the protease cleavable peptide is cleaved by a protease present in the small intestine. In one preferred embodiment, the protease cleavable peptide linker is not cleaved by any proteases present in the stomach but only by a protease found in the small intestine. In some embodiments, the enzymatically cleavable peptide is a trypsin or chymotrypsin cleavable peptide. In some embodiments, the enzymatically cleavable peptide may be selectively cleavable by serine proteases, including trypsin and elastase, carboxypeptidase, or aminopeptidase. In some embodiments, the enzymatically cleavable peptide is a trypsin cleavable peptide. Without being bound by any theory, the trypsin protease may recognize a positively charged amino acid residue and cleave the peptide on the carboxy side of that positively charged amino acid reside. The trypsin protease is known to cleave a peptide on the carboxy side of a lysine or an arginine residue.

A wide variety of different protease cleavable peptides that comprise from 3 amino acid residues to 25 amino acid residues may be used in the present disclosure. In some embodiments, the protease cleavable peptide comprises from 5 amino acid residues to 15 amino acid residues. In some embodiments, the protease cleavable peptide comprises from 5 amino acid residues to 10 amino acid residues. In some embodiments, the protease cleavable peptide comprises amino acid residues selected from lysine, arginine, or glycine. In some aspects of the present disclosure, the protease cleavable peptide comprises at least one arginine or lysine and a C-terminus lysine to form a trypsin cleavage site. Some non-limiting examples of trypsin cleavable peptide include, but are not limited to, GRK, GKK, GRGK (SEQ ID NO: 2), GKGK (SEQ ID NO: 3), GRRGK (SEQ ID NO: 4), GRKGK (SEQ ID NO: 5), GKKGK (SEQ ID NO: 6), GRRRGK (SEQ ID NO: 1), GKRRGK (SEQ ID NO: 7), GKKRGK (SEQ ID NO: 8), GKKKGK (SEQ ID NO: 9), GRGRGK (SEQ ID NO: 10), GKGKGK (SEQ ID NO: 11), GRRRRGK (SEQ ID NO: 12), GKRRRGK (SEQ ID NO: 13), GRKRRGK (SEQ ID NO: 14), GRRKRGK (SEQ ID NO: 15), GRRRKGK (SEQ ID NO: 16), GKKRRGK (SEQ ID NO: 17), GRKKRGK (SEQ ID NO: 18), GRRKKGK (SEQ ID NO: 19), GRKRKGK (SEQ ID NO: 20), GKRKRGK (SEQ ID NO: 21), GGRRRGK (SEQ ID NO: 22), GRGRRGK (SEQ ID NO: 23), GRRGRGK (SEQ ID NO: 24), GRRRGGK (SEQ ID NO: 25), GGGRRGK (SEQ ID NO: 26), GRGGRGK (SEQ ID NO: 27), GRRGGGK (SEQ ID NO: 28), GRGRGGK (SEQ ID NO: 29), GGRGRGK (SEQ ID NO: 30), GKGGGGK (SEQ ID NO: 31), GGKGGGK (SEQ ID NO: 32), GGGKGGK (SEQ ID NO: 33), GGGGKGK (SEQ ID NO: 34), GKKGGGK (SEQ ID NO: 35), GGKKGGK (SEQ ID NO: 36), GGGKKGK (SEQ ID NO: 37), GGKGKGK (SEQ ID NO: 38), GKGKGGK (SEQ ID NO: 39), GRKGGGK (SEQ ID NO: 40), GGRKGGK (SEQ ID NO: 41), GGGRKGK (SEQ ID NO: 42), GGRGKGK (SEQ ID NO: 43), GRGKGGK (SEQ ID NO: 44), GKRGGGK (SEQ ID NO: 45), GGKRGGK (SEQ ID NO: 46), GGGKRGK (SEQ ID NO: 47), GGKGRGK (SEQ ID NO: 48), GKGRGGK (SEQ ID NO: 49), or GKKKKGK (SEQ ID NO: 50).

In some aspects, the protease cleavable peptide is cross-linked through carboxylic acid groups of the polymer with the amine groups of the protease cleavable peptide. The polymers that may be used in the present disclosure include P(MAA-co-NVP). In some embodiments, the protease cleavable peptide comprises a terminal lysine group. In some embodiments, the cross-linked peptide is linked to the polymer through the N-terminus and the G-amine group of the terminal lysine leaving the C-terminus of the lysine as a free carboxylate.

In order to cross-link the polymer or hydrogel with a protease cleavable peptide, the polymer is reacted with a coupling agent to generate an activated carboxylic acid group. In some embodiments, the coupling agent generates an activated carboxylic acid group which is more susceptible to the nucleophilic addition of the peptide. A non-limiting example of coupling agents include carbodiimide based coupling reagents, such as EDC, DCC, and DIC; uronium based coupling agents, such as BOP, PyBOP, HBTU, HATU, TBTU; and acid halide generating reagents, such as phosphorus pentachloride, oxalyl chloride, thionyl chloride, or phosgene. In some embodiments, the coupling agent is used in conjunction with hydroxylamide or a hydroxylamine. In some embodiment, the polymer is crosslinked with a protease cleavable peptide using a carbodiimide coupling reagent and a hydroxylamide such as N-hydroxysuccinimide. In some embodiments, the polymer is crosslinked with a protease cleavable peptide with EDC and N-hydroxysuccinimde.

In some aspects, the polymer is crosslinked in an 1:1 (v/v) ethanol:water mixture with the coupling agent and NHS. The polymer may be added to the coupling reagent and NHS in a ratio of about 1:1:1 to about 6:3:1 polymer to coupling reagent to NHS. In some embodiments, the ratio of coupling reagent and NHS to polymer is added at about 6:3:1 polymer:EDC:NHS. The reagents are mixed and/or vortexed and then the pH of the solution is adjust to about 8 using a strong base such as a metal hydroxide. The peptide is added to the solution in a ratio of 1:1 to about 5:1 polymer to peptide. The mixture is reacted for about 12 to about 48 hours. The resultant crosslinked polymer is purified to obtain the desired peptide-crosslinked hydrogel.

The crosslinked polymer may be used as obtained or subjected to further processing or purification. The cross-linked polymer may be subjected to repeated washings (such as with water) to remove unreacted starting materials or crosslinking by-products, subjected to centrifugation, or lyophilization. Additionally, other purification methods may be used such as chromatography or extractions. In some aspects, the dry, crosslinked polymer may be milled or crushed to obtain a fine powder. The powder may be used as is or further sifted to obtain a particle size of less than 2000 μm. In some embodiments, the powder is sifted into particles with a range of desired sizes, e.g., about 30-75 μm, 10-1000 μm, 20-500 μm, 10-100 μm, or about 10, 20, 30, 35, 40, 45, 50, 55, 60, 65, 70, 75, 80, 85, 90, 100, 200, 300, 400, 500, 1000, 2000 μm or any range derivable therein.

III. CATIONIC NANOPARTICLES AND POLYMERS

In some aspects, the polymers of the present disclosure include a nanoparticle or polymer with a positive charge. A wide variety of nanoparticles or polymers may be used including but not limited to chitosan, poly(ethyleneimine), poly(amidoamine), or a poly(aminoalkyl methacrylate). The nanoparticles or polymers may comprise one or more amino groups which are protonated at the pH of the solution to give the nanoparticle a positive charge. In some particular embodiments, the nanoparticles comprises one more poly (aminoalkyl methacrylate). Some examples of poly(amino-alkyl methacrylate) include poly(2-(diethylaminoethyl) methacrylate) and poly(2-(dimethylaminoethyl) methacrylate). In some embodiments, the methacrylate has been substituted with an amino containing alkyl chain. The amino group can be a primary, secondary (e.g. alkylamine), or tertiary (e.g. dialkylamine) amine. The amino substituted alkyl chain has between 1 and 12 total carbon atoms in some embodiments. In another embodiments, the amino substituted alkyl chain has between 1 and 8 total carbon atoms. In some embodiments, the nanoparticles may have a size from about 50-200 nm.

IV. THERAPEUTIC NUCLEIC ACIDS

In some embodiments, a polymer as described herein may comprise or be used to deliver one or more therapeutic nucleic acids or polynucleotides. The therapeutic nucleic acid or polynucleotide may be an inhibitory nucleic acid that can reduce the expression or translation of a gene or promote degradation of particular RNA species. In some embodiments, the therapeutic nucleic acid may cause or promote the transcription or activation of a gene or gene product. For example, in some embodiments the therapeutic nucleic acid may comprise a promoter operably linked to a polynucleotide that encodes a therapeutic protein; optionally, the nucleic acid may also encode an enhancer. In some embodiments, the therapeutic nucleic acid is from 15-50, 17-30, or 17-25 nucleotides in length, or any range derivable therein. Examples of an inhibitory nucleic acid that may be used include but are not limited to molecules targeted to an nucleic acid sequence, such as an small interfering RNA (siRNA), short hairpin RNA (shRNA), double-stranded RNA, micro RNA (miRNA) an antisense oligonucleotide, a ribozyme and molecules targeted to a gene or gene product such as an aptamer.

An inhibitory nucleic acid may selectively inhibit the transcription of a gene or prevent the translation of the gene transcript in a cell. An inhibitory nucleic acid may be, e.g., from 4-1000 or 16-1000 nucleotides long. In some embodiments, an inhibitory nucleic acid is from 18 to 100 nucleotides long. Various therapeutic nucleotides are known in the art. For example, genes that may be therapeutically targeted by a nucleic acid include, e.g., tumor necrosis factor-α. In some embodiments, the therapeutic nucleic acid may be transcribed in a cell to produce a therapeutic protein in the cell.

Inhibitory nucleic acids are well known in the art. For example, siRNA, shRNA and double-stranded RNA have been described in U.S. Pat. Nos. 6,506,559 and 6,573,099, as well as in U.S. Patent Publications 2003/0051263, 2003/0055020, 2004/0265839, 2002/0168707, 2003/0159161, and 2004/0064842, all of which are herein incorporated by reference in their entirety.

In designing a nucleic acid capable of generating an RNAi effect, there are several factors that need to be considered such as the nature of the siRNA, the durability of the silencing effect, and the choice of delivery system. To produce an RNAi effect, the siRNA that is introduced into the organism will typically contain exonic sequences. Furthermore, the RNAi process is homology dependent, so the sequences must be carefully selected so as to maximize gene specificity, while minimizing the possibility of cross-interference between homologous, but not gene-specific sequences. Particularly the siRNA exhibits greater than 80, 85, 90, 95, 98% or even 100% identity or complementarity between the sequence of the siRNA and a portion of an target nucleotide sequence. Sequences less than about 80% identical to the target gene are typically substantially less effective. Thus, the greater identity between the siRNA and the gene to be inhibited, the less likely expression of unrelated genes will be affected.

In addition, the size of the siRNA may be an important consideration. In some embodiments, siRNA molecules that are from 19-27 nucleotides in length, more preferably 20-25 nucleotides in length, may be used as the therapeutic nucleotide and may be used to selectively inhibit translation of a particular gene. In some embodiments, the therapeutic nucleotide is an antisense oligonucleotide. The antisense oligonucleotide may be less than 500, 200, 100, 50, 25, or 20 nucleotides in length. In some embodiments, the therapeutic nucleotide is an miRNA that is from about 19-24, or 19, 20, 21, 22, 23 nucleotides in length, or any range derivable therein.

Within an inhibitory nucleic acid, the components of a nucleic acid need not be of the same type or homogenous throughout (e.g., an inhibitory nucleic acid may comprise a nucleotide and a nucleic acid or nucleotide analog). Typically, an inhibitory nucleic acid can form a double-stranded structure; the double-stranded structure may result from two separate nucleic acids that are partially or completely complementary. In certain embodiments of the present invention, the inhibitory nucleic acid may comprise only a single nucleic acid (polynucleotide) or nucleic acid analog and form a double-stranded structure by complementing with itself (e.g., forming a hairpin loop). The double-stranded structure of the inhibitory nucleic acid may comprise 16-500 or more contiguous nucleobases, including all ranges derivable thereof. The inhibitory nucleic acid may comprise or consist of 17 to 35 contiguous nucleobases, more particularly 18 to 30 contiguous nucleobases, more particularly 19 to 25 nucleobases, more particularly 20 to 23 contiguous nucleobases, or 20 to 22 contiguous nucleobases, or 21 contiguous nucleobases that can selectively hybridize with a complementary nucleic acid within the same sequence or with a separate mRNA of interest (e.g., the complementary sequence may be located on the same nucleic acid or may be present in a separate complementary nucleic acid) to form a double-stranded structure. In some embodiments, the RNA may be protected with a chemical modification to slow degradation in the body or bloodstream of a mammalian subject such as a human. In some embodiments, the therapeutic RNA is a locked nucleic acid (LNA).

siRNA can be obtained from commercial sources, natural sources, or can be synthesized using any of a number of techniques well-known to those of ordinary skill in the art. An inhibitory nucleic acid that can be applied in the compositions and methods of the present invention may be any nucleic acid sequence that has been found by any source to be a validated downregulator of the gene or gene product.

In one embodiment, the siRNA molecule is at least 75, 80, 85, or 90% homologous, particularly at least 95%, 99%, or 100% similar or identical, or any percentages in between the foregoing (e.g., the invention contemplates 75% and greater, 80% and greater, 85% and greater, and so on, and said ranges are intended to include all whole numbers in between), to at least 10 contiguous nucleotides of any of the nucleic acid sequences encoding a target therapeutic protein.

The siRNA may also comprise an alteration of one or more nucleotides. Such alterations can include the addition of non-nucleotide material, such as to the end(s) of the 19 to 25 nucleotide RNA or internally (at one or more nucleotides of the RNA). In certain aspects, the RNA molecule contains a 3'-hydroxyl group. Nucleotides in the RNA molecules of the present invention can also comprise non-standard nucleotides, including non-naturally occurring nucleotides or deoxyribonucleotides. The double-stranded oligonucleotide may contain a modified backbone, for example, phosphorothioate, phosphorodithioate, or other modified backbones known in the art, or may contain non-natural internucleoside linkages. Additional modifications of siRNAs (e.g., 2'-O-methyl ribonucleotides, 2'-deoxy-2'-fluoro ribonucleotides, "universal base" nucleotides, 5-C-methyl nucleotides, one or more phosphorothioate internucleotide linkages, and inverted deoxyabasic residue incorporation) can be found in U.S. Publication 2004/0019001 and U.S. Pat. No. 6,673,611 (each of which is incorporated by reference in its entirety). Collectively, all such altered nucleic acids or RNAs described above are referred to as modified siRNAs.

In one embodiment, siRNA is capable of decreasing the expression of a particular genetic product by at least 10%, at least 20%, at least 30%, or at least 40%, at least 50%, at least 60%, or at least 70%, at least 75%, at least 80%, at least 90%, at least 95% or more or any ranges in between the foregoing.

V. THERAPEUTIC PROTEINS

In some embodiments, the hydrogel copolymers may comprise or contain a therapeutic protein. The therapeutic protein may be a natural and nonnatural (e.g., recombinant) proteins, polypeptides, and peptides. The proteins may, by themselves, be incapable of passing (or which pass only a fraction of the administered dose) through the gastrointestinal mucosa or may be susceptible to chemical cleavage by acids or enzymes in the gastrointestinal tract or both. In addition to proteins, the hydrogel network also may include polysaccharides, and particularly mixtures of mucopolysaccharides, carbohydrates, lipids; other organic compounds. For therapeutic applications, the protein may be biologically active.

Examples of proteins that may be comprised in a hydrogel copolymer of the present invention include, but are not limited to, synthetic, natural, or recombinant sources of: a growth hormone (e.g., a somatotropin, e.g., GENOTROPIN®, NUTROPIN®, NORDITROPIN®, SAIZEN®, SEROSTIM®, HUMATROPE®), including a human growth hormone (hGH), a recombinant human growth hormone (rhGH), a bovine growth hormone, or a porcine growth hormone; a growth hormone-releasing hormone; an interferon (e.g., IFN-γ, IFN-α, IFN-β, IFN-ω, IFN-τ; IFN-κ); an interleukin (e.g., IL-I; IL-2, including, e.g., PROLEUKTN®; IL-3, IL-4, IL-5, IL-6, IL-7, IL-8, IL-9; and the like); a growth factor (e.g., REGRANEX® (beclapermin; PDGF); FIBLAST® (trafermin; bFGF); STEMGEN® (ancestim; stem cell factor); a keratinocyte growth factor; an acidic fibroblast growth factor, a stem cell factor, a basic fibroblast growth factor, a hepatocyte growth factor; insulin, including porcine, bovine, human, and human recombinant insulin (e.g., Novolin, Humulin, Humalog, Lantus, Ultralente), optionally having counter ions including sodium, zinc, calcium and ammonium; an insulin-like growth factor, including IGF-I; a heparin, including unfractionated heparin, heparinoids, dermatans, chondroitins, low molecular weight heparin, very low molecular weight heparin and ultra low molecular weight heparin; calcitonin, including salmon, eel, and human calcitonin; erythropoietin (e.g., PROCRIT®, EPREX®, or EPOGEN® (epoetin-α); ARANESP® (darbepoetin-α); NEORECORMON®, EPOGIN® (epoetin-β); and the like); a blood factor (e.g., ACTIVASE® (alteplase) tissue plasminogen activator; NOVOSEVEN® (recombinant human factor VIIa); Factor VIIa; Factor VIII (e.g., KOGENATE®); Factor IX; β-globin; hemoglobin; and the like); a colony stimulating factor (e.g., NEUPOGEN® (filgrastim; G-CSF), NEULASTA® (pegfilgrastim), a granulocyte colony stimulating factor (G-CSF), a granulocyte-monocyte colony stimulating factor, a macrophage colony stimulating factor, a megakaryocyte colony stimulating factor; and the like); an antigen; an antibody (e.g., a monoclonal antibody) (e.g., RITUXAN® (rituximab); REMICADE® (infliximab); HERCEPTIN® (trastuzumab); HUIIVIIRA™ (adalimumab); XOLAIR® (omalizumab); BEXXAR® (tositumomab); RAPTIVA™ (efalizumab); ERBITUX™ (cetuximab); and the like), an scFv region, or an antibody fragment, including an antigen-binding fragment of a monoclonal antibody; a soluble receptor (e.g., a TNF-α-binding soluble receptor such as ENBREL® (etanercept); a soluble VEGF receptor; a soluble interleukin receptor; a soluble γ/δ T cell receptor; and the like); an enzyme (e.g., α-glucosidase; CERAZYME® (imiglucarase; β-glucocerebrosidase, CEREDASE® (alglucerase); an enzyme activator (e.g., tissue plasminogen activator); a chemokine (e.g., IP-IO; Mig; Groα/IL-8, RANTES; MIP-Ia; MIP-I β; MCP-I; PF-4; and the like); an angiogenic agent (e.g., vascular endothelial growth factor (VEGF); an anti-angiogenic agent (e.g., a soluble VEGF receptor); a neuroactive peptide such as bradykinin, cholecystokinin, gastin, secretin, oxytocin, gonadotropin-releasing hormone, beta-endorphin, enkephalin, substance P, somatostatin, prolactin, galanin, growth hormone-releasing hormone, bombesin, warfarin, dynorphin, neurotensin, motilin, thyrotropin, neuropeptide Y, luteinizing hormone, calcitonin, insulin, glucagon, vasopressin, angiotensin II, thyrotropin-releasing hormone, vasoactive intestinal peptide, a sleep peptide, nesiritide, octreotide, teriparatide, pramlintide, and the like; a thrombolytic agent; an atrial natriuretic peptide; a bone morphogenic protein; thrombopoietin; relaxin; glial fibrillary acidic protein; a follicle stimulating hormone; a human alpha-1 antitrypsin; a leukemia inhibitory factor; a transforming growth factor; a tissue factor; a luteinizing hormone; a leutinizing-hormone-releasing-hormone; a macrophage activating factor, a tumor necrosis factor, a neutrophil chemotactic factor, a nerve growth factor, a tissue inhibitor of metalloproteinases; a vasoactive intestinal peptide, angiogenin, angiotropin, fibrin; hirudin; a leukemia inhibitory factor; an IL-I receptor antagonist (e.g., KINERET® (anakinra)); a protease inhibitor; adrenocorticotropin; a prostaglandin; cyclosporin; cromolyn sodium (sodium or disodium chromoglycate); vancomycin; desferoxamine (DFO); parathyroid hormone (PTH), including its fragments; an antimicrobial; and an anti-fungal agent. Combinations, analogs, fragments, mimetics or polyethylene glycol (PEG)-modified derivatives of these compounds, or other derivatives of any of the above-mentioned substances may also be suitable. Also suitable for use are fusion proteins comprising all or a portion of any of the foregoing proteins. One of ordinary skill in the art, with the benefit of the present disclosure, may recognize additional drugs, including drugs other than proteins or polynucleotides, that may be useful in the compositions and methods of the present disclosure. Such drugs are still considered to be within the spirit of the present disclosure.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Enzymatic Biodegradation of Hydrogels for Protein Delivery Targeted to the Small Intestine Materials Methacrylic acid (MAA), N-vinyl-2-pyrrolidone (NVP), Irgacure 184® (1-hydroxy-cyclohexyl-phenylketone), 1-ethyl-3-(3-dimethylaminopropyl) carbodiimide hydrochloride (EDC), purified pepsin from porcine gastric mucosa (≥2500 U/mg) and pancreatin from porcine pancreas (4×USP specifications), trypsin-EDTA solution (1×) and Nα-benzoyl-L-arginine ethyl ester hydrochloride (BAEE) trypsin substrate, and recombinant human insulin (≥27.5 IU/mg) were purchased from Sigma-Aldrich (St. Louis, Mo.). N-hydroxysuccinimide (NETS) was purchased from Pierce Biotechnology, Inc. (Rockford, Ill.). The custom sequence oligopeptide GRRRGK (SEQ ID NO: 1) was synthesized by CHI Scientific (Maynard, Mass.). Fluorescamine was purchased from Acros Organics (Geel, Belgium). All reagents were used as received. All other solvents and buffers were purchased from Fisher Scientific (Waltham, Mass.).

Methods

Synthesis and Purification

P(MAA-co-NVP) linear polymer was synthesized by photoinitiated, free-radical polymerization. MAA and NVP were added at a 1:1 molar ratio to a 1:1 (w/w) deionized water and ethanol solution to yield a 1:3 (w/w) total monomer to solvent ratio. Photoinitiator Irgacure 184® was added at 1 wt % with respect to total monomer weight. The mixture was homogenized by sonication then the flask was sealed with a rubber septum. The solution was purged with nitrogen for 20 minutes, then the polymerization was initiated with a Dymax BlueWave® 200 UV point source (Dymax, Torrington, Conn.) at 100 mW/cm$^2$ intensity and allowed to polymerize for 30 minutes while stirring.

Following polymerization, the linear polymer was purified from unreacted monomer by addition of 1 N hydrochloric acid (HCl) to precipitate polymer, centrifugation, and resuspension in deionized water. After three wash cycles, the polymer solution was neutralized, frozen in liquid nitrogen, and lyophilized.

To synthesize the peptide-crosslinked hydrogels, linear P(MAA-co-NVP) was dissolved in a 1:1 (v/v) water:ethanol solution at a concentration of 50 mg/ml. EDC was dissolved in ethanol at a concentration of 50 mg/ml and NHS was dissolved in ethanol at a concentration of 16 mg/ml. The EDC and NHS solutions were added to the polymer solution at a ratio of 6:3:1 polymer:EDC:NHS by weight. The solution was mixed by vortex, then allowed to react for ~3 min with shaking. The pH was raised to ~8 by the addition of 1 N sodium hydroxide (NaOH), and then a volume of 100 mg/ml peptide in ethanol solution was added to achieve a 2:1 weight ratio of polymer:peptide. The mixture was allowed to react overnight with shaking then purified by three wash cycles with water and centrifugation at 10,000×g for 5 minutes. Following the washes, the polymer was frozen in liquid nitrogen and lyophilized for at least 24 hours.

After lyophilization, the polymer was milled into a fine power by crushing with mortar and pestle. The powder was sifted to the size ranges of 30-75 μm and less than 30 μm by ultraprecision ASTM sieves (Precision Eforming, Cortland, N.Y.).

Potentiometric Titration

To determine the MAA content of the linear polymer, a 3.5 mg/ml solution of polymer in deionized water was titrated to pH 11.5 using 0.2 N NaOH (standardized with potassium hydrogen phthalate) at 25° C. with constant stirring. pH was measured with a Mettler-Toledo SevenEasy™ (Columbus, Ohio) pH probe and was recorded when the pH reached a steady value (±0.01 pH units in three consecutive measurements over 5 minutes). The equivalence point was used in conjunction with a charge balance to determine the amount of MAA present in each formulation.

Fluorescamine Assay

The fluorescamine solution was prepared fresh before each test by dissolving 3 mg of fluorescamine in 10 ml filtered acetone. Supernatant from the EDC-NHS reactions was mixed in a range of dilutions with phosphate buffered saline (PBS) and the fluorescamine solution with agitation. After reacting at room temperature with shaking for 15 min, 200 μl of each sample was transferred in triplicate to a black 96-well plate and the fluorescence at 360 ex/460 em was measured using a Bio-Tek Synergy™ HT multi-mode plate reader (Winooski, Vt.), sensitivity=85.

Fourier Transform Infrared Spectroscopy

Fourier transform infrared spectroscopy (FTIR) spectra were obtained using a Thermo Mattson Infinity Gold spectrometer (Thermo Fisher Scientific Inc., Waltham, Mass.). The incubation buffer of degraded hydrogel samples was exchanged with water using 30,000 MWCO centrifugal filters (Millipore, Billerica, Mass.) over 5 washes. Samples were lyophilized and then pressed in KBr (Sigma-Aldrich) disks. For each sample, 512 scans were performed with a resolution of 4 cm$^{-1}$ and gain of 1.0, and background spectra of a KBr blank disk was subtracted from the sample spectra.

Scanning Electron Microscopy

Scanning electron microscopy (SEM) samples were prepared by dusting carbon tape-covered aluminum stubs with lyophilized, crushed microgels. The samples were coated with 8-10 nm of Pt/Pd coating using a Cressington 208 Benchtop sputter coater (Watford, England). Scanning electron microscopy images were obtained using an FEI Quanta 650 FEG scanning electron microscope (Hillsboro, Oreg.) and a Zeiss Supra 40V scanning electron microscope (Jena, Germany).

Degradation

Microgels were degraded at various trypsin concentrations in 1× phosphate buffered saline solution (pH 7.4), simulated gastric fluid, simulated intestinal fluid, rat gastric fluid or rat intestinal fluid. Simulated gastric fluid (SGF) and simulated intestinal fluid (SIF) were prepared according to USP 29 (Pharmacopeia, 2006). Briefly, the SGF was prepared by dissolving 2 g of sodium chloride and 3.2 g of purified pepsin from porcine stomach mucosa was dissolved in ~800 ml deionized water. 7 ml of HCl was added, followed by enough water to make up to 1 L and the pH adjusted to 1.2. SIF was prepared by dissolving 6.8 g monobasic potassium phosphate in 250 ml deionized water, then 77 ml of 0.2 N NaOH was added while stirring. 500 ml additional water was added then 10 g pancreatin was mixed into the solution. The pH was adjusted to 6.8 using 0.2 N NaOH or HCl then the solution was made up to 1 L with water.

Gastrointestinal fluids were harvested from Sprague Dawley juvenile male rats (250-300 g) according to a protocol published by Yamagata et al. with some modifications (Yamagata et al., 2006). Briefly, after sacrificing the rat the stomach was excised and ligated at both ends. A needle was inserted to inject 5 ml of pH 1.2 HCl—NaCl buffer (same as SGF minus pepsin) and the gastric contents were collected in a 50 ml centrifuge tube. Similarly, a ~20 cm section of the upper small intestine was cannulated and flushed twice with 10 ml cold PBS (1×, pH 7.4). The fluid was collected as intestinal fluid in a 50 ml centrifuge tube. Both the harvested fluids were centrifuged at 3,200×g, 4° C., for 15 min to separate solids from the fluids. The supernatants were retained as rat gastric fluid and rat intestinal fluid, respectively. Fluids were stored at −20° C. until use.

Degradation was measured by relative turbidity of the solutions over time, as reported by Klinger and Landfester, 2012. Microgels were suspended in trypsin solutions of varying concentration, PBS, SGF, SIF, or rat gastrointestinal fluids at various concentrations. 100 µl of each solution was added to a 96-well plate in triplicate, and the absorbance was measured at 500 nm in 5 minute intervals over 90 minutes using a Bio-Tek Synergy™ HT multi-mode plate reader (Winooski, Vt.). The temperature was controlled at 37° C. and the plate underwent shaking for 3 seconds before each measurement.

Activity of the trypsin following incubation with particles and deactivation methods including addition of serum-containing cell culture media or 5 minutes incubation at 60° C., 70° C., or 80° C., was evaluated using a trypsin activity assay adapted from the protocol by Yanes et al., 2007. Briefly, degradation supernatant was combined with 1 mg/ml BAEE in PBS at a 1:9 sample:BAEE ratio by volume. Immediately after addition of the BASE, absorbance at 253 nm was measured at the minimum interval (typically 40-50 seconds) for 5 minutes using a Bio-Tek Synergy™ HT multi-mode plate reader (Winooski, Vt.).

In Vitro Cytotoxicity Study

L929 and RAW 264.7 cell lines were obtained from American Type Culture Collection (ATCC, Rockwell, Md.). All cell lines were cultured in Dulbecco's modified Eagle medium (DMEM) (Mediatech, Herndon, Va.) supplemented with 10% heat-inactivated HyClone™ Fetal Bovine Serum, USDA Tested (Fisher Scientific), 1% 200 mM L-glutamine solution (Mediatech), 100 U/ml penicillin, and 100 µg/ml streptomycin (Mediatech). Cytotoxicity studies were performed using DMEM without phenol red supplemented with 2% heat-inactivated HyClone™ Fetal Bovine Serum, USDA Tested (Fisher Scientific), 1% non-essential amino acids (Mediatech), 100 U/ml penicillin, and 100 µg/ml streptomycin (Mediatech). Cells were incubated at 37° C. in a 5% $CO_2$ environment.

Cells were seeded at a density of 10,000 cells/well in a 96-well plate and allowed to incubate for 24 hours prior to the experiment. Microgels were degraded in 1.25 or 0.625 mg/ml trypsin in PBS at concentrations ranging from 1.3-6 mg/ml. Degradation took place at 37° C. with shaking for at least 4 hours. Trypsin was deactivated by addition of 2× volume DMEM without phenol red containing 2% fetal bovine serum. Cells were incubated with degraded microgels for 8 hours at 37° C. and 5% $CO_2$. The cytotoxic effect of the microgels was evaluated using a CellTiter 96® Aqueous One Solution Cell Proliferation MTS Assay (Promega, Madison, Wis.). MTS assay was added to the wells and incubated for 90 minutes at the same conditions before absorbance measurements were made at 490 nm using a Bio-Tek Synergy™ HT multi-mode plate reader (Winooski, Vt.). Cytotoxicity is reported as 'relative cell proliferation', or normalization of the assay absorbance values to the average assay absorbance for cells incubated in only culture media.

Insulin Loading

Microgels were loaded by equilibrium partitioning post-synthesis with recombinant human insulin. Microgels were incubated at 37° C. for 4 hours in a 0.5 mg/mL insulin solution of pH ~5.5 at a ratio of 7:1 microgel:therapeutic by weight. The microgels were collected by centrifugation at 10,000×g for 5 minutes then collapsed by resuspension in 0.5 N HCl. Microgels were separated from supernatant by centrifugation at 10,000×g for 5 minutes. The loaded microgels were lyophilized and stored at −20° C. for further studies. Protein loading was evaluated with a MicroBCA assay protein quantification assay (Pierce-Thermo, Rockford, Ill.).

Results and Discussion

Synthesis, purification and lyophilization of the uncrosslinked P(MAA-co-NVP) yielded white, fluffy polymer. Due to the phase transition of MAA from hydrophobic to hydrophilic above pH ~5, adjusting the pH of the solution to neutral prior to freeze drying facilitated the solubilization of the dried polymer into aqueous solution. Potentiometric titration was used to determine that the linear polymer was approximately 45 mol % or 39 wt % MAA.

Scheme 1 shows the mechanism of the EDC-NHS crosslinking reaction with the linear P(MAA-co-NVP). Upon solubilization of the polymer in the ethanol-water solution, the pH was adjusted to ~5 to favor the activation of the carboxylic acid groups by EDC and increase the stability of the active ester intermediate (Hermanson, 1996). EDC was added at a molar ratio of 1:2 to the MAA groups on the linear chains, and NHS was added at a molar ratio of 1:1.8 to the EDC. Upon addition of the EDC and NHS the solution became turbid but no precipitation was evident. Both the EDC and NHS were dissolved in ethanol to limit instability due to hydrolysis while maintaining polymer solubility.

Scheme 1. Peptide crosslinking reaction scheme. Carboxylic acid groups on the poly(methacrylic acid-co-N-vinylpyrrolidone) linear polymer are activated by EDC, then react with at least two of the five primary amine groups on the GRRRGK (SEQ ID NO: 1) peptide to form a crosslinked hydrogel network.

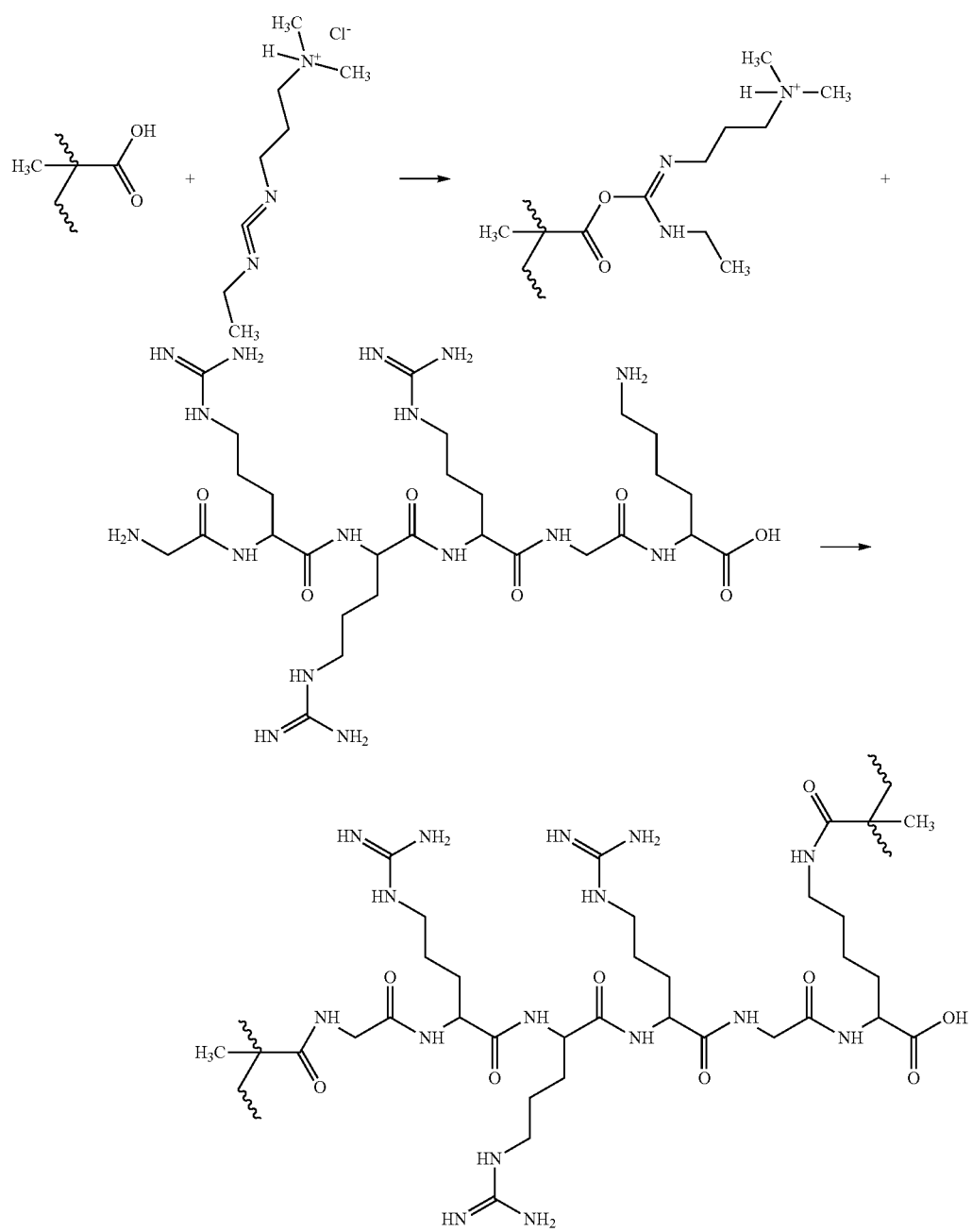

After activation of the carboxylic acid groups, the pH was raised to ~7-8 to facilitate attack on the primary amines of the oligopeptide (Hermanson, 1996). Various polymer:EDC: NHS:peptide weight ratios were tested to maximize peptide incorporation. All formulations with peptide content below a polymer:peptide ratio of ~3:1 failed to produce hydrogels. A best performing formulation of solvents, polymer, and EDC-NHS based on reaction efficiency and reproducibility was an ethanol-water mixture with a polymer:EDC:NHS: peptide weight ratio of 20:10:3.3:10.

The peptide was added at a molar ratio of 1:3.6 relative to the EDC; the free amine groups were in 1.4× excess relative to the theoretical maximum of activated carboxyl groups. Upon addition of the peptide solution the mixture was immediately turbid and precipitation of crosslinked polymer was evident. After reacting for at least 8 hours the cross-linked polymer typically resembled an amorphous hydrogel.

Following washes and lyophilization the hydrogel appeared as fluffy white chunks. The dried hydrogel was easily crushed into a powder consisting of particles <30 μm in size, shown in the SEM micrograph in FIGS. 1A-B.

Fluorescamine Assay

The fluorescamine assay was used to quantify the amount of peptide remaining in solution following the EDC-NHS crosslinking reaction. The fluorescamine reagent is commonly used as a fluorometric assay of free amine content, which can be used as a measurement of protein or peptide content (Bohlen et al., 1973). A known concentration of peptide was used as the standard to obtain quantitative results. Assay of the reaction conditions without peptide showed no background fluorescence as expected.

The fluoresecamine assay was used to measure the reaction efficiency as a function of the ratio of linear polymer to peptide. The reaction efficiencies of a 1:1 and a 2:1 polymer:peptide weight ratio were compared by quantifying the peptide remaining in solution at the completion of the reaction. In the case of the 1:1 ratio, 16.6 wt % of the peptide remained in solution. However, at the 2:1 ratio only 1.8 wt % of the peptide remained in solution. All subsequent reactions were carried out at the 2:1 polymer:peptide weight ratio.

FTIR Spectroscopy

Figure 2:
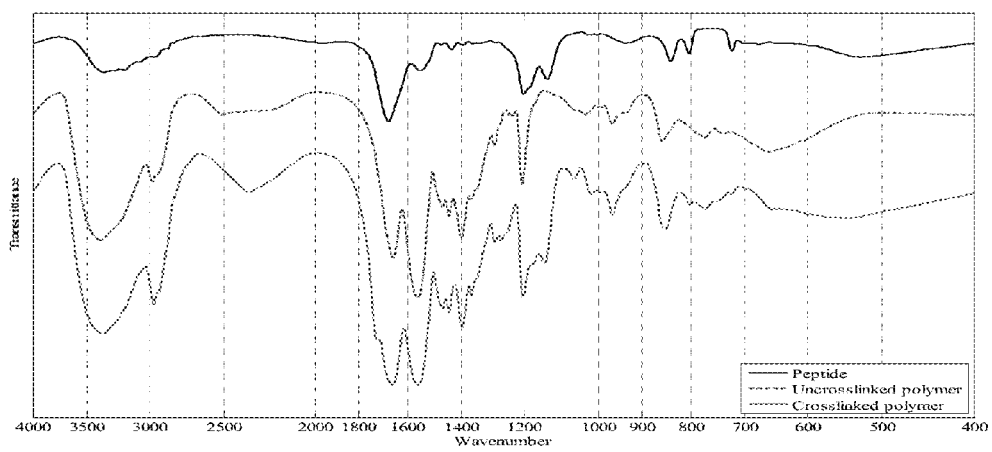
FIG. 2: FT-IR spectra of GRRRGK (SEQ ID NO: 1) peptide (——), uncrosslinked P(MAA-co-NVP) (— —), and peptide crosslinked P(MAA-co-NVP) (·····) samples were pressed in a KBr disk.
Figure 3:
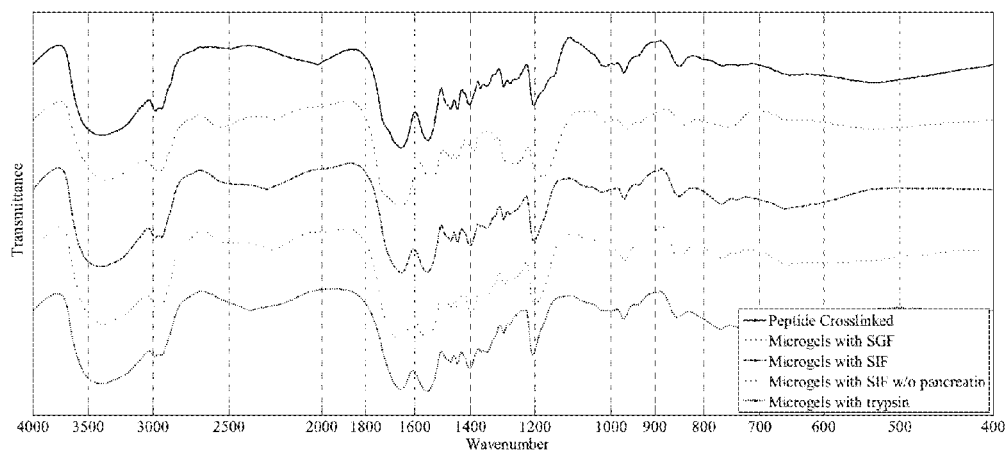
FIG. 3: FT-IR spectra of peptide crosslinked P(MAA-co-NVP) at neutral pH (——) and peptide crosslinked P(MAA-co-NVP) degradation products following incubation with SGF (········) SIF (— -), SIF without pancreatin (······ ··) or a trypsin solution (- -); samples were lyophilized and pressed in a KBr disk.

FTIR spectroscopy was used to evaluate the composition of the peptide-crosslinked microgels before and after degradation. As shown in FIG. 2, the characteristic bands of the carboxylic groups of MAA are present at 2900 cm$^{-1}$ and 1560 cm$^1$ and the bands of carbonyl groups in MAA and NVP are present at 1640 cm$^{-1}$. Characteristic bands of the peptide that can be attributed to CN and NH$_2$ stretching appear at 1140 cm$^{-1}$ and 800 cm$^{-1}$ (Kolev, T., 2006). Incorporation of the peptide into the crosslinked gel was confirmed by the presence of these bands. FIG. 3 shows that there was no discernable difference between the spectra of intact and degraded microgels. However, upon exposure to the low pH of the SGF the characteristic carbonyl bands were shifted from 1680 cm$^{-1}$ to 1725 cm$^{-1}$ and 1640 cm$^{-1}$ compared to that in the neutral pH SIF, indicating the presence of hydrogen bonding within the microgels at low pH conditions.

Degradation

The peptide crosslink was designed with multiple arginine and lysine residues so that it would be targeted specifically by the enzyme trypsin, prevalent in the small intestine but would not be susceptible to attack by the enzyme pepsin in the stomach (Vlieghe et al., 2010). Trypsin is known to cleave at the C-terminal of arginine and lysine residues (Olsen, 2004) and each peptide link has four possible cleavage sites as shown in Scheme 1.

First, degradation of the microgels was assessed visually in SGF containing the enzyme pepsin, SIF containing the enzyme trypsin, or PBS. The hydrogel in trypsin solution was no longer visible after only 30 minutes. However, the hydrogels in the pepsin and PBS solutions were still easily discernable after 4 hours of incubation.

Figures 4A, 4B, 4C, 4D, 4E, 4F:
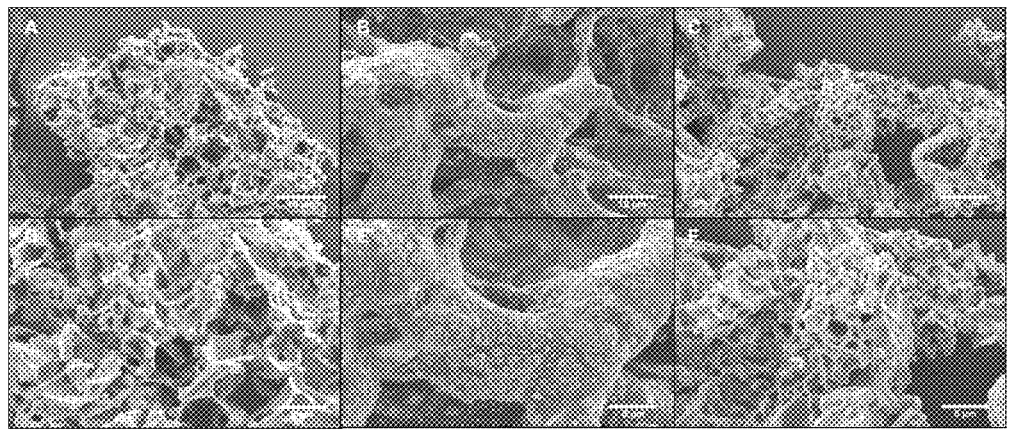
FIGS. 4A-4F: SEM micrographs of microgels after 90 minutes incubation in FIG. 4A) SGF (scale=10 µm)

SEM was used to visualize the morphology of partially degraded microgels, shown in FIGS. 4A-F. The microgels were incubated in buffers for 90 minutes then the degraded samples were flash frozen in liquid nitrogen and lyophilized. A microgel in SGF is shown in FIG. 4A and FIG. 4D and a microgel in PBS is shown in FIG. 4C and FIG. 4F; in both cases, a macroporous structure caused by lyophilization is easily discernable and reflects the structural integrity of the hydrogel. A microgel in SIF is shown in FIG. 4B and FIG. 4E, and following incubation with enzyme the hydrogel structure appears to be collapsed rather than porous, confirming the loss of structural integrity due to degradation of the crosslinks.

As the method of synthesis yielded amorphous hydrogel pieces on the order of millimeters in size, gravimetric analysis of degradation over time was impractical to execute. Thus, a different method of assessing degradation was sought. Turbidity is commonly used to evaluate the temperature-dependent phase transition and swelling of thermoresponsive polymers such as poly(N-isopropyl acrylamide) (Xu et al., 2007; Qiu et al., 2007), and Klinger and Landfester, 2011 showed that for photo-degradable poly (methyl methacrylate) particles the change in hydrodynamic radius as a function of swelling and degradation correlated well with the decrease in turbidity.

Per the second report by Klinger and Landfester, 2012, change in relative turbidity could be used to evaluate degradation as a function of time. Klinger and Landfester attribute the reduction in turbidity during degradation to a loosening of the network, resulting in greater swelling of the gel therefore less contrast between the refractive indices of the solvent and the polymer Klinger and Landfester, 2011. Mathematically, it can be explained by the following equation for turbidity as described by Lechner, 2005:

$$\tau = \frac{\varphi Q_{ext} 3}{2d} \quad (1)$$

where $\varphi$ is the volume fraction of the particles, $Q_{ext}$ is the Mie extinction efficiency, and d is the particle diameter. In most cases, it is useful to make the substitution $$\varphi = \frac{c}{\rho} \quad (2)$$

where c=mass concentration of the particles and p=density of the particles.

$Q_{ext}$ is a function of the ratio of refractive indices of the particles and solvent, $n_p/n_0$, as well as the size of the particles, and decreases as the ratio $n_p/n_0$ or the particle diameter decreases.

Therefore, it was hypothesized that as the enzymatically-degradable microgels swelled then degraded into smaller particles and eventually into linear polymer chains with minimal contrast between refractive indices of the polymer and solvent, the turbidity should decrease over time in correlation with the extent of degradation. Absorbance of the degrading microgel solutions was measured at an arbitrary value of 500 nm as the absorbance of the solutions plateaued in the 300-800 nm range. The absorbance value was first converted to percent transmittance using the following equation $$I = 10^{(2-A)} \quad (3)$$

then to turbidity using the equation $$\tau(t) = -\ln\left(\frac{I_t}{I_0}\right) \quad (4)$$

where $I_t$ is transmittance of the sample at time t and $I_0$ is transmittance of pure solvent. Finally, relative turbidity, which permits better comparison between samples that vary in particle size, was calculated as $$\tau_{rel} = \frac{\tau(t)}{\tau(t=0)} \quad (5)$$

and plotted as a function of time.

Figure 5:
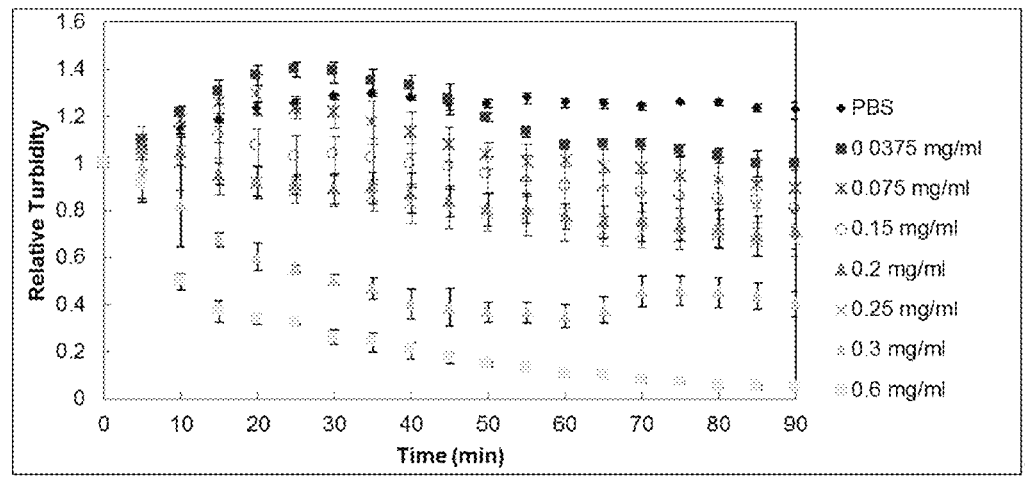
FIG. 5: Relative turbidity over time of 2 mg/ml solutions of P(MAA-co-NVP) microgels with degradable crosslinks incubated in trypsin solutions ranging from 0-0.6 mg/ml trypsin in PBS (37° C., pH 7.4, N=3).

As hypothesized, upon incubation with trypsin solutions of various concentrations the turbidity of the microgel solutions decreased over 90 minutes, shown in FIG. 5. The mass concentration of particles was held constant, therefore the trypsin concentration was directly related to decrease in relative turbidity; the higher the trypsin content, the greater the extent of degradation after 90 minutes. Interestingly, when microgels were incubated in low trypsin concentrations or in PBS there was an initial increase in turbidity followed by decreasing turbidity or a plateau in the case of PBS. As the particles are expected to swell in PBS and swell then degrade in the trypsin, this behavior is incongruent with the explanation set forth by Klinger and Landfesterm 2011, in which turbidity is expected to decrease with swelling of the particles. Looking at the relationship for turbidity established by Lechner in Eq. 1, turbidity is dependent upon particle size and concentration as well as the contrast between polymer and solvent refractive indices. This initial increase in turbidity may be attributed to the change in size of the particles due to swelling and bulk degradation. The imbibition of solvent by the swollen particles likely reduced the refractive index of the particles but was not sufficient to overcome the effect of the particle size contribution to turbidity as the microgels degraded into smaller pieces via bulk degradation. At approximately 30 minutes the particles in PBS reached equilibrium swelling, at which point the relative turbidity became constant. The point at which the degradation by trypsin was sufficient enough to overcome the effect of particle size and reduce the relative turbidity was dependent upon the concentration of trypsin, with the transition to decreasing relative turbidity happening sooner at higher trypsin concentrations where degradation is presumably happening on a faster timescale and surface degradation is controlling.

Drug release can be affected by a combination of reaction and diffusion phenomena, and drug release has been modeled for various systems. Lao et al., 2008 modeled tri-phasic drug release from bulk-degrading polymer blends by developing a three-step sequence to describe the diffusion of drug. Himmelstein and coworkers (Thombre and Himmel stein, 1985; Joshi and Himmelstein, 1991) developed models to describe the release of a model drug from poly(orthoester) during simultaneous diffusion-reaction transport due to acid-catalyzed hydrolysis. Others have modeled polymer degradation and drug release as a function of combined diffusion and enzyme-kinetics. For example, Anseth and coworkers (Rice et al., 2006) modeled the degradation of lipase-catalyzed hydrolysis of hydrogels for tissue engineering applications, and Cheng et al., 2011 modeled the release of a small molecule from enzymatically-degradable gelatin.

Figure 6:
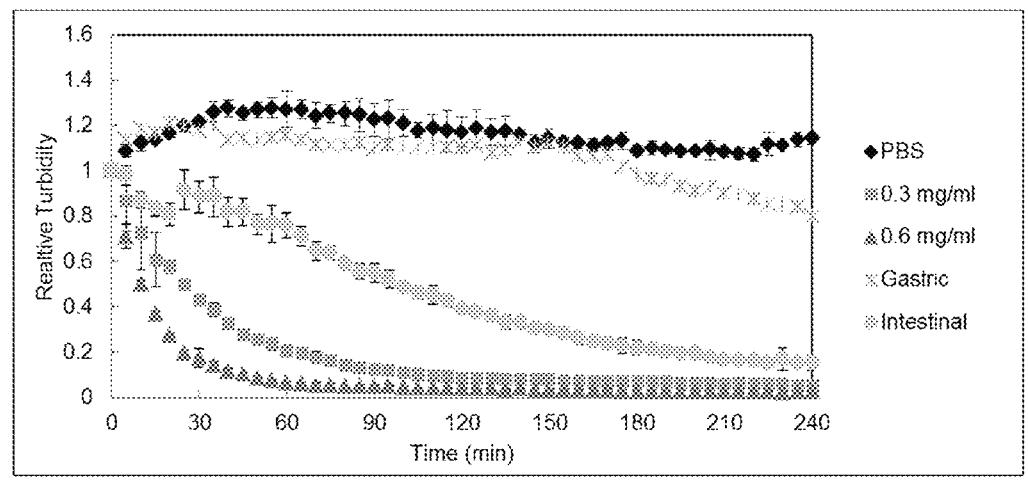
FIG. 6: Relative turbidity over time of 2 mg/ml solutions of P(MAA-co-NVP) microgels with degradable crosslinks incubated in PBS, 0.3 mg/ml trypsin in PBS, 0.6 mg/ml trypsin in PBS, rat gastric fluid*, or rat intestinal fluid (37° C., pH 7.4, N=3). *Gastric fluid error bars intentionally not shown to simplify the plot; error is ±0.24 on average in a consistent manner across the period of the study.

The degradation of the microgels during incubation with the rat gastrointestinal fluids versus trypsin solutions is shown in FIG. 6. As in the previous case, the relative turbidity of the microgels in PBS solution increased for the first ~30 minutes then was relatively constant over the remainder of the 4 hour incubation period. Relative turbidity of particle solutions at both the 0.3 and 0.6 mg/ml trypsin concentrations decreased to well below 10% by the end of the 4 hour incubation, with the solution with higher trypsin concentration reaching a lower value in a shorter period of time. The relative turbidity of the particles incubated with gastric fluid was approximately constant for nearly 3 hours, at which time the evaporation of the fluid started to have an effect on the enzyme concentration, the absorbance path length, or both, and turbidity decreased slightly. Most encouraging, though, was the significant degradation of the microgels incubated in rat intestinal fluid. The relative turbidity steadily decreased across the 4 hour incubation period, arriving at a final reduction in relative turbidity of 85%. Though the degradation was not as rapid as the trypsin solutions, the intestinal fluid was significantly diluted during harvest so it is quite possible that the physiological trypsin concentration is actually higher and able cause more rapid degradation in vivo. These results are extremely promising for oral drug delivery applications, as the degradation is specific to intestinal fluid and occurs on a timescale relevant to small intestinal residence time (Davis et al., 1986).

The activity of trypsin was evaluated by spectrophotometric measurement using BAEE, an arginine-containing substrate that absorbs at 253 nm upon cleavage by trypsin. Trypsin activity is correlated to rate of absorbance increase over the initial 5 minutes of the reaction, and the absorbance reaches a plateau when the cleavage reaction is complete). Due to the scale of the degradation reactions, the assay was adapted and optimized for a 96-well assay format on the microliter-scale as opposed to the previously reported milliliter-scale protocols (Yanes et al., 2007).

Using the optimized reaction conditions for the 96-well assay, various degradation and trypsin deactivation conditions were evaluated to determine the trypsin activity as a function of microgel concentration and subsequent deactivation method. The trypsin deactivation was carried out to ensure the trypsin would not negatively impact adherent cell lines during in vitro characterization studies. Microgel concentrations of 0, 1.5, 3, and 6 mg/ml were incubated with 0.6 mg/ml trypsin at 37° C. for 90 minutes.

Figure 7:
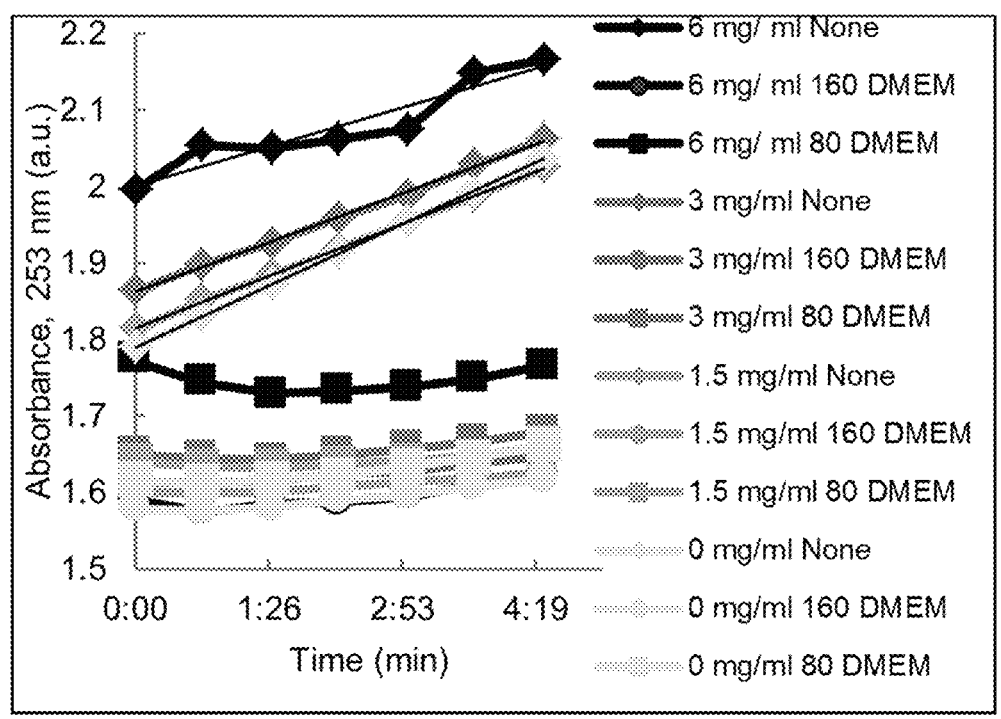
FIG. 7: Activity assay of 0.6 mg/ml trypsin incubated with various concentrations of P(MAA-co-NVP) microgels containing degradable crosslinks for 90 minutes, and then deactivated with 0, 80, or 160 µl DMEM (37° C., pH 7.4, N=3). Trypsin activity in the samples receiving no DMEM is evidenced by the strong linear correlation. Both volumes of DMEM were sufficient quench trypsin activity.

As shown in FIG. 7, the samples without deactivation had a strong linear correlation in absorbance increase over time; as previously reported, the greater the slope of this linear fit the higher the trypsin activity (Schwert and Takenaka, 1955). Slope and $R^2$ values of the linear fit for each particle concentration are shown in Table S.1, and it can be seen that trypsin activity on the BAEE substrate is reduced as microgel concentration increases. This confirmed the enzymatic reaction between the trypsin and the peptide crosslinks within the microgels.

Figures 8A, 8B, 8C:
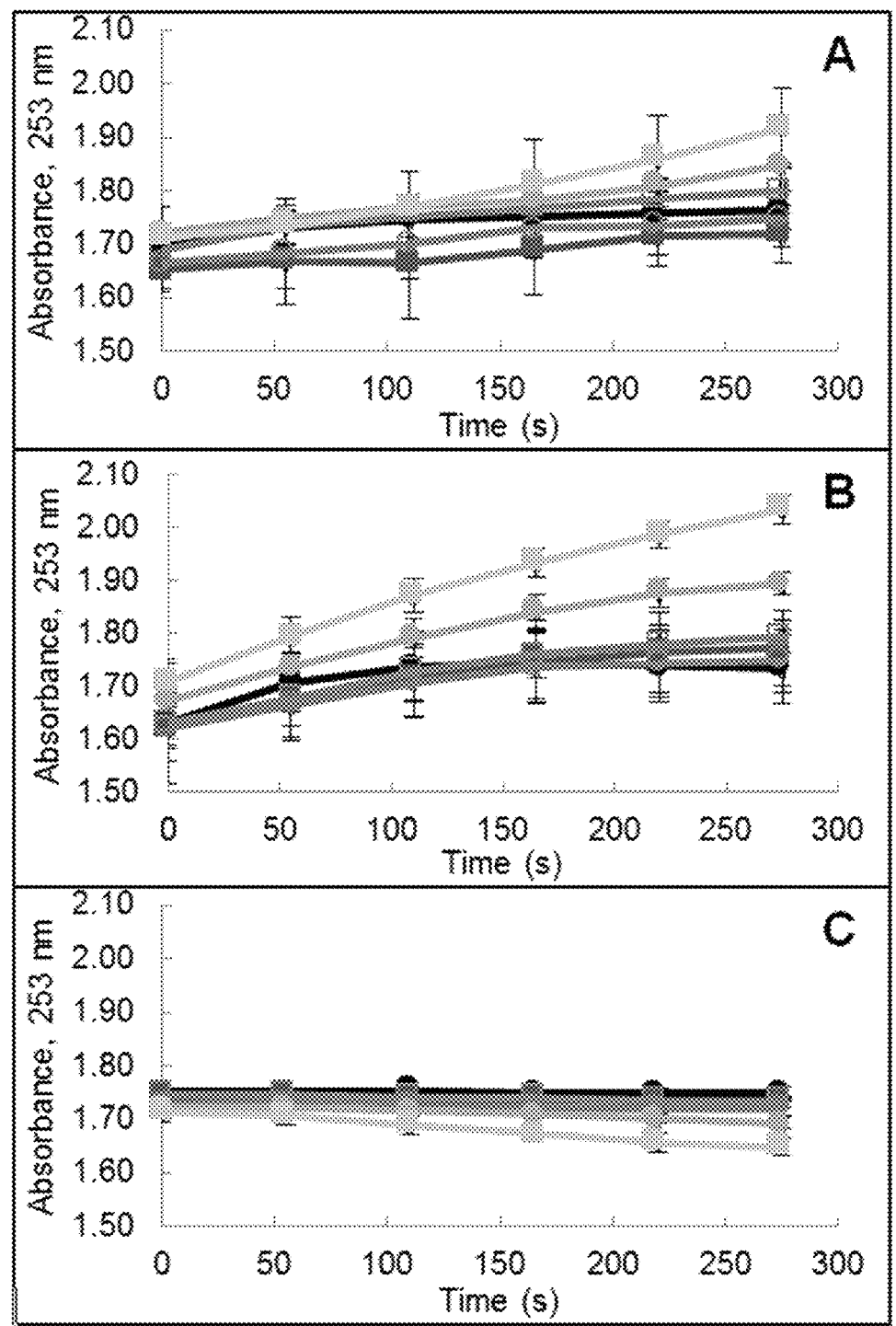
FIGS. 8A-8C: Activity assay of various trypsin concentrations incubated (FIG. 8A) without microgels (FIG. 8B) with 2 mg/ml P(MAA-co-NVP) microgels containing degradable crosslinks for 90 minutes, and (FIG. 8C) deactivated at 70° C. for 5 minutes (degradation at 37° C., pH 7.4, N=3). PBS (●), 0.0375 mg/ml trypsin (■), 0.075 mg/ml trypsin (○), 0.15 mg/ml trypsin (□), 0.3 mg/ml trypsin (●), and 0.6 mg/ml trypsin (■).

In a subsequent study, microgel concentration was held constant at 2 mg/ml while trypsin concentration was varied from 0.0375-0.6 mg/ml. As seen in FIG. 8A, the lowest two concentrations of trypsin solutions containing no microgels had final absorbance values below that of the control, PBS, indicating no appreciable trypsin activity. Therefore, it was expected that little degradation would occur at those concentrations. As expected, samples tested after 90 minutes of incubation of these trypsin solutions with microgels quickly reached a plateau during the activity assay, shown in FIG. 8B, confirming quenched trypsin activity. Trypsin concentrations of 0.3 and 0.6 mg/ml were sufficient to maintain enough trypsin activity to degrade peptide crosslinks in the microgels, as indicated by increasing absorbance over the 5 minute assay period. Further narrowing the range of trypsin concentrations, the activity assay was used to determine that trypsin concentrations down to 0.2 mg/ml maintained excess activity during degradation with microgels. FIG. 8C demonstrated that the trypsin activity was effectively quenched by incubation at 70° C. for 5 minutes.

As shown above, the trypsin activity was entirely quenched by reaction with proteins in the DMEM containing serum as indicated by negligible increase in absorbance from BAEE cleavage, shown in FIG. 7. This was desirable for subsequent exposure to cells in later studies, since trypsin can have a negative impact on cell metabolism and behavior. However, the microgel concentration was significantly diluted upon addition of the DMEM, necessitating highly concentrated particle solutions during degradation to achieve the desired final concentration.

Figures 9A, 9B:
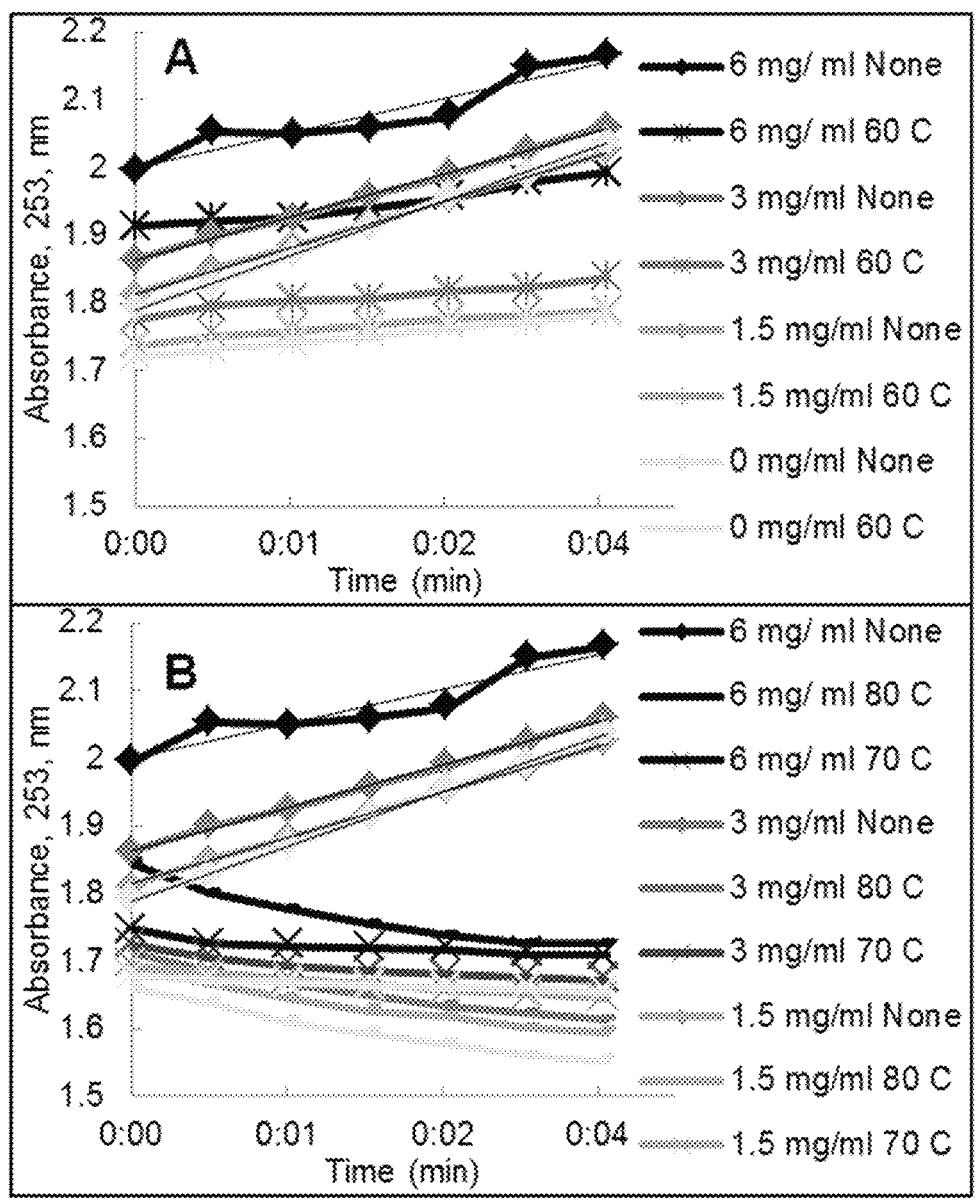
FIGS. 9A-9B: Activity assay of 0.6 mg/ml trypsin incubated with various concentrations of P(MAA-co-NVP) microgels containing degradable crosslinks for 90 minutes, and then deactivated with 5 minutes incubation at (FIG. 9A) 60° C.

According to the literature, a 5 minute incubation period in temperatures ranging from 60-80° C. should also be sufficient to deactivate the trypsin (Pace, 1930). Following the 90 minute degradation period in 0.6 mg/ml trypsin, samples at each microgel concentration were incubated at 60, 70, or 80° C. for 5 minutes. The BAEE trypsin activity assay indicated that samples incubated at 60° C. still contained some trypsin activity, as evidenced by the increase in absorbance over time shown in FIG. 9A. However, the rate of increase was still smaller than that of samples with active trypsin, with values ranging from only 16-26 a.u./min compared to 64-80 a.u./min. Samples incubated at higher temperatures of 70° C. and 80° C. for 5 minutes had negligible trypsin activity, shown by no absorbance increase in FIG. 9B. This method of deactivation was advantageous to the addition of DMEM, as microgels remained concentrated, requiring less starting material to reach the desired final concentration.

Cytotoxicity

Figures 10A, 10B:
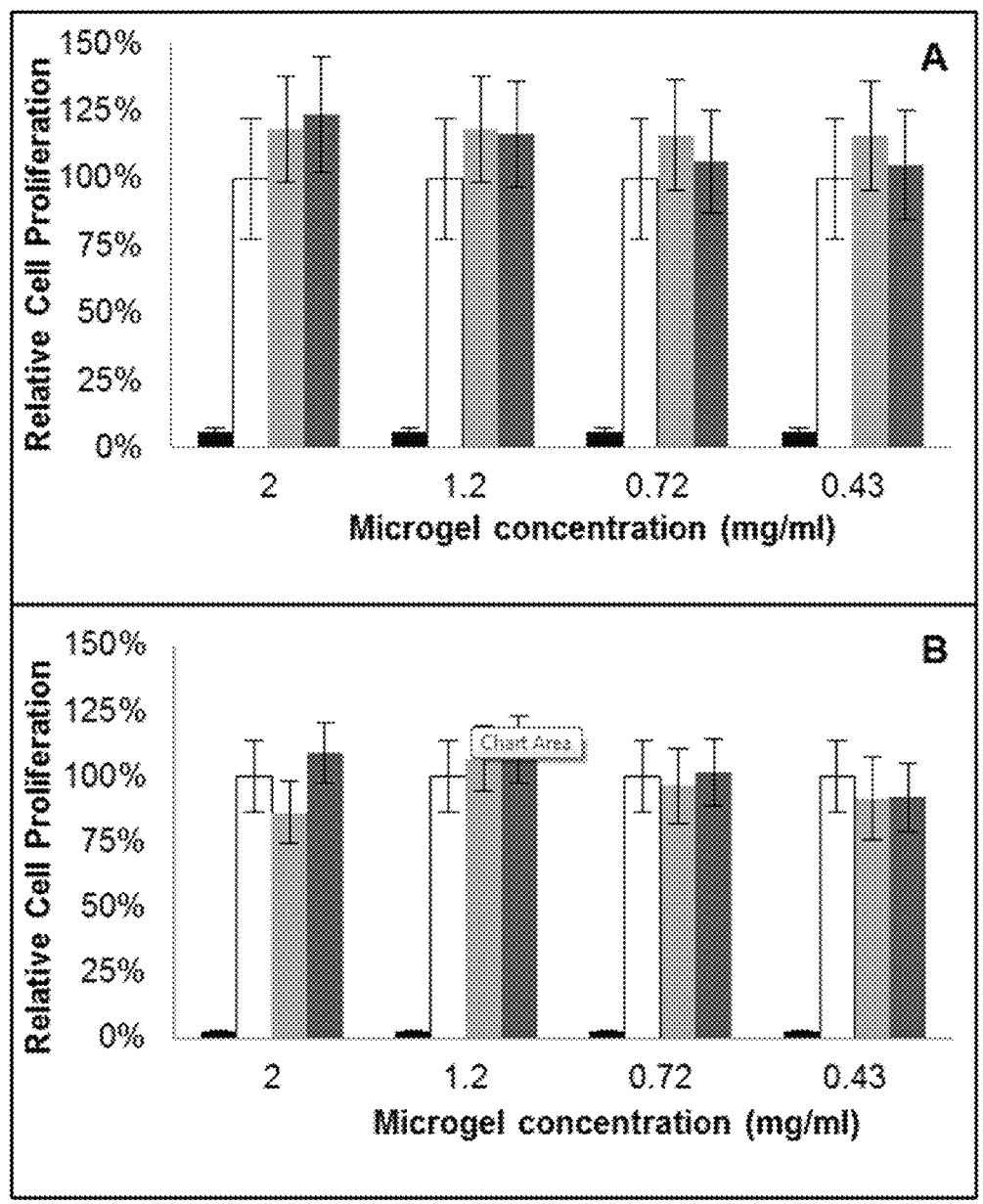
FIGS. 10A-10B: Evaluation of degraded microgel effect on cell metabolism using an MTS cell proliferation assay (Promega). Microgels were incubated in PBS or 1.2 mg/ml trypsin in PBS for 90 minutes at 37° C., and then the enzyme activity was quenched by addition of media with serum.

Cytotoxicity studies were performed with various microgel concentrations to find the maximum concentration that L929 murine fibroblast and RAW 264.7 murine macrophage cells could tolerate without disruption to metabolic activity. Microgels were incubated in 1.2 or 0.6 mg/ml trypsin solution for at least 4 hours to ensure degradation of the microgels; PBS buffer was used as a control. As trypsin can have negative effects on cell function (Kaplan and Bona, 1974), particularly the antigen-presenting ability of macrophages (Unanue, 1984), the trypsin was deactivated by the addition of excess cell media containing serum prior to exposure to cells. Cells were incubated with degraded microgel solutions for 8 hours to assess cytotoxic effect. FIG. 10A and FIG. 10B show L929 and RAW 264.7 cell proliferation, respectively, relative to that of cells incubated in normal media without microgels. Relative proliferation greater than 80% is considered acceptable in our evaluation. For all conditions and concentrations, cell proliferation is greater than 80% relative to the cells incubated in normal media. It was concluded that these degradation conditions and degradation products at these tested concentrations posed minimal cytotoxic effect to these two cell lines.

Insulin Loading

Insulin, a small therapeutic protein (~5.8 kDa), was chosen as a model therapeutic in loading and release studies since an oral delivery method for insulin has been widely investigated (Lowman et al., 1999; Kavimandan et al., 2006; Peppas and Kavimandan, 2006; Nakamura et al., 2004). Protein concentration was measured in the supernatant following the 4 hour loading period with microgels, then again in the supernatant following collapse of the microgels in 0.5 N HCl. Protein that was likely surface loaded was lost during the HCl wash. A significant amount of protein remained loaded following the HCl wash, indicating loading of the protein within collapsed microgels as opposed to surface loading. Loading efficiencies were calculated as follows, where $c_0$ is the initial protein concentration, $c_f$ is the final protein concentration, $mass_0$ is the initial mass of protein in solution, $mass_f$ is the final mass of protein in solution, and $mass_p$ is the mass of polymer in solution:

$$\text{Loading Efficiency} = \frac{c_0 - c_f}{c_0} * 100 \quad (6)$$

$$\text{Weight Loading Efficiency} = \frac{mass_0 - mass_f}{mass_0 - mass_f + mass_p} * 100 \quad (7)$$

Figure 11:
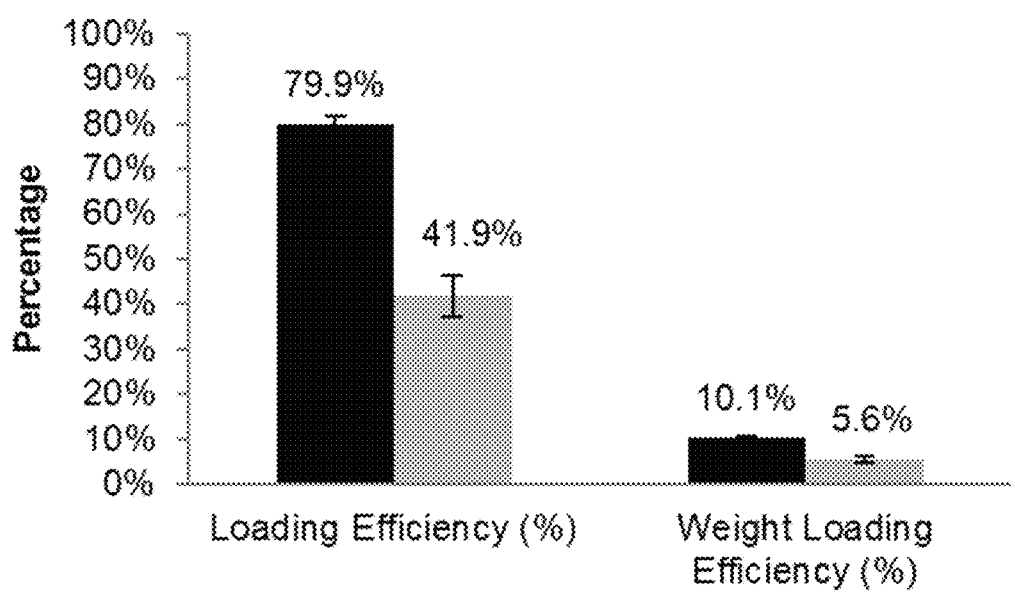
FIG. 11: Loading efficiencies of degradable P(MAA-co-NVP) microgels with peptide crosslinker after incubation in PBS (■) and after microgel collapse in acid (※). Insulin (MW 5.8 kDa) was loaded into the microgels. Loading efficiency was based on amount of protein into microgels relative to initial amount in solution. Weight loading efficiency is weight of loaded protein relative to total weight of microgel and protein. Microgels were loaded over 4 hours at 37° C. (N=3).
Figures 12A, 12B, 12C, 12D:
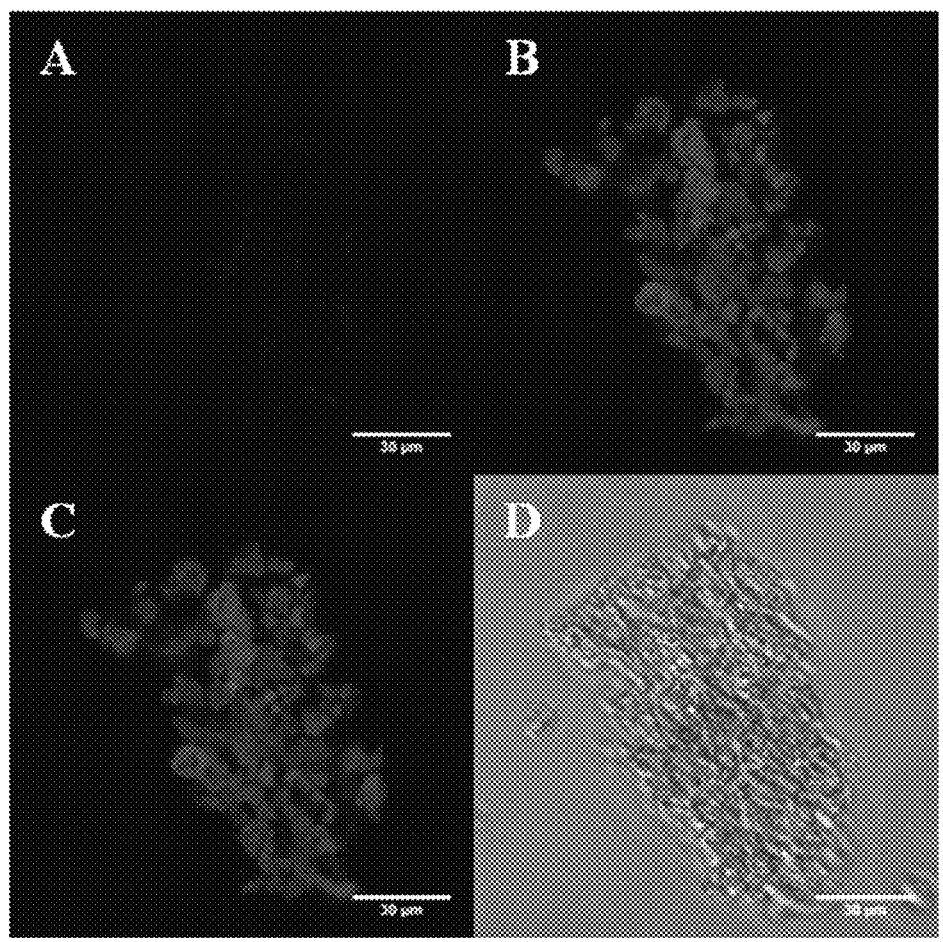
FIGS. 12A-12D: Image of P(MAA-co-NVP) microgel crosslinked by degradable peptide and encapsulating polycationic nanogels taken by confocal laser scanning microscopy.

The overall loading efficiency of the insulin after collapse of the particles, shown in FIG. 11, was ~41% and the weight loading efficiency of insulin was 5.6%. These loading and weight efficiencies were comparable to those reported for similar hydrogel systems with large proteins (Wong et al., 2014; Liang et al., 2014).

As shown by the data above, synthesis of the linear polymer and crosslinked hydrogels was greatly affected by pH of the respective reaction solutions. The crosslinking reaction was most successful using linear polymer lyophilized at pH 8 in a two-part EDC-NHS linking reaction transitioned from pH 5 to pH 8. Incorporation of the peptide was consistently above 97% as determined by fluorescamine assay of the peptide remaining in solution, and incorporation was verified by IR spectra.

Proteolytic degradation of the peptide crosslinks upon incubation with trypsin solutions, SIF, and rat intestinal fluid was demonstrated by reduced relative turbidity as a function of time and trypsin concentration. In contrast, relative turbidity of the microgel solutions remained constant upon incubation in PBS, SGF, and rat gastric fluid, verifying that the microgels were not susceptible to degradation by the gastric enzyme pepsin. The degradable microgels induced negligible cytotoxic effects, even at high concentration, in both the degraded and nondegraded states. These studies confirm the biodegradable behavior of the peptide crosslinked hydrogel is highly suitable for intestinal delivery applications.

The P(MAA-co-NVP) polymer backbone demonstrated pH responsive behavior, swelling at neutral conditions and collapsing at low pH gastric conditions. The microgels were able to efficiently load the therapeutic protein insulin and retain the loaded protein in low pH conditions. These data show that the enzymatic response, relevant degradation timescale, and high biocompatibility of this biodegradable microgel system. Based on these data, this microgel system may be effectively used as a vehicle for oral delivery of therapeutics, including relatively delicate proteins such as, e.g., insulin.

Example 2

Biodegradable Microencapsulated Nanogels for Orally Delivered siRNA

Materials
Chemicals

Methacrylic acid (MAA), N-vinyl pyrrolidone (NVP), and Irgacure 184® (1-hydroxy-cyclohexyl-phenylketone) were obtained from Sigma-Aldrich (St. Louis, Mo.). 1-ethyl-3-(3-dimethylaminopropyl) carbodiimide hydrochloride (EDC) was obtained from Sigma Aldrich. N-hydroxysuccinimide (NETS) was obtained from Pierce Biotechnology, Inc. (Rockford, Ill.). The custom sequence oligopeptide GRRRGK (SEQ ID NO: 1) was synthesized by CHI Scientific (Maynard, Mass.). All reagents were used as received. Purified pepsin from porcine gastric mucosa (≥2500 U/mg), pancreatin from porcine pancreas (4×USP specifications), Trypsin-EDTA solution (1×) and Nα-benzoyl-L-arginine ethyl ester hydrochloride (BAEE) trypsin substrate were obtained from Sigma-Aldrich. 4-Chloro-7-nitrobenzofurazan (NBD-Cl, 98%) was obtained from Acros Organics (Geel, Belgium). All other solvents and buffers were purchased from Fisher Scientific (Waltham, Mass.). Polycationic 2-(diethylamino)ethyl methacrylate-based nanogels (~100 nm diameter) were synthesized by Forbes et al, 2013 and tagged with a fluorescent molecule, NBD-Cl, by Forbes et al., 2014.

Synthesis and Purification

Synthesis of Linear Polymer:

P(MAA-co-NVP) linear polymer was synthesized by photoinitiated, free-radical polymerization. MAA and NVP were added at a 1:1 molar ratio to a 1:1 (w/w) deionized water and ethanol solution to yield a 1:3 (w/w) total monomer to solvent ratio. Photoinitiator Irgacure 184 was added at 1 wt % with respect to total monomer weight.

The mixture was homogenized by sonication then the round bottom flask was sealed with a rubber septum. The solution was purged with nitrogen for 20 minutes, then the reaction was initiated with a Dymax BlueWave® 200 UV point source (Dymax, Torrington, Conn.) at 100 mW/cm$^2$ intensity and allowed to polymerize for 30 minutes while stirring.

Following polymerization, the linear polymer was purified from unreacted monomer by addition of 1 N hydrochloric acid (HCl) to precipitate polymer, centrifugation, and resuspension in deionized water. After 3 wash cycles, the polymer solution was frozen in liquid nitrogen ($LN_2$) and lyophilized for at least 24 hours.

Synthesis of Peptide Crosslinked Gels:

Linear P(MAA-co-NVP) was dissolved in a 1:1 (v/v) water:ethanol solution at a concentration of 50 mg/ml. EDC was dissolved in ethanol at a concentration of 50 mg/ml and NHS was dissolved in ethanol at a concentration of 16 mg/ml. The EDC and NHS solutions were added to the polymer solution at a ratio of 6:3:1 polymer:EDC:NHS by weight. The solution was mixed by vortex briefly, then allowed to react for ~3 min with shaking. Polycationic nanoparticles in a 10 mg/ml solution in ethanol were added at 10 wt % relative to the P(MAA-co-NVP) and the solution was briefly mixed by vortex. The pH was raised to ~8 by the addition of 1 N sodium hydroxide (NaOH), and then a volume of 100 mg/ml peptide in ethanol solution was added to achieve a 2:1 weight ratio of polymer:peptide. The mixture was allowed to react overnight with shaking then purified by 3 wash cycles with water and centrifugation at 10,000×g for 5 minutes. Following the washes, the polymer was frozen in $LN_2$ and lyophilized for at least 24 hours.

After lyophilization, the polymer was milled into a fine power by crushing with mortar and pestle. The powder was sifted to the size ranges of 30-75 μm and less than 30 μm by ultraprecision ASTM sieves (Precision Eforming, Cortland, N.Y.).

Cell Culture:

Human colon adenocarcinoma Caco-2, murine fibroblast L929, and murine macrophage RAW 264.7 cells obtained from American Type Culture Collection (ATCC, Rockwell, Md.). All cell lines were cultured in Dulbecco's modified Eagle medium (DMEM) (Mediatech, Herndon, Va.) supplemented with 10% heat-inactivated HyClone™ Fetal Bovine Serum, USDA Tested (Fisher Scientific), 1% 200 mM L-glutamine solution (Mediatech), 100 U/ml penicillin, and 100 μg/ml streptomycin (Mediatech). Cytotoxicity studies were performed using DMEM without phenol red supplemented with 2% heat-inactivated HyClone™ Fetal Bovine Serum, USDA Tested (Fisher Scientific), 1% non-essential amino acids (Mediatech), 100 U/ml penicillin, and 100 μg/ml streptomycin (Mediatech) or OptiMEM® reduced serum media (no phenol red) (Life Technologies, Grand Island, N.Y.). Transfection studies were completed in OptiMEM® reduced serum media (no phenol red). Cells were incubated at 37° C. in a 5% $CO_2$ environment.

In Vitro Cytotoxicity Study:

Cells were seeded at a density of 10,000 cells/well in a 96-well plate and allowed to incubate for 24 hours prior to the experiment. Microgels were degraded in 0.3-1.25 mg/ml trypsin in phosphate buffered saline (PBS) at concentrations ranging from 1.3-6 mg/ml. Degradation took place at 37° C. with shaking for 90 minutes or 4 hours. Trypsin was deactivated by addition of 2× volume DMEM without phenol red containing 2% fetal bovine serum or by incubation at 70° C. for 5 minutes. Cells were incubated with degraded microgels for 18 hours at 37° C. and 5% $CO_2$. The cytotoxic effect of the microgels was evaluated using a CellTiter 96® Aqueous One Solution Cell Proliferation MTS Assay or a CytoTox-ONE™ Homogeneous Membrane Integrity Assay (Promega, Madison, Wis.). In the case of the proliferation assay, MTS was added to the wells and incubated for 90 minutes at the same conditions before absorbance measurements were made at 490 nm using a Bio-Tek Synergy™ HT multi-mode plate reader (Winooski, Vt.). In the case of the membrane integrity assay, 50 μl of the cell media from each well was combined with 50 μl of the assay solution in a black-walled 96-well plate, incubated at room temp for 10 minutes, then the fluorescence was measured at 530/560 (sensitivity=60) using a Bio-Tek Synergy™ HT multi-mode plate reader (Winooski, Vt.). Cytotoxicity is reported as 'relative cell proliferation' using the MTS assay and 'percent viability' using the membrane integrity assay.

siRNA Loading:

Microgels containing NBD-labeled nanogels were loaded by equilibrium partitioning post-synthesis with Silencer® Select Negative Control No. 1 (Life Technologies), AllStars Mm/Rn Cell Death Control siRNA, AllStars Hs Cell Death Control siRNA, Negative Control siRNA (Qiagen, Hilden, Germany), or fluorescently labeled DyLight 647-labeled siRNA (Sense: DY647-UAAGGCUAUGAAGA-GAUACUU (SEQ ID NO: 51); Thermo Scientific, Lafayette, Colo.). Microgels were incubated at a concentration of 12 mg/ml at 37° C. for 1.5 hours in a 400 nM or 100 nM siRNA solution in nuclease-free PBS at pH ~5.5. Nuclease free 10×PBS was prepared by dissolving sodium chloride, potassium chloride, monobasic potassium phosphate, and sodium phosphate dibasic heptahydrate in water, treating with 0.1% v/v diethylpyrocarbonate (DEPC) overnight, and then autoclaving to remove DEPC. The microgels were collected by centrifugation at 10,000×g for 5 minutes. The loaded microgels were stored at −20° C. until further studies. siRNA loading was evaluated by Quant-iT™ RiboGreen® RNA Assay Kit (Invitrogen).

Microgel Degradation:

Microgels were degraded at various trypsin concentrations ranging from 0.2-1.2 mg/ml in 1× phosphate buffered saline solution (pH 7.4), simulated gastric fluid, simulated intestinal fluid, rat gastric fluid or rat intestinal fluid.

Simulated gastric fluid (SGF) and simulated intestinal fluid (SIF) were prepared according to USP 29 (Pharmacopeia, 2006). Briefly, SGF was prepared by dissolving 2 g of sodium chloride and 3.2 g of purified pepsin from porcine stomach mucosa was dissolved in 800 ml deionized water. 7 ml of HCl was added, followed by enough water to make up to 1 L and the pH adjusted to 1.2. SIF was prepared by dissolving 6.8 g monobasic potassium phosphate in 250 ml deionized water, then 77 ml of 0.2 N NaOH was added while stirring. 500 ml additional water was added then 10 g pancreatin was mixed into the solution. The pH was adjusted to 6.8 using 0.2 N NaOH or HCl then the solution was made up to 1 L with water.

Gastrointestinal fluids were harvested from Sprague Dawley juvenile male rats (250-300 g) according to a protocol published by Yamagata et al. with some modifications (Yamagata et al., 2006). Briefly, after sacrificing the rat the stomach was excised and ligated at both ends. A needle was inserted to inject 5 ml of pH 1.2 HCl—NaCl buffer (same as SGF minus pepsin) and the gastric contents were collected in a 50 ml centrifuge tube. Similarly, a ~20 cm section of the upper small intestine was cannulated and flushed twice with 10 ml cold PBS (1×, pH 7.4). The fluid was collected as intestinal fluid in a 50 ml centrifuge tube. Both the harvested fluids were centrifuged at 3,200×g, 4° C., for 15 min to separate solids from the fluids. The supernatants were retained as rat gastric fluid and rat intestinal fluid, respectively. Protein content of the fluids was measured using a NanoDrop 1000 spectrophotometer (Thermo Scientific, Wilimington, Del.). Fluids were stored at −20° C. until use.

Degradation was evaluated by measuring relative turbidity of the samples over time, as reported by Klinger and Landfester (Klinger and Landfester, 2012). Microgels were suspended in trypsin solutions of varying concentration, PBS, SGF, SIF, or rat gastrointestinal fluids at various concentrations. 100 µl of each solution was added to a 96-well plate in triplicate, and the absorbance was measured at 500 nm in 5 minute intervals over 90 minutes using a Bio-Tek Synergy™ HT multi-mode plate reader (Winooski, Vt.). The temperature was controlled at 37° C. and the plate underwent shaking for 3 seconds before each measurement.

Activity of the trypsin following incubation with particles and deactivation methods including addition of serum-containing cell culture media and 5 minutes incubation at 70° C. was evaluated using a trypsin activity assay adapted from the protocol by Yanes et al. (Yanes et al., 2007). Briefly, degradation supernatant was combined with 1 mg/ml BAEE in PBS at a 1:9 sample:BAEE ratio by volume. Immediately after addition of the BASE, absorbance at 253 nm was measured at the minimum interval (typically 40-50 seconds) for 5 minutes using a Bio-Tek Synergy™ HT multi-mode plate reader (Winooski, Vt.).

Evaluation of siRNA Stability by Polyacrylamide Gel Electrophoresis:

For polyacrylamide gel electrophoresis, samples were degraded in trypsin concentrations from 0.3-1.2 mg/ml for 90 min then the trypsin was deactivated with DMEM or heat. Samples were also incubated in rat gastric fluid, rat intestinal fluid, PBS, or SGF to determine release and stability of siRNA. Competitive polyanion assays were completed using solutions of heparin sodium salt from porcine intestinal mucosa (Sigma-Aldrich) to competitively complex with the polycationic nanogels and promote siRNA dissociation from the nanogels. Ribonuclease A from bovine pancreas (RNAse A) (Sigma-Aldrich) was used as a positive degradation control; siRNA was incubated in a 0.05 mg/ml RNAse A solution for 90 minutes at 37° C. Samples were diluted 1:1 by volume with Novex® TBE-urea sample loading buffer (2×) (Life Technologies), denatured at 70° C. for 3 min, and loaded into a Novex® TBE-urea denaturing polyacrylamide gel with 15% crosslinking (Life Technologies). The gel was run at constant 180V for 70 min in 1× Novex® TBE running buffer (Life Technologies). Following the run, the gel was stained with SYBR green II (Sigma-Aldrich) diluted 1:10,000 by volume in 1×TBE running buffer for 30 minutes with shaking, the gel was rinsed with DI water for 5 minutes with shaking, and then the gel was imaged with a Typhoon 9500 fluorescent imager using the SYBR green II filter, 50 µm pixel size, 500 pmt. (GE Life Sciences, Pittsburgh, Pa.).

Confocal Microscopy:

Microgels were fluorescently labeled with TAMRA-cadaverine (Biotium) via EDC-NHS reaction. Briefly, 15 mg microgels were mixed with 1.25 mg of EDC and 1.25 mg NHS in 0.1 M MES buffer at pH 4.7. After a ~3 minute incubation period at room temperature, 15 µl of 0.5 mg/ml TAMRA-cadaverine solution was added and allowed to react for 2 hours at room temperature. The polymer was washed 5× by centrifugation at 10,000×g for 5 minutes and resuspension in 1 ml DI water to remove unreacted fluorophore. The final wash was left overnight to allow the polymer to fully swell. The microgels were centrifuged again, the supernatant removed, and the remaining polymer flash-frozen in $LN_2$ followed by lyophilization. Fluorescent microgels were incubated in PBS or trypsin at a concentration of 2 mg/ml for 90 minutes. Slides were prepared by mounting 10 µl of particle solution on slides with ProLong® gold antifade reagent.

For cell uptake studies, coverslips (18 mm round, no. 1.5 thickness) were acid-washed overnight with 1 N HCl at 60° C., rinsed with ethanol/water mixtures with successively increasing volume ratios of ethanol, and then the coverslips were placed in a 12-well plate. RAW 274.6 cells were seeded in the wells at a density of 115,000 cells/well. Microgels containing NBD-labeled nanogels, with or without fluorescently labeled DY647 siRNA, were degraded at a concentration of 2.5 mg/ml in 0.6 mg/ml trypsin for 60 minutes then incubated at 70° C. for 5 minutes to deactivate trypsin. 24 hours after plating the cells, the media was aspirated and replaced with 0.4 ml OptiMEM and 0.1 ml of degraded microgel solution. Lipofectamine 2000 (Life Technologies) loaded with fluorescently labeled DY647 siRNA was used as a positive control for siRNA delivery. Cells were incubated with the particles or Lipofectamine 2000 for 18 hours.

After the incubation period, the media was aspirated and the cells were washed 3× with cold Dulbecco's phosphate buffered saline (DPBS, Sigma-Aldrich), fixed with cold IC fixation buffer containing 4% paraformaldehyde (Life Technologies), and washed 3× wish cold Hyclone™ Hank's balanced salt solution (HBSS, Fisher Scientific). In some cases, the cell membrane was stained with 1 µg/ml AlexaFluor® 594 conjugated wheat germ agglutin (Life Technologies) for 10 minutes then washed 2× with cold HBSS and once with cold, sterile DI water. ProLong® gold antifade reagent with or without DAPI stain (Life Technologies) was used to mount the coverslips on acid-washed slides. Slides were stored at −4° C. until imaging.

Slides were imaged with Zeiss LSM 710 confocal microscope with 40×- and 63×-oil objectives. Sequential scanning was used to eliminate emission bleed-though between channels. The pinhole was set to 1 AU in the green channel. The gain and offset for each channel were set using single stain controls, and were kept constant for the full series of images to allow image comparisons. Images were collected in 8 bit format with an average=4 to reduce noise, and all images underwent identical postprocessing ($\gamma=0.7$ for red, blue, and green channels, $\gamma=0.1.3$ for bright-field).

ImageStream Flow Cytometry:

Microgels containing NBD-labeled nanogels and were incubated in PBS (pH 7.4) or 0.6 mg/ml trypsin solution at 1.5 mg/ml for 60 min then the trypsin was deactivated by incubation at 70° C. for 5 minutes. Analysis of nanogel distribution and microgel degradation was conducted using Amnis ImageStream (Seattle, Wash.) imaging flow cytometer. Nanogels were excited with a 488 laser and detected in channel 2 (505-560 nm) and bright field images were collected in channel 4 (595-660 nm). At least 10,000 events were collected for analysis. Out-of-focus particles and debris were excluded from the analysis by gating the Gradient RMS feature in IDEAS® software; typically, events with Gradient RMS value<50 were considered out of focus. Fluorescence intensity in the green channel was gated to intensity values>3000.

Cell Transfection:

RAW 264.7 cells were seeded at 10,000 cells/well in 96-well cell culture plates for transfection studies. The RAW 264.7 cells were allowed to incubate approximately 48 hours and the Caco-2 cells approximately 24 hours, until they reached a confluence of about 50%.

After the appropriate cell growth period, microgels were loaded with siRNA for transfection studies using the same conditions described in Section 7.2.4. Microgels were loaded with AllStars Mm/Rn Cell Death Control siRNA, AllStars Hs Cell Death Control siRNA, or Negative Control siRNA at a loading concentration of 400 nM. Microgels were degraded at a concentration of 3.5 or 2 mg/ml in 0.3 mg/ml trypsin in PBS at 37° C. for 90 minutes. Nanoparticles were complexed with siRNA (AllStars Mm/Rn Cell Death Control siRNA, AllStars Hs Cell Death Control siRNA, or Negative Control siRNA) in 1×PBS pH 5.5 at 0.125 mg/mL nanoparticles and 400 nM siRNA for ~15 prior to addition to cells. siRNA (400 nM) was incubated with 2 μl Lipofectamine 2000 (positive control) in 78 μl OptiMEM for ~15 minutes prior to addition to cells.

The microgels were added to cells at a final concentration of 0.7 and 0.4 mg/mL in OptiMEM, nanoparticles were added to cells at a final concentration of 0.025 mg/ml in OptiMEM, and the Lipofectamine 2000 loading solution was added to cells at a 1:5 dilution in OptiMEM. Cells were incubated with particles for 48 hours, at which point the media was removed by aspiration and replaces with Cell-Titer 96® Aqueous One Solution Cell Proliferation MTS Assay (Promega). Cells were incubated with MTS solution for 90 minutes, and the absorbance at 490 and 690 nm was measured with a Bio-Tek Synergy™ HT multi-mode plate reader (Winooski, Vt.). The viability results for the AllStars Death and the Negative Control siRNA were compared by Student's t test (two-tailed, unequal variance) to check for statistically significant silencing. The silencing efficiency was evaluated using the absorbance of cells with death siRNA and cells with negative control siRNA as shown in Eq. 7.1:

$$\text{silencing efficiency} = 100 \times \left(1 - \frac{A_{Death}}{A_{Negative}}\right) \qquad 7.1$$

Results

P(MAA-co-NVP) was synthesized and crosslinked with peptide as described in Example 1, the only difference being the addition of polycationic nanogels prior to the addition of the peptide. The polycationic nanogels were added at 10 wt % with respect to polymer weight and appeared brown in color due to the conjugated fluorophore NBD-Cl. Prior to use in the microgels, NBD-Cl was reacted in excess to primary amines present in the nanogels to serve a dual purpose; first, to impart fluorescent detection of the nanogels, and second, to protect the primary amines from reacting during the EDC-NHS reaction with the peptide crosslink.

Upon addition of the peptide, the mixture was immediately turbid and precipitation of brown, crosslinked hydrogel was evident. After the reaction was complete, the hydrogel was washed by repeated centrifugation and resuspension in DI water to remove impurities. The supernatant was retained from each wash to determine the incorporation efficiency of the nanogels. Following the washes, the hydrogel was frozen in $LN_2$ and lyophilized. The dry product appeared as fluffy brown chunks, and was easily crushed into a powder consisting of particles <30 μm in size.

Incorporation of Polycationic Nanogels

The fluorescence of the nanogels in the wash supernatant was measured using a Bio-Tek Synergy™ HT multi-mode plate reader and compared to the fluorescence values of known concentrations of nanogels. It was determined that 30-40% of the nanogels were incorporated into the hydrogel, bringing the final weight ratio to 3-4% with respect to the polymer weight.

Figure 13:
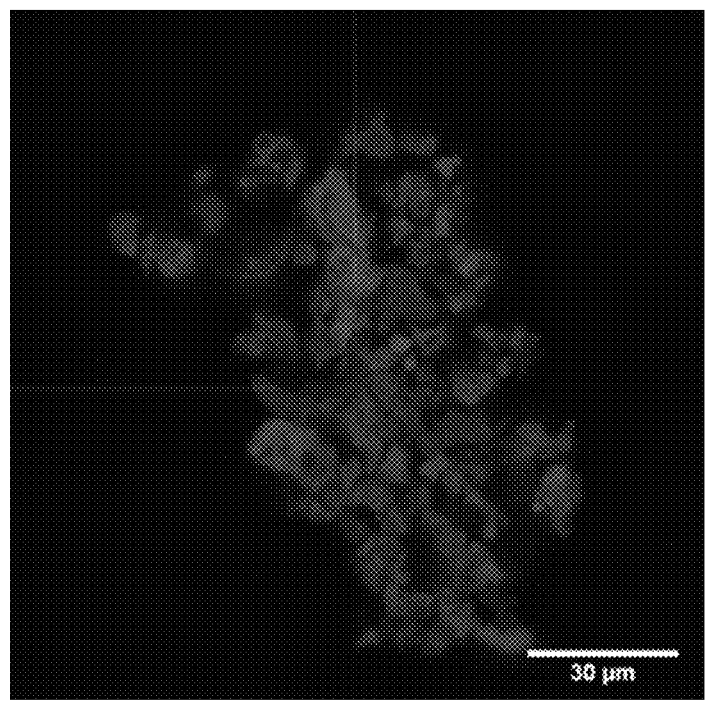
FIG. 13: Orthogonal view of Z-stack image of P(MAA-co-NVP) microgel crosslinked by degradable peptide and encapsulating polycationic nanogels taken by confocal laser scanning microscopy. Nanogels labeled with NBD-Cl (green) in P(MAA-co-NVP) microgel matrix labeled with TAMRA-cadaverine (red). (Scale bar=30 μm)

Incorporation of the polycationic nanogels was visualized using confocal laser scanning microscopy. The hydrogel particles were labeled with a TAMRA fluorophore that was reactive to carboxylic acid functional groups on the P(MAA-co-NVP). After purification, the particles were lyophilized and a known weight was resuspended in PBS (pH 7.4). Slides were prepared by dropping the particle solution onto a slide and fixing the coverslips with ProLong® gold antifade reagent. Imaging of the particles confirmed the presence of the nanogels (green) within the P(MAA-co-NVP) particles (red), as seen in FIGS. 12A-D. The porous structure of the hydrogels was also discernible in the bright field image, in FIG. 12D. A Z-stack image, FIG. 13, was obtained to verify the distribution of nanogels throughout the particle. Though the nanogels were throughout the particle, they did tend to be present in clusters or pockets, which is consistent with the method of crosslinking.

Degradation of Microgels with Nanogels

Figure 14:
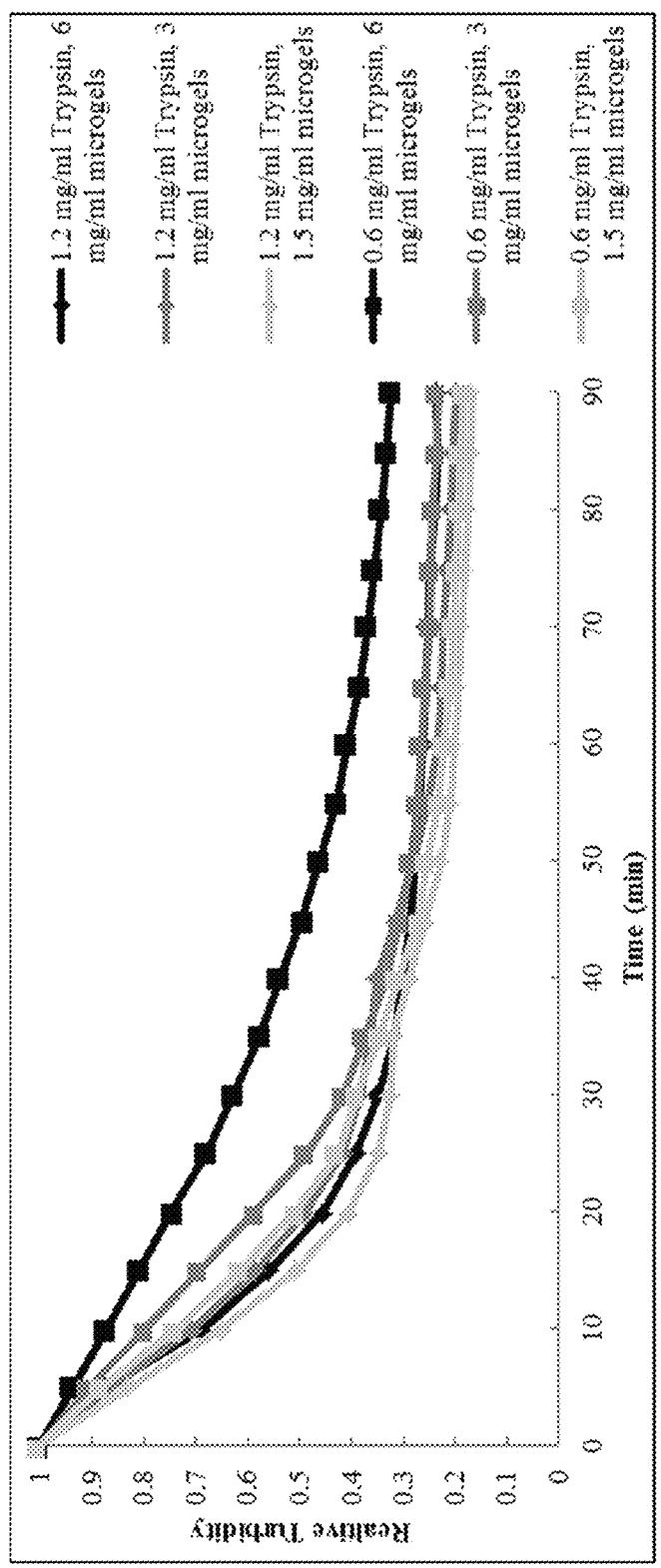
FIG. 14: Relative turbidity over time of various concentrations of P(MAA-co-NVP) microgels with degradable crosslinks encapsulating nanogels during incubation in 0.6 and 1.2 mg/ml trypsin in PBS (37° C., pH 7.4, N=3).

Degradation studies with SIF, SGF, trypsin, and PBS were completed to verify that incorporation of the nanogels did not affect degradation kinetics. As observed in hydrogels without nanogels, the turbidity of the particle solutions could be used as a measure of degradation over time. FIG. 14 shows the decrease in turbidity over time of 1.5-6 mg/ml microgels in 0.6 or 1.2 mg/ml trypsin. All concentrations plateaued at the lowest turbidity value within 90 minutes, which was approximately the same as microgels containing no nanogels. Therefore, it does not seem as if the nanogels significantly affect the degradation kinetics. However, as the relative turbidity plateaued at values of 18% and higher, it is possible that the nanogels prevent complete degradation of the microgels. This may be attributed to the reaction of some of the amine groups present in the nanogels during the EDC-NHS crosslinking reaction, effectively incorporating the nanogels as nondegradable crosslinks within the gel. While this is an undesirable side reaction that reduces the number of nanogels able to be released from the microgels, it is thought to be limited by the protection of the amine groups via NBD-Cl and is not prevalent enough to affect the ability of the microgels to degrade.

Figures 15A, 15B:
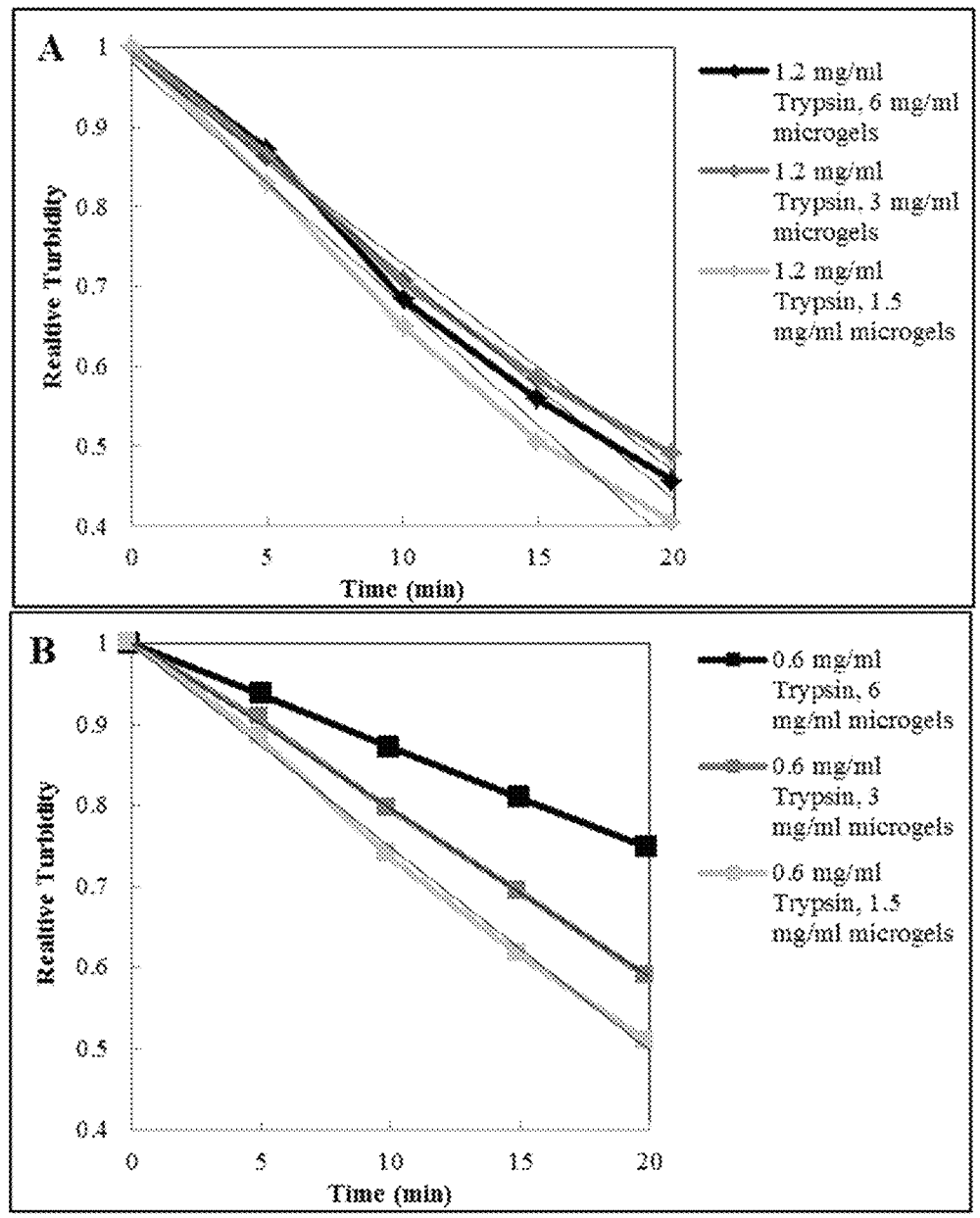
FIGS. 15A-15B: Relative turbidity over the first 20 minutes of incubation of trypsin with various concentrations of P(MAA-co-NVP) microgels with degradable crosslinks encapsulating nanogels.
Figure 16:
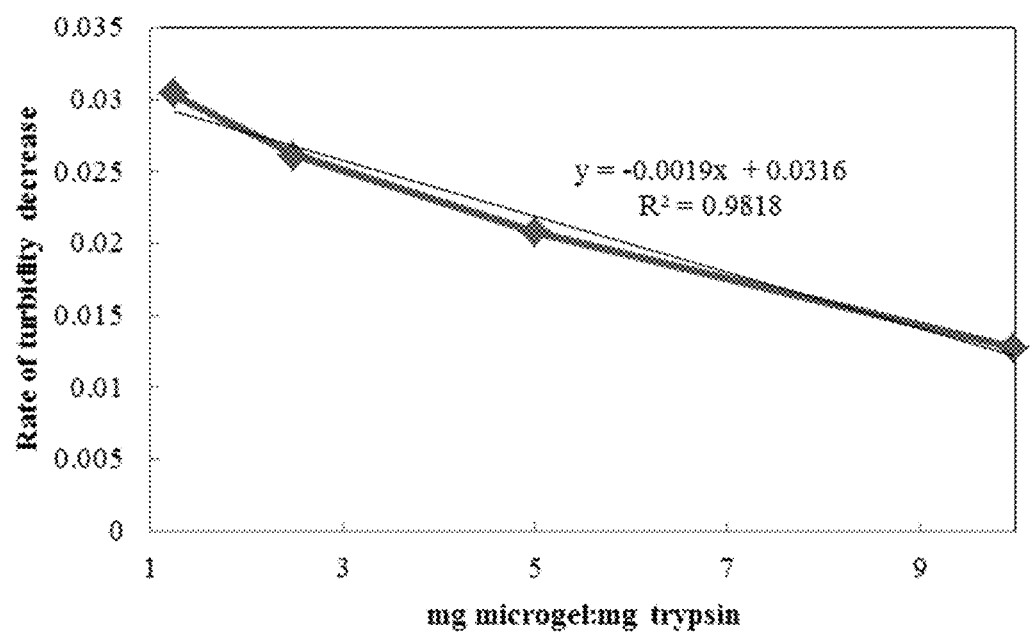
FIG. 16: The microgel:trypsin weight ratio versus initial rate of turbidity decrease was correlated with a linear fit ($R^2$=0.98). The relationship may be used to approximate degradation time of a known microgel:trypsin weight ratio.

It was further noted that the initial change in turbidity over the first 20 minutes of exposure to trypsin was linear, as shown in FIG. 15A (1.2 mg/ml trypsin) and FIG. 15B (0.6 mg/ml trypsin). The corresponding microgel to trypsin ratio versus initial rate of turbidity decrease values were then plotted to determine the relationship. The fit was nearly linear, as shown in FIG. 16 ($R^2$=0.98), and may be used to approximate degradation time of a known microgel to trypsin weight ratio.

Figures 17A, 17B:
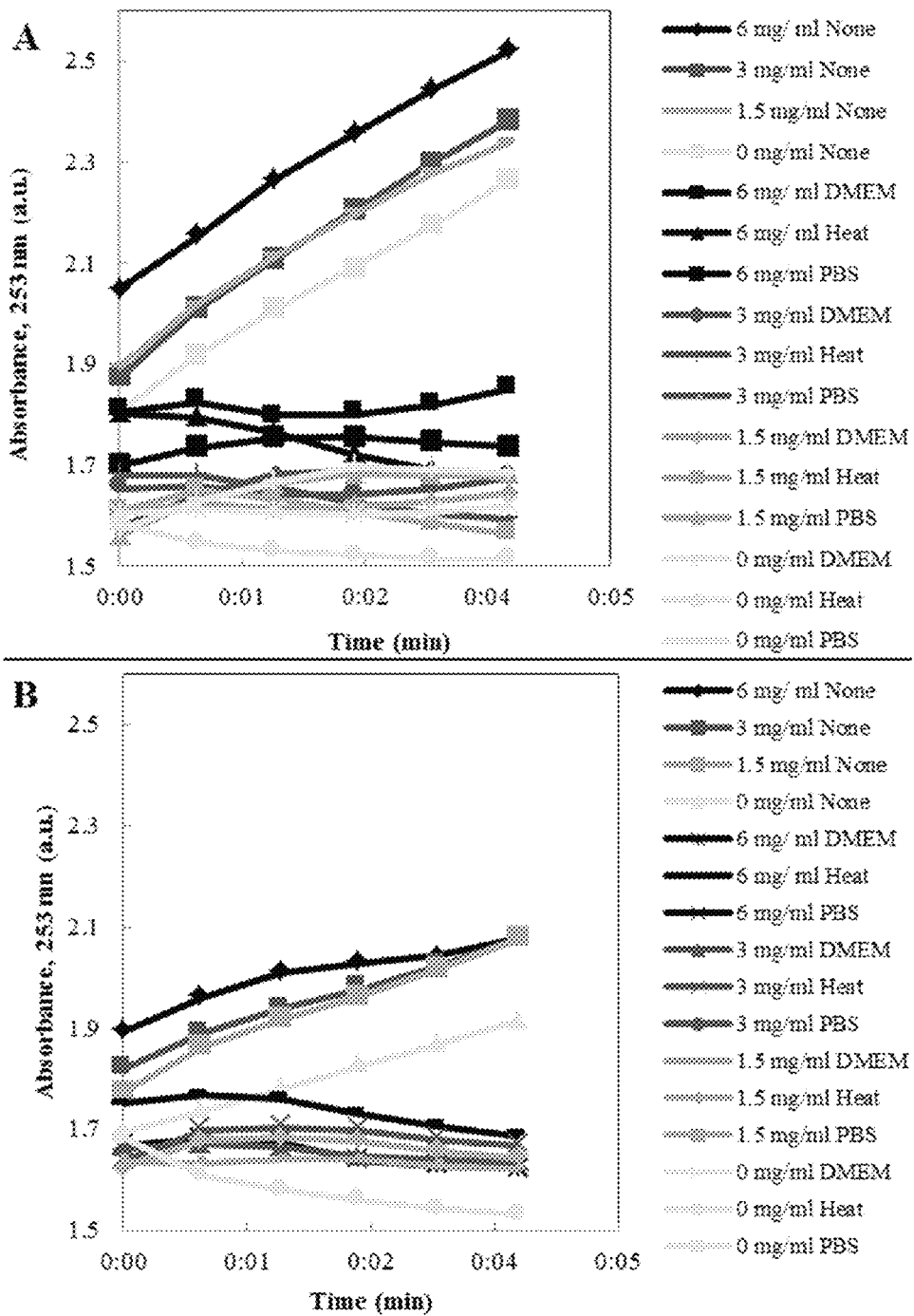
FIGS. 17A-17B: BAEE activity assay of FIG. 17A, 1.2 mg/ml trypsin.

Additionally, trypsin activity assays with BAEE were performed to ensure the quenching of trypsin activity prior to exposure to cells. Microgels were incubated with 1.2 mg/ml or 0.6 mg/ml trypsin in pH 7.4 PBS for 90 minutes at 37° C., and then subjected to deactivation by incubation at 70° C. for 5 minutes or addition of 2x volume DMEM containing serum. FIG. 17A shows the complete deactivation of 1.2 mg/ml trypsin by both heat and DMEM compared unadulterated trypsin solutions, and FIG. 17B shows the same for 0.6 mg/ml trypsin solutions. Therefore, it was concluded that either was a satisfactory method of deactivating trypsin at concentrations at and below 1.2 mg/ml.

As further confirmation of nanogel incorporation as well as visualization of degradation on the micro-scale, microgels in various solutions were imaged with ImageStream flow cytometry. This equipment enabled the analysis of entire populations of microgels using parameters such as fluorescence intensity in a particular channel or particle size as detected by bright field imaging. It allowed real-time imaging and quantification of the change in particle size distribution during degradation.

Figures 18A, 18B, 18C:
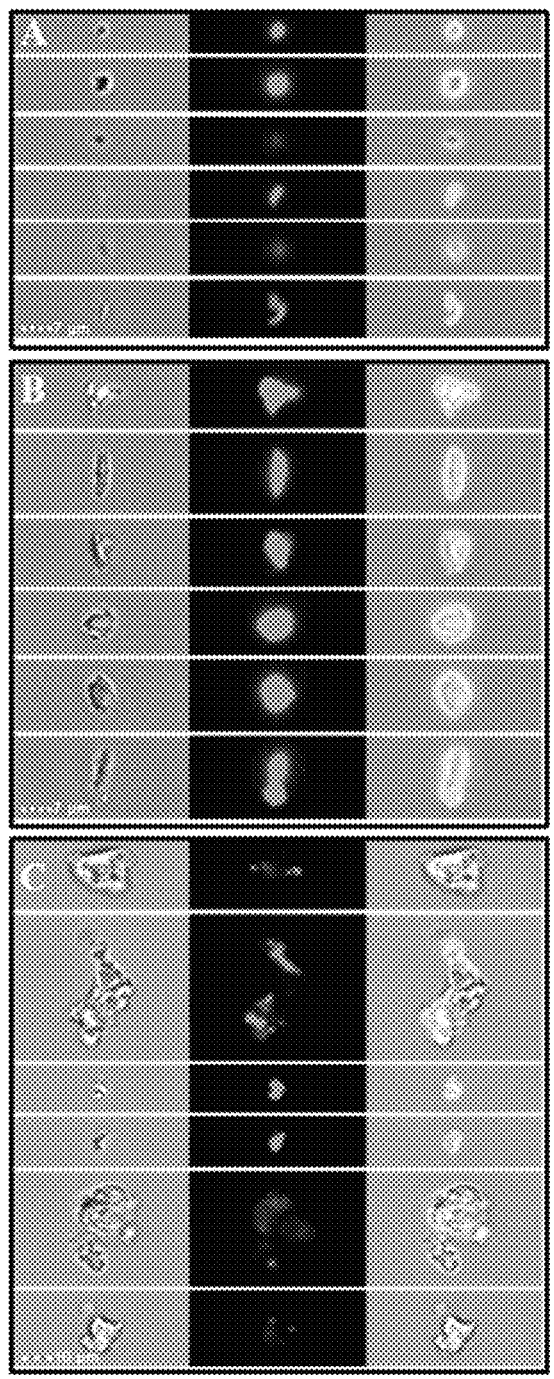
FIGS. 18A-18C: Representative images obtained via ImageStream analysis of microgels encapsulating fluorescent nanogels incubated for 90 minutes in FIG. 18A) 1.2 mg/ml trypsin (scale bar=7 μm), FIG. 18B) 0.6 mg/ml trypsin (scale bar=7 μm), or FIG. 18C) pH 7.4 PBS (scale bar=10 μm). Left: bright field, middle: green channel (nanogels), right: overlay.

Representative images obtained via ImageStream analysis of microgels incubated for 90 minutes in 1.2 mg/ml trypsin, 0.6 mg/ml trypsin, or pH 7.4 PBS are shown in FIG. 18A, FIG. 18B, and FIG. 18C, respectively. Analysis of the microgel populations confirmed that at least 70% of the events detected had fluorescent intensities above a minimum threshold. Further, the events were gated to remove out-of-focus particles and debris from further analysis. The images revealed distinct differences in the size and morphology of the microgels following incubation in the trypsin or PBS solutions; microgels exposed to trypsin are smaller in size and less porous in appearance than microgels exposed to only PBS. Additionally, the fluorescence intensity is very strong and dense in the trypsin samples, whereas it is more diffuse throughout the PBS samples. This could be an indication of formation of strongly fluorescent and highly compact complexes between nanogels and degraded hydrogel due to electrostatic binding, rather than diffusion of nanogels from the degradation hydrogel as desired.

Figures 19A, 19B, 19C:
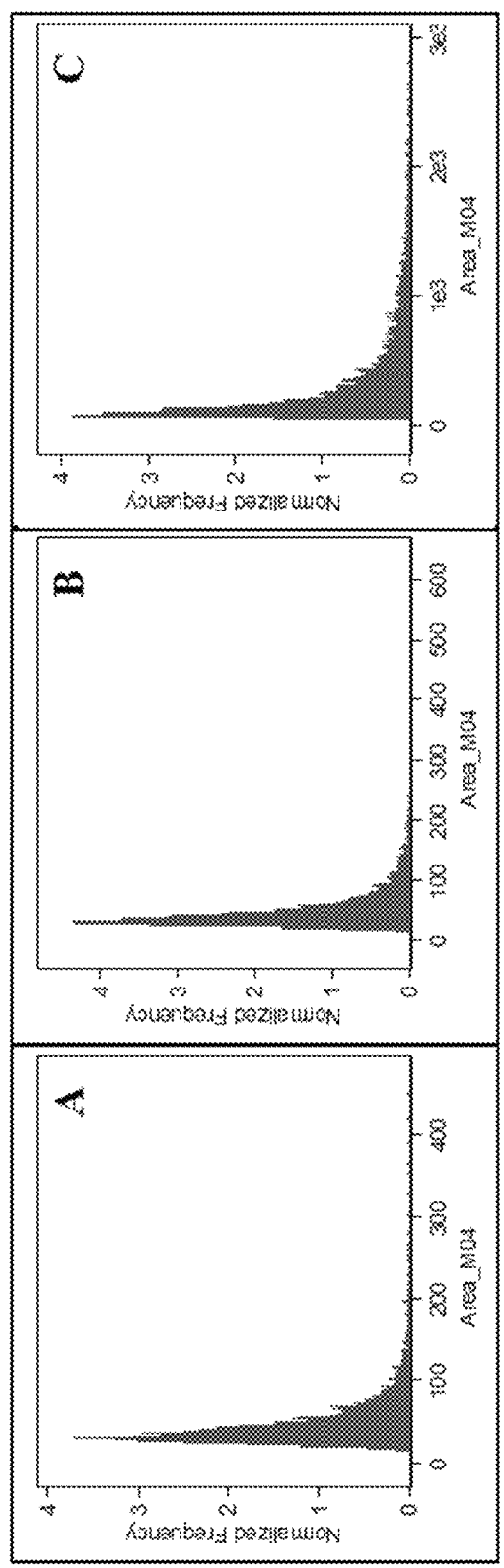
FIGS. 19A-19C: Histogram plots of particle size (μm$^2$) obtained by ImageStream analysis of microgels encapsulating fluorescent nanogels incubated for 90 minutes in FIG. 19A) 1.2 mg/ml trypsin, FIG. 19B) 0.6 mg/ml trypsin, or FIG. 19C) pH 7.4 PBS.

The size distribution of the events was also plotted in histogram form to better quantify the change in size as a function of degradation. FIGS. 19A-C compares the histogram plots of microgels incubated in (FIG. 19A) 1.2 mg/ml trypsin, (FIG. 19B) 0.6 mg/ml trypsin, and (FIG. 19C) PBS. It was observed that compared to the PBS control the size range of microgels was greatly reduced from a maximum of 2800 $\mu m^2$ to 600 $\mu m^2$ upon incubation in trypsin, as would be expected due to enzymatic degradation. Also convincing was the shift in median particle area from 163 $\mu m^2$ in PBS to 39 $\mu m^2$ in trypsin.

Figures 20A, 20B, 20C:
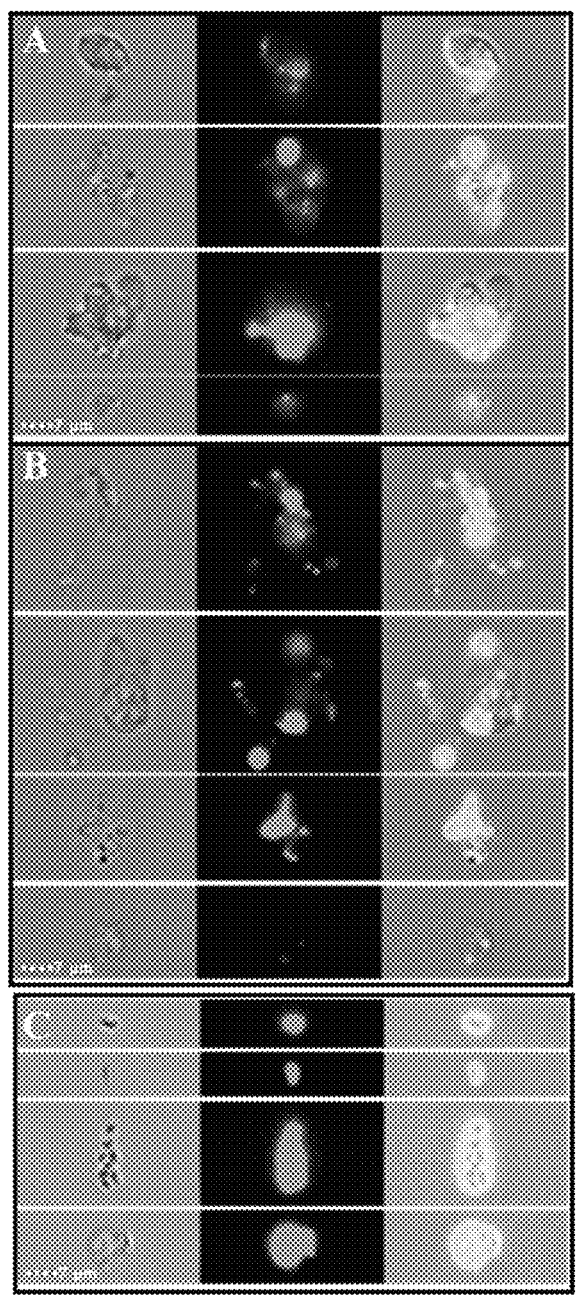
FIGS. 20A-20C: Representative images obtained via ImageStream analysis of microgels encapsulating fluorescent nanogels incubated for ~0 minutes in FIG. 20A) SGF (scale bar=7 μm), FIG. 20B) SIF (scale bar=7 μm), or FIG. 20C) 0.6 mg/ml trypsin (scale bar=7 μm). Left: bright field, middle: green channel (nanogels), right: overlay.
Figures 21A, 21B, 21C:
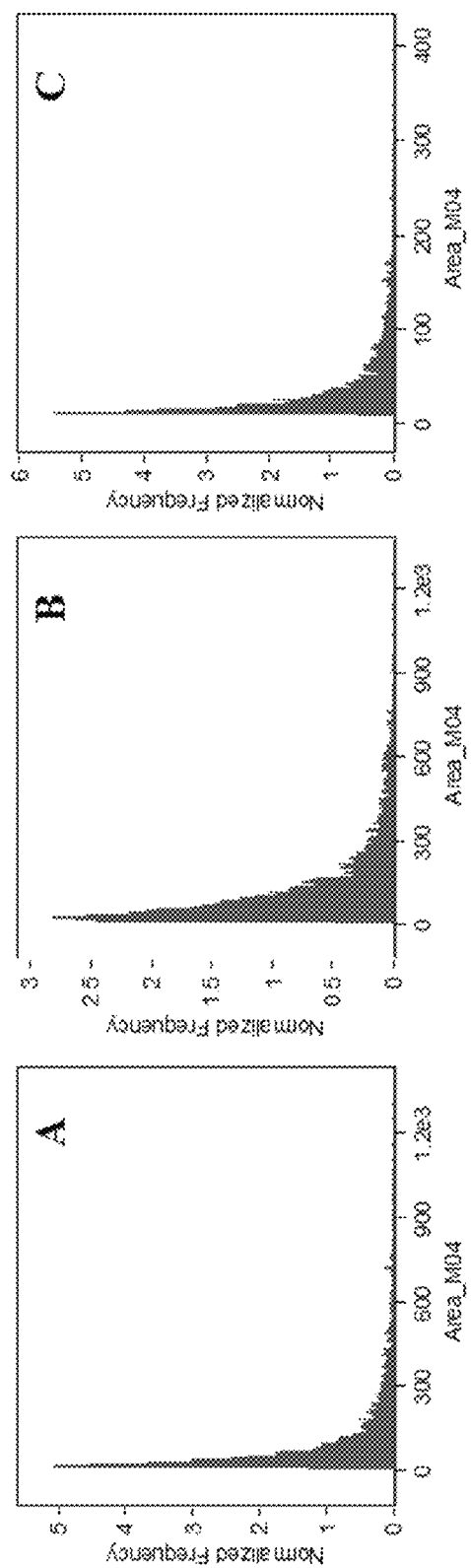
FIGS. 21A-21C: Histogram plots of particle size (μm$^2$) obtained by ImageStream analysis of microgels encapsulating fluorescent nanogels incubated for ~0 minutes in FIG. 21A) SGF, FIG. 20B) SIF, or FIG. 20C) 0.6 mg/ml trypsin.

Similar results were obtained using ImageStream to visualize large populations of microgels incubated in SGF, SIF, or 1.2 mg/ml trypsin solution. Samples were run after 0, 15, 30, 60, and 120 minutes of incubation in each of the conditions. As before, events were gated by fluorescence intensity as well as gradient RMS, a metric used to gate for images in the focal plane. FIGS. 20A-C compares representative images of microgels in each of the solutions at time zero, and FIGS. 21A-C compares the histogram plots of the size distribution of events in each solution at time zero. The size distribution of microgels in SGF and SIF was much broader than that of microgels in trypsin, and again the fluorescence was more diffuse in particles incubated in SGF and SIF than in trypsin. The median microgel sizes were 54, 79, and 23 $\mu m^2$ in SGF, SIF, and trypsin, respectively. Unfortunately, since it was not logistically possible to run the samples at exactly at time zero, some degradation had already occurred in the trypsin samples at the nominal time zero. Consequently there was a slight misrepresentation of the particle size and fluorescent intensity in the trypsin samples at the nominal time zero.

Figures 22A, 22B, 22C:
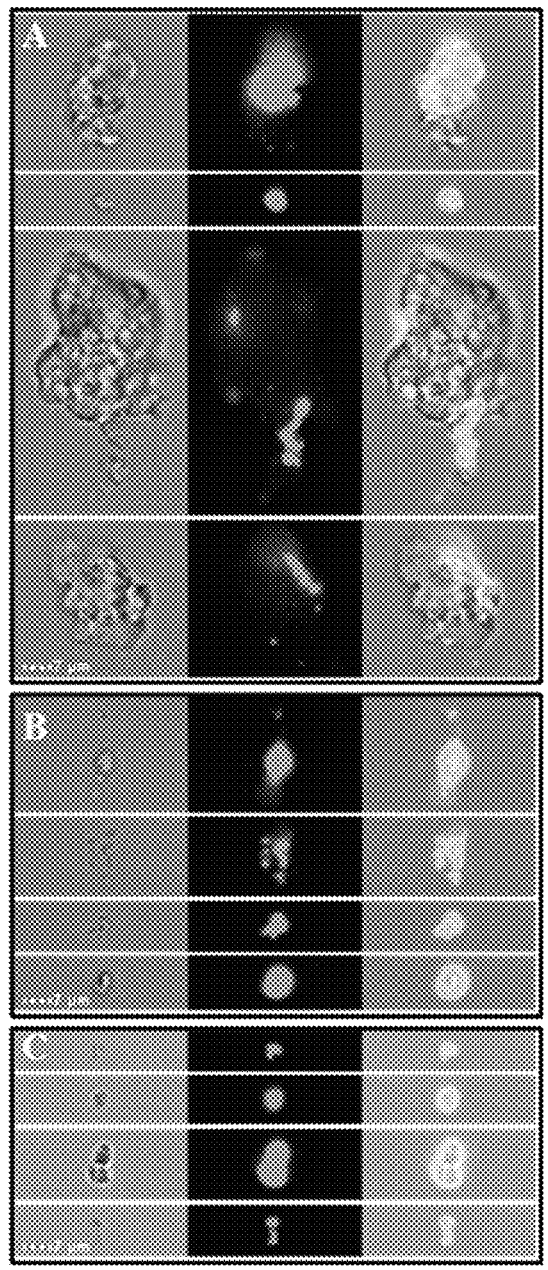
FIGS. 22A-22C: Representative images obtained via ImageStream analysis of microgels encapsulating fluorescent nanogels incubated for 120 minutes in FIG. 22A) SGF (scale bar=7 μm), FIG. 22B) SIF (scale bar=7 μm), or FIG. 22C) 0.6 mg/ml trypsin (scale bar=7 μm). Left: bright field, middle: green channel (nanogels), right: overlay.
Figures 23A, 23B, 23C:
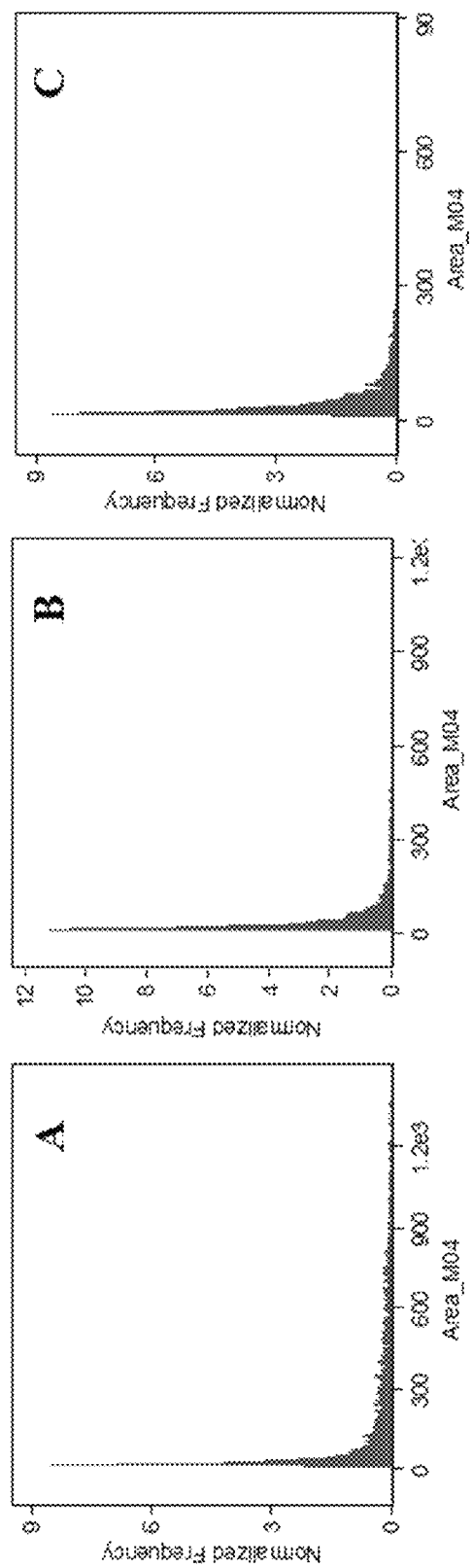
FIGS. 23A-23C: Histogram plots of particle size (μm$^2$) obtained by ImageStream analysis of microgels encapsulating fluorescent nanogels incubated for 120 minutes in FIG. 23A) SGF, FIG. 23B) SIF, or FIG. 23C) 0.6 mg/ml trypsin.

However, the size and fluorescence visualization of the microgels after 120 minutes of incubation was very indicative of the degradation over a longer period of time. FIGS. 22A-C shows representative images of the microgels in each condition and FIGS. 23A-C shows histogram plots of the corresponding microgel size distributions. It is apparent from the images that again the size, morphology, and fluorescence intensity of microgels exposed to SIF and trypsin had discernible differences from that of microgels incubated in SGF, a non-degrading buffer. The degraded particles were small in size and entirely fluorescent compared to their larger undegraded counterparts with diffuse clusters of fluorescence. The histogram plots confirm quantitatively that the size range decreased upon exposure to degrading buffers, and the median sizes were 65 $\mu m^2$ in SGF to 25 and 26 $\mu m^2$ in SIF and trypsin, respectively. Therefore, after 120 minutes of incubation in the buffers, the median size of the microgels in SGF did not decrease, as expected, while the median sizes of microgels exposed to SIF and trypsin did decrease due to degradation.

Figure 24:
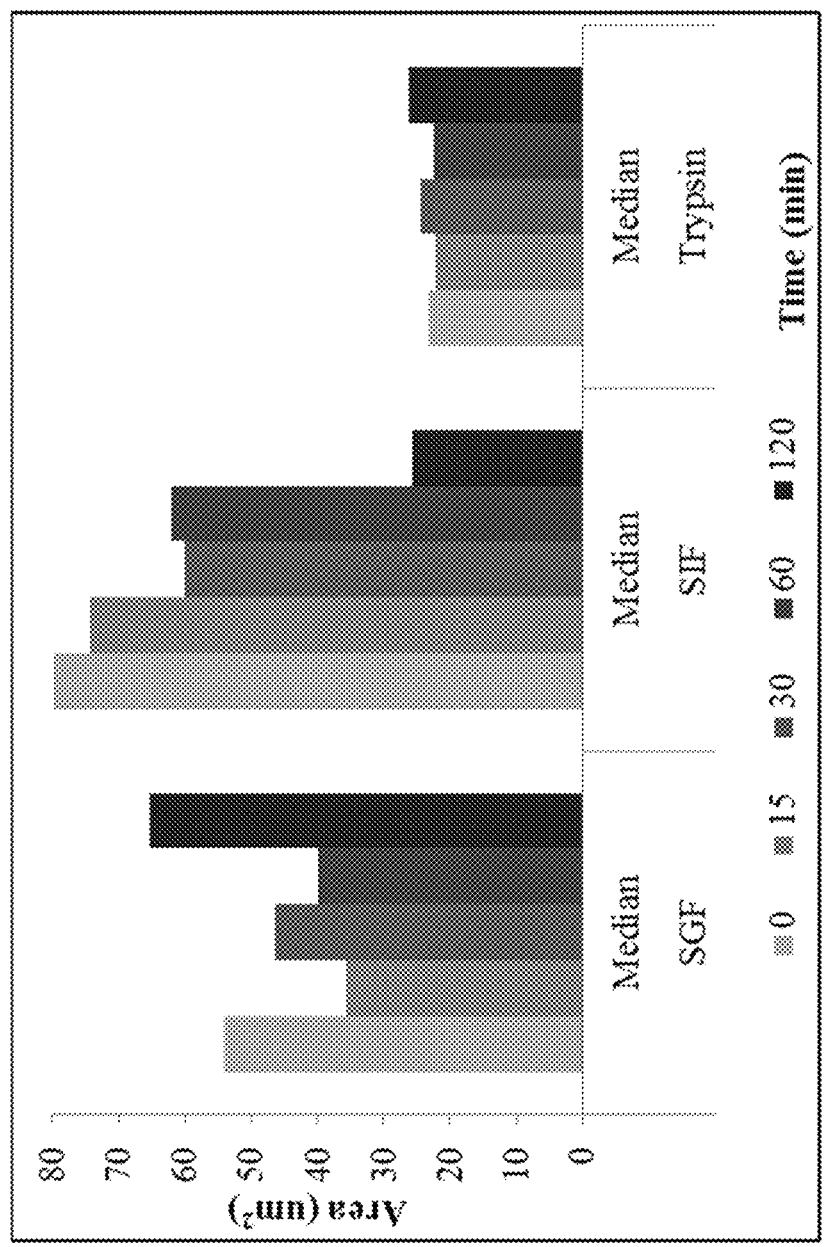
FIG. 24: Median particle size (μm$^2$) values obtained by ImageStream analysis of microgels encapsulating fluorescent nanogels at various time points during the 120 minute degradation period.

FIG. 24 shows the median microgel size ($\mu m^2$) at each time point in each of the three buffers. It can be seen that median size of the particles incubated in SGF fluctuated over time, but did not follow a decreasing trend. The median size of particles incubated in SIF, on the other hand, gradually decreased over the 120 minute incubation period, as would be expected of microgels slowly degraded in the presence of a physiologically relevant concentration of trypsin. Microgels exposed to 1.2 mg/ml trypsin, however, decreased in median size due to degradation by the time of the first measurement and did not degrade further over the 120 minute period.

Cytotoxicity of Degraded Microgels with Nanogels

As the degradation behavior of the microgels containing nanogels was consistent with a relevant timescale in simulated intestinal conditions, the next step was to ensure the cytocompatibility of the degraded and undegraded microgels in trypsin solutions of varying concentration. These studies were critical, as both polycationic polymers such as the nanogels (Fischer et al., 2003) and active trypsin (Kaplan and Bona, 1974; Unanue, 1984), can have a detrimental effect on cell health and metabolism. Caco-2 human adenocarcinoma cells, often used to model the intestinal epithelium, and RAW 264.7 murine macrophage, used to model target cells for nanogel uptake, were used in these studies. Two cytotoxicity assays were used; the MTS cell proliferation assay was indicative of any changes to cell metabolism upon exposure to microgels, and the LDH membrane integrity assay was indicative of the viability of cells after exposure.

Figures 25A, 25B:
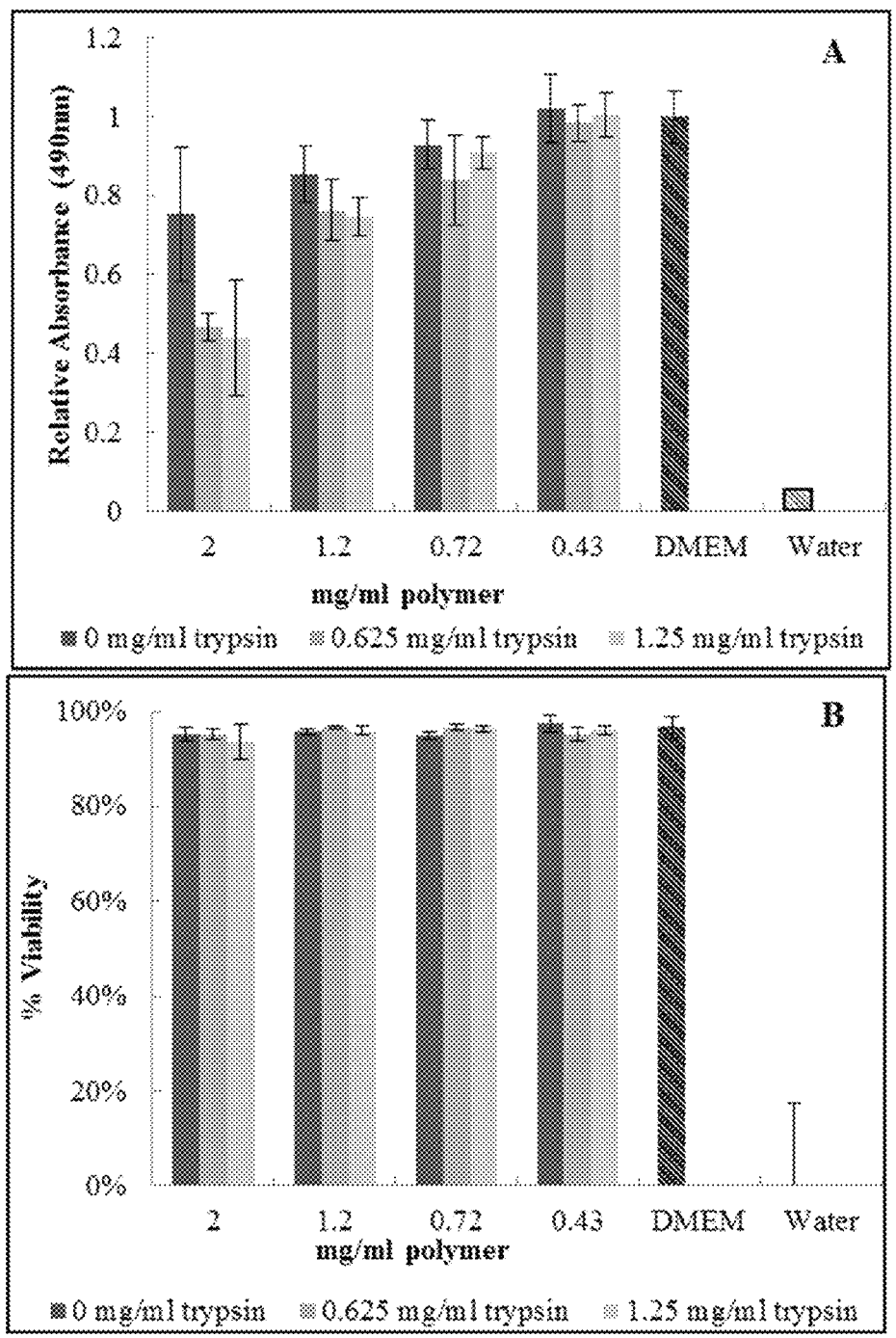
FIGS. 25A-25B: Evaluation of degraded microgel and trypsin exposure effect on cell metabolism using a FIG. 25A) MTS cell proliferation assay (Promega) and FIG. 25B) LDH membrane integrity assay (Promega). Microgels were incubated in PBS or various trypsin concentrations for 4 hours at 37° C., then the trypsin was deactivated by 2× addition of DMEM. Human adenocarcinoma Caco-2 cells were incubated with degraded microgel solutions at various concentrations for 18 hours. Following microgel incubation, the MTS and LDH assays were used to evaluate cytotoxicity. (N=3).

Microgels were incubated in 1.25 or 0.625 mg/ml trypsin solution for at least 4 hours to ensure degradation of the microgels; PBS buffer was used as a control. Trypsin was deactivated by the addition of excess cell media prior to the addition to Caco-2 cells. Cells were incubated with degraded microgel solutions for 18 hours to assess cytotoxic effect. FIG. 25A and FIG. 25B show Caco-2 cell proliferation and viability, respectively, as a function of microgel and trypsin concentration relative to cells incubated in normal media without microgels. The cell proliferation was affected by the degraded microgels in a concentration-dependent manner; the highest concentration of 2 mg/ml induced an unacceptable amount of change in cell metabolism as measured by the MTS assay. However, all concentrations maintained very high cell viability after 18 hours of incubation. Thus, high concentrations of degraded microgels may affect the metabolism of Caco-2 cells, but the do not kill the cells.

A comprehensive study evaluating effect of trypsin concentration, culture medium, and trypsin concentration during degradation was performed in the RAW 264.7 cells. Microgels at a concentration of 2 mg/ml were degraded in 0.15, 0.2, 0.25, and 0.3 mg/ml trypsin for 90 minutes at 37° C., and then the trypsin was deactivated by incubation at 70° C. for 5 minutes. The microgels were then added to the cells at a final concentration of 1 mg/ml or 0.4 mg/ml in OptiMEM or 1 mg/ml in DMEM. Two different culture media were tested as the OptiMEM is a reduced-serum medium, and the presence of serum is thought to negatively impact cellular uptake and transfection by nanoparticles. Therefore, it was hypothesized that increased uptake of nanoparticles with inherently cytotoxic cationic functional groups may be more disruptive to the cell metabolism or cell membrane.

Figures 26A, 26B, 26C:
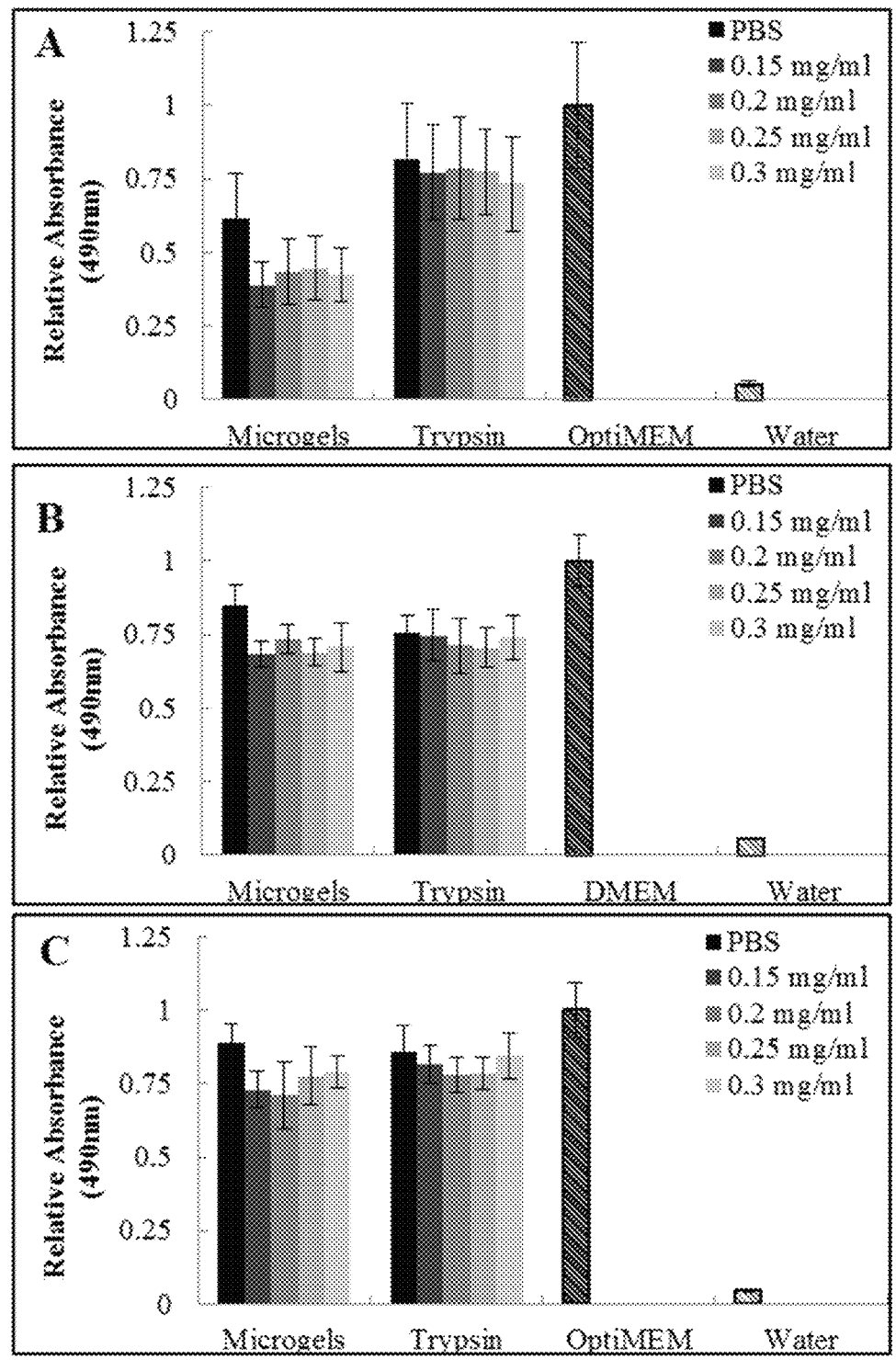
FIGS. 26A-26C: Evaluation of degraded microgel and trypsin exposure effect on cell metabolism using a MTS cell proliferation assay (Promega). Microgels were incubated in PBS or various trypsin concentrations for 90 minutes at 37° C., then the trypsin was deactivated by incubation at 70° C. for 5 minutes. Murine macrophage RAW 264.7 cells were incubated with degraded microgel solutions at FIG. 26A) 1 mg/ml in OptiMEM.

FIGS. 26A-C shows the results of the MTS cell proliferation assay following incubation of the RAW 264.7 cells with the degraded microgels for 18 hours. Absorbance at 490 nm is relative to that of cells exposed only to culture medium for the 18 hour incubation period. In all three exposure conditions, undegraded microgels in PBS were slightly less disruptive to cell metabolism than degraded microgels, suggesting that degradation of the microgel matrix does cause increased cellular exposure to the potentially cytotoxic polycationic nanogels within.

FIG. 26A shows that the 1 mg/ml microgel concentration in OptiMEM did have an effect of cellular metabolism, as the relative absorbance was reduced below 50% at all trypsin concentrations. Also important to note is that cells exposed to the deactivated trypsin without microgels also experienced a reduction in relative absorbance, indicating the negative effect of high trypsin concentrations on cell metabolism.

FIG. 26B indicates that the same microgel concentration in serum-containing DMEM resulted in less effect on cell metabolism due to the degraded microgels, as the relative absorbance of trypsin with and without microgels was approximately the same. This could be due to the serum content causing nonspecific protein binding to the nanogels, resulting in a reduction in both cytotoxicity and cellular uptake. It is important to note, though, that this concentration of microgels did result in a 30% reduction in absorbance relative to the control cells incubated in DMEM only. Therefore, this microgel concentration still significantly affects cell metabolism.

Finally, FIG. 26C shows the results of the MTS assay of RAW 264.7 cells incubated with 0.4 mg/ml degraded microgels in OptiMEM culture medium. As expected, the lower microgel concentration resulted in less disruption of cell metabolism relative to cells exposed only to OptiMEM, with a decrease in relative absorbance of only ~25% across all trypsin concentrations. There was also little difference in relative absorbance between cells incubation deactivated trypsin alone or deactivated trypsin with degraded microgels.

Figures 27A, 27B, 27C:
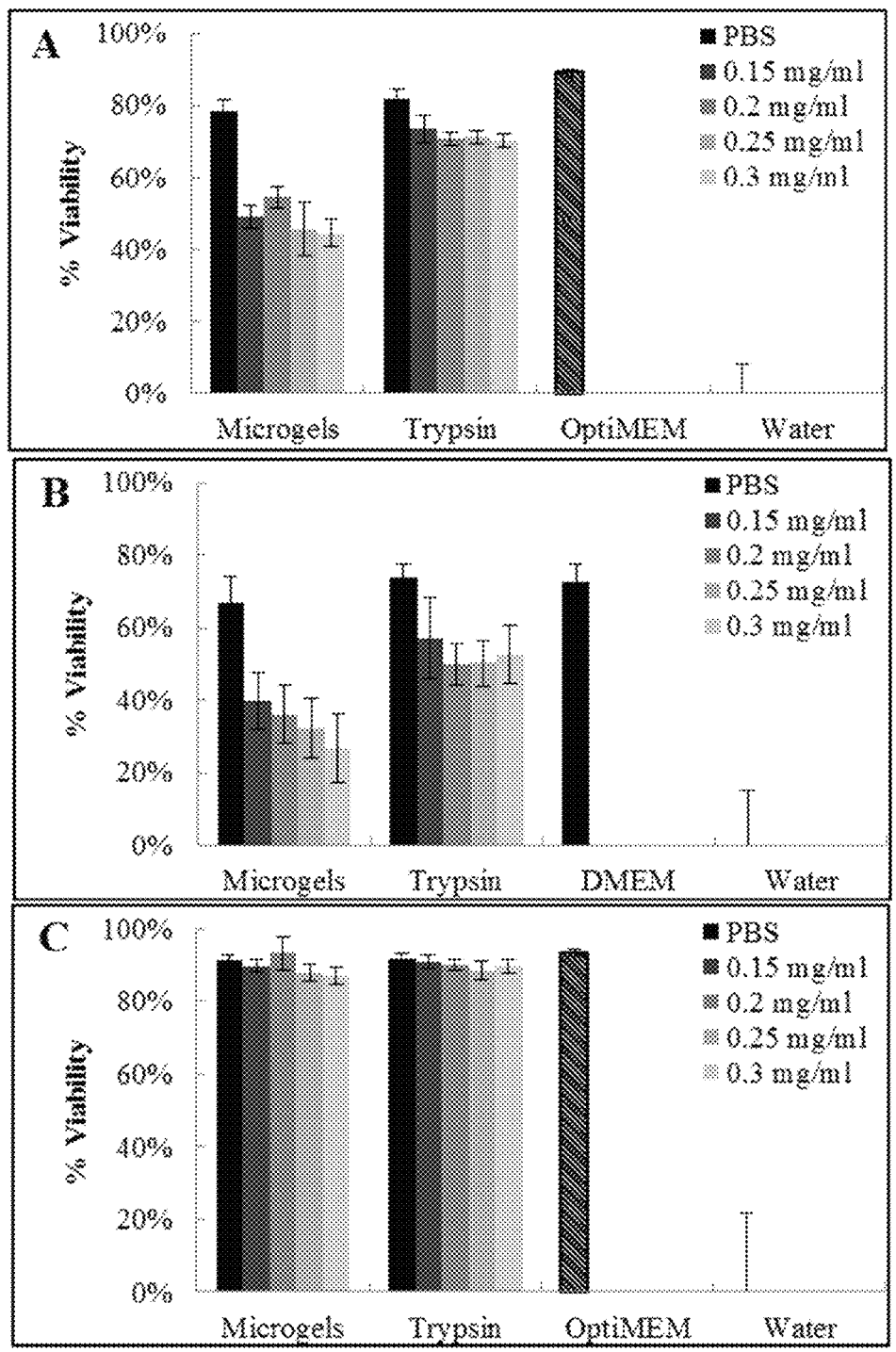
FIGS. 27A-27C: Evaluation of degraded microgel and trypsin exposure effect on cell metabolism using a LDH membrane integrity assay (Promega). Microgels were incubated in PBS or various trypsin concentrations for 90 minutes at 37° C., then the trypsin was deactivated by incubation at 70° C. for 5 minutes. Murine macrophage RAW 264.7 cells were incubated with degraded microgel solutions at FIG. 27A) 1 mg/ml in OptiMEM.

The results from the LDH assay, shown in FIGS. 27A-C, mirror the results from the MTS assay, with the only notable exception being a much more pronounced effect of 1 mg/ml degraded microgels in DMEM on membrane integrity, shown in FIG. 27B. Interestingly, this negative effect was a function of microgel:trypsin ratio, with ratios likely resulting in less degradation being less detrimental to cell viability. In fact, undegraded microgels in PBS were significantly less toxic at 70% viability than microgels incubated in the lowest trypsin concentration, at 40% viability. This strongly suggests that the degradation products or release of nanogels from degraded microgels has a detrimental effect on cell membrane viability at this concentration.

At the reduced concentration of 0.4 mg/ml in OptiMEM shown in FIG. 27C, however, cell viability is quite high at >80% for all conditions tested. In subsequent cell transfection studies, these conditions were used to induce minimal toxic effect as a result of microgels or degradation conditions.

siRNA Loading

Loading studies were conducted with the Silencer® Select Negative Control No. 1 scrambled sequence siRNA at 1000 nM or 400 nM to evaluate the ability of the microgels to load siRNA. Microgels were incubated with the siRNA at a particle concentration of 12 mg/ml in pH 5.5 PBS for up to 4 hours at room temperature with agitation. The loading pH was selected as both the microgels and nanogels are partially charged at this condition, facilitating swelling of the hydrogel networks to allow increased diffusion of siRNA to complex with the positively charged nanogels. Following incubation, the microgel/siRNA solutions were centrifuged to separate loaded microgels from siRNA remaining in solution. Afterwards, the siRNA content in the supernatant was measured with the Quant-iT™ RiboGreen® RNA Assay Kit.

Loading efficiencies were calculated as follows, where $c_0$ is the initial molar siRNA concentration, $c_f$ is the final molar siRNA concentration, and $c_p$ is the mass concentration of polymer in solution:

$$\text{Loading Efficiency} = \frac{c_0 - c_f}{c_0} * 100 \tag{7.2}$$

$$\text{Weight Loading Efficiency} = \frac{c_0 - c_f}{c_p} * 100 \tag{7.3}$$

Figure 28:
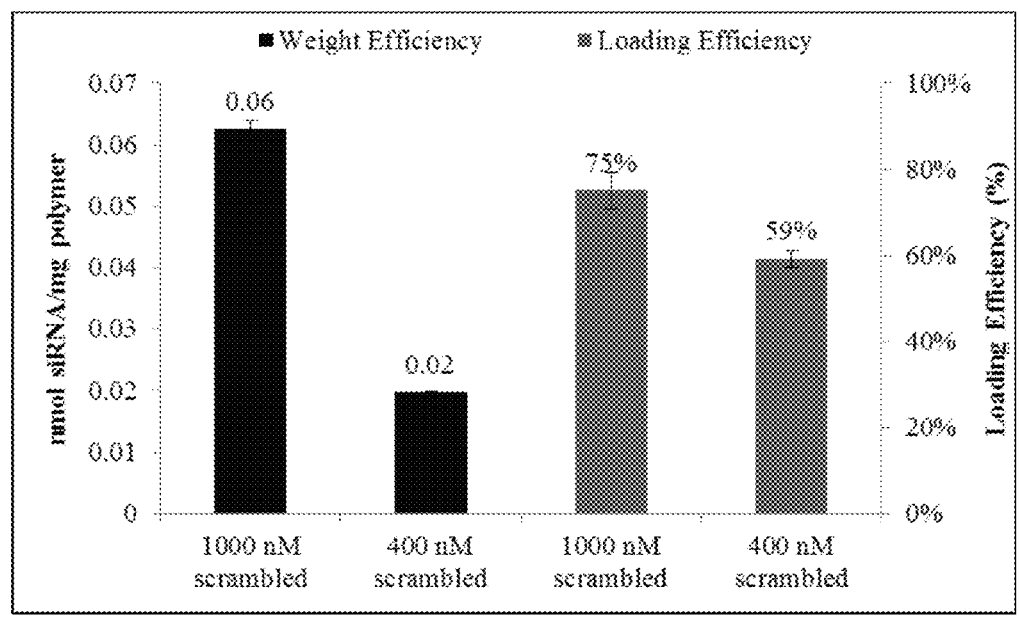
FIG. 28: Representative siRNA loading efficiencies of degradable P(MAA-co-NVP) microgels with peptide crosslinker and encapsulated polycationic nanogels. Loading efficiency was based on amount of siRNA in microgels relative to initial amount in solution. Weight loading efficiency is moles of siRNA relative to the weight of microgels. Microgels were loaded over 4 hours at room temperature (N=3).

Representative weight and loading efficiencies of the scrambled siRNA are shown in FIG. 28. This scrambled siRNA sequence achieved weight efficiencies of 0.06 and 0.02 nmol siRNA/mg polymer and loading efficiencies of 75% and 59% in 1000 nM and 400 nM siRNA loading concentrations, respectively. The weight and loading efficiencies were highest in the loading solution with the greater siRNA concentration, as would be expected due to the greater concentration gradient acting as a diffusional driving force. In general for a variety of siRNAs tested, weight efficiencies ranged from 0.02-0.11 nmol siRNA/mg polymer, and loading efficiencies ranged from 59-90%. The variation in loading efficiency was attributed to batch-to-batch variability in the microgels as well as differences in siRNA sequences. Incubation time for loading did not greatly affect efficiencies, and consequently the loading period was reduced to 1.5 hours to limit degradation of siRNA by hydrolysis.

The loading efficiencies were consistently lower than those achieved with nanogels alone (Forbes and Peppas, 2014), but this was to be expected due to the increased complexity of diffusion through the microgel matrix as well as the possibility of unfavorable electrostatic repulsion between the polyanionic P(MAA-co-NVP) and negatively charged siRNA. Overall, the results indicate that these concerns are not prohibitive to loading siRNA into the microgels as significant loading of the siRNA was achieved.

Microgel Degradation and siRNA Stability

As siRNA is quite susceptible to degradation by proteases (Fattal and Bochot, 2008), there was concern that the stability and integrity of the siRNA could be compromised during the trypsin-induced degradation of the microgels. Therefore, the stability of the siRNA following incubation in various conditions was evaluated by polyacrylamide gel electrophoresis (PAGE), as has been reported previously in the literature (Hickerson et al., 2008). PAGE separates molecules by electrophoretic mobility, which is a function of the size, conformation and charge of the molecule. Thus, it is widely used to determine the stability of various biological molecules including proteins, RNA, and DNA.

Figures 29A, 29B:
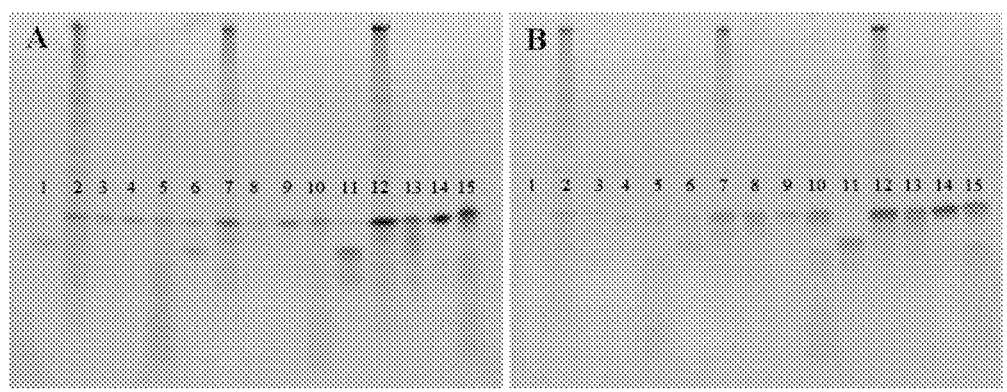
FIGS. 29A-29B: PAGE evaluation of siRNA degradation after siRNA-loaded microgels were incubated in 1) 0.3 mg/ml trypsin; 2) rat intestinal fluid; 3) rat gastric fluid; 4) PBS; or 5) SGF; siRNA-complex nanogels incubated with 6) 0.3 mg/ml trypsin; 7) rat intestinal fluid; 8) rat gastric fluid; 9) PBS; or 10) SGF; or siRNA incubated with 11) 0.3 mg/ml trypsin; 12) rat intestinal fluid; 13) rat gastric fluid; 14) PBS; or 15) SGF. Solutions were run FIG. 29A) immediately after incubation in the buffers or FIG. 29B) after an additional 15 minute incubation with heparin solution.

In the case of denaturing PAGE, as was utilized in the studies herein, the higher order structure of the siRNA was denatured by exposure to urea, limiting the dependence of electrophoretic mobility to size and charge alone. In this way, the degradation of siRNA in various conditions was examined. Microgels with nanogels loaded with siRNA, nanogels complexed with siRNA, and siRNA alone were incubated in 0.3 mg/ml trypsin in PBS, rat intestinal fluid, rat gastric fluid, PBS, or SGF for 90 minutes at 37° C. followed by 5 minutes incubation at 70° C. to deactivate trypsin. Microgels were incubated at a concentration of 5 mg/ml, nanogels at a concentration of 0.4 mg/ml, and siRNA at a concentration of 400 nM. FIG. 29A shows the image of the gel; it was noted that the samples incubated with trypsin showed signs of significant siRNA degradation, evidenced by the smaller molecular weight bands in lanes 1, 6, and 11. Without wishing to be bound by any theory, it was positive that at least some of the siRNA remained stable in rat intestinal fluid and PBS (lanes 2, 7, 12 and 4, 9, 14, respectively). As expected, rat gastric and SGF conditions resulted in noticeable siRNA degradation (lanes 3, 8, 13 and 5, 10, 15, respectively). siRNA release from the degraded microgels and nanogels was observed, as evidenced by the bands corresponding to the stable siRNA band in lane 14.

The same siRNA-loaded samples incubated in the various conditions were then incubated in 0.5 mg/ml heparin in OptiMEM to better evaluate release of siRNA in the various conditions. Heparin was used as a competitive polyanion to induce dissociation of the siRNA from the polycationic nanogels, as other researchers have reported (Moret et al., 2001; Zelphati et al., 1996). FIG. 29B shows the image of the gel of the samples after incubation with heparin. Again, it was observed that free, undegraded siRNA was present in all samples with the exception of the samples incubated at high trypsin concentration. The presence of heparin did not seem to increase dissociation of the siRNA. Of course, it is impossible to say conclusively whether or not the free siRNA increased upon incubation with heparin without extracting and quantifying siRNA in the gel, but it was determined that the effort required to quantify the siRNA was not justified in this experiment. The presence of free, undegraded siRNA following incubation in physiologically relevant proteolytic conditions was confirmed, and this proof-of-concept was sufficient for these studies.

Looking for closely at the effect of trypsin on siRNA stability, siRNA, siRNA complexed with nanogels, and microgels with nanogels loaded with siRNA were degraded in 0.6 mg/ml trypsin for 1 hour at 37° C., and then the trypsin was deactivated by incubation at 70° C. for 5 minutes. One set was added to PBS an identical set was added to a 0.5 mg/ml heparin solution to promote dissociation of siRNA. As a control, siRNA was incubated in 0.05, 0.1, and 0.5 mg/ml Ribonuclease A to fully degrade the siRNA.

Figures 30A, 30B:
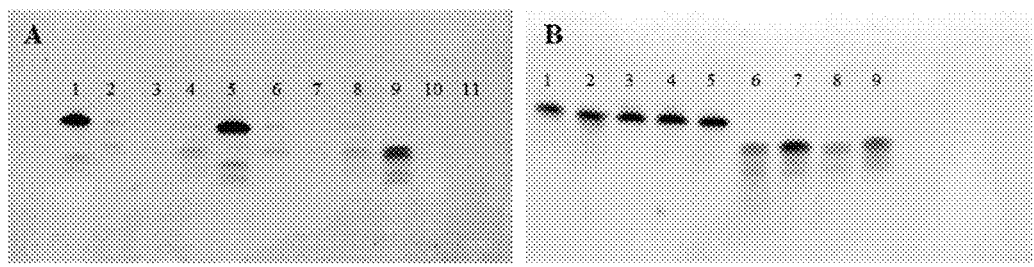
FIGS. 30A-30B.

FIG. 30A shows the PAGE results. Intact siRNA bands were clearly shown in lanes 1 (without heparin) and 5 (with heparin), though some bands of degraded siRNA were also present. Faint bands of intact siRNA were present in the nanogel samples (lanes 2 and 6) as well as in one of the degraded microgel samples (lanes 4 and 8). Again, it seemed as if heparin had no effect on the amount of free siRNA. It was unexpected that only one of the microgel samples contained intact siRNA, it is possible that the sample in lanes 3 and 7 was contaminated with an RNase. The bands of siRNA fully degraded by RNase can be seen in lane 9; the higher concentrations of RNase degraded the siRNA to such an extent that it ran off the gel and was no longer detectable.

To verify that the degradation observed in all samples was not due to the incubation temperature or pH at which the siRNA was incubated, siRNA alone was incubated on ice, at room temperature followed by 90° C. for 5 minutes, pH 5.5 PBS at 37° C., pH 8.5 PBS at 37° C., with microgels at loading conditions, and in 1.2 or 0.6 mg/ml trypsin with and without particles at 37° C. As shown in FIG. 30B, only the siRNA exposed to trypsin, with or without microgels, experienced degradation. This confirms that the high trypsin activity was the culprit behind the degraded siRNA and not hydrolysis at elevated temperature.

The concentrations of trypsin used in these studies are much higher than physiologically relevant trypsin levels. As demonstrated in rat intestinal fluid, it is anticipated that the ability of these microgel systems to deliver intact siRNA in physiological or in vivo conditions may be significantly greater than these studies project.

Confocal Microscopy to Verify Internalization

Confocal laser scanning laser microscopy was used to verify cellular internalization of nanogels from degraded microgels. Microgels containing fluorescently tagged nanogels were incubated in 0.6 mg/ml trypsin for 90 minutes to degrade the microgel matrix and allow release of the nanogels. Following degradation, the samples were incubated at 70° C. for 5 minutes to deactivate the trypsin and the degraded microgels were added to cells at a final concentration of 0.5 mg/ml in OptiMEM. The cells were incubated for 18 hours with the degraded particles then fixed, stained with fluorescently labeled wheat germ agglutinin, a cell membrane marker, then extensively washed and mounted onto slides with ProLong® gold antifade reagent containing DAPI nuclear stain. Nanogels alone were used for comparison, as the cellular internalization of the nanogels has been previously documented (Forbes and Peppas, 2014). All images were representative of the entire cell population; in each condition tested, the cells were at approximately 60% confluence and appeared to be in good health as determined by the bright field images.

Figures 31A, 31B:
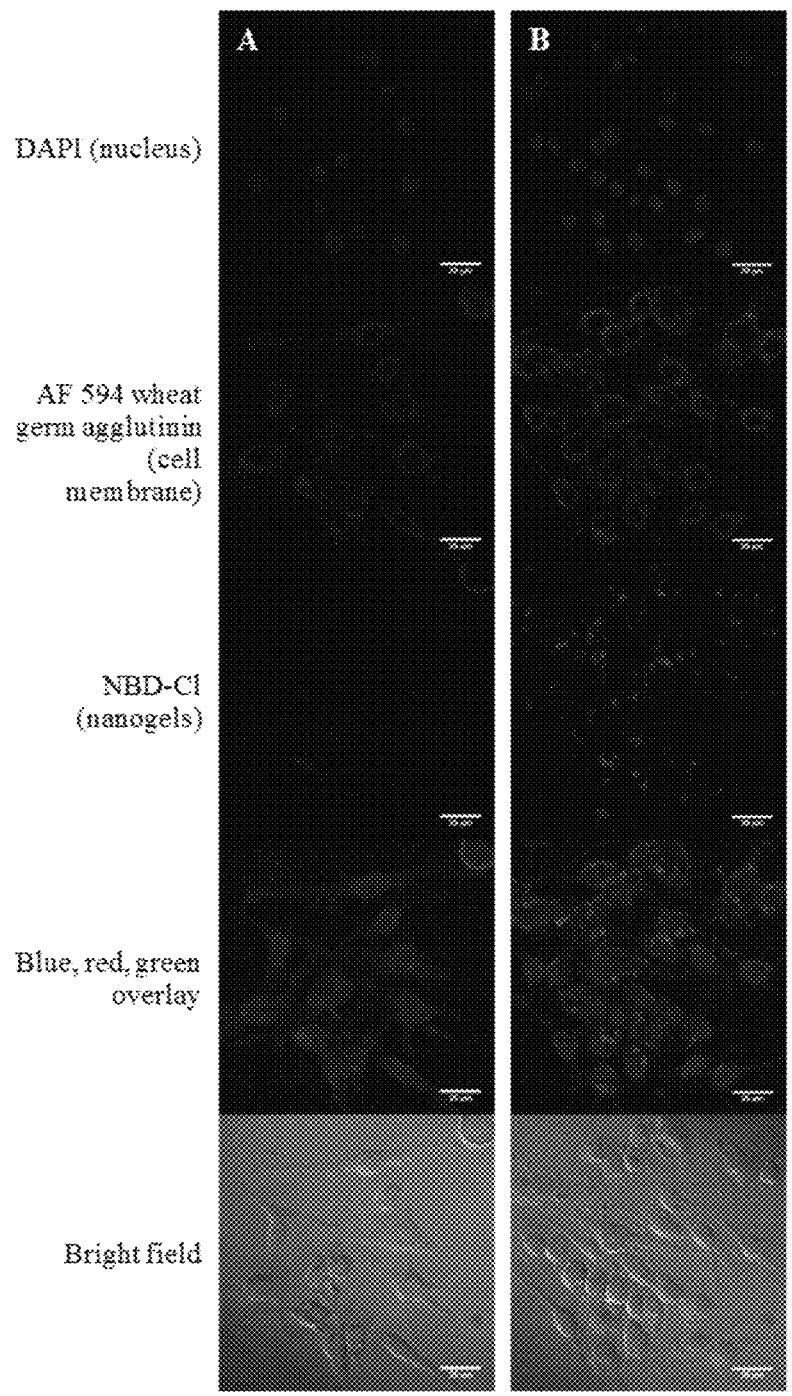
FIGS. 31A-31B: Confocal laser scanning microscopy fluorescent and bright field images of RAW 264.7 cells incubated with FIG. 31A) nanogels and FIG. 31B) degraded microgels containing nanogels (Scale bar=20 μm).

FIGS. 31A-B shows the fluorescent and bright field images of RAW 264.7 cells incubated with nanogels (FIG. 31A) and degraded microgels containing nanogels (FIG. 31B). In both cases, comparison of the artificially-colored green in the third panel with the bright field images in the fifth panel as well as the fluorescent overlay in the fourth panel indicated the presence of nanogels in proximity to the nuclei of cells, suggesting internalization. Interesting to note is the high prevalence of micron-size particles with green fluorescence both near and around the cells in the degraded microgel samples; this lends credibility to the working theory that upon degradation the nanogels do not completely release from the microgel matrix. Rather, they may be electrostatically bound with degraded microgel products in a highly fluorescent complex that is microns in size.

Figures 32A, 32B:
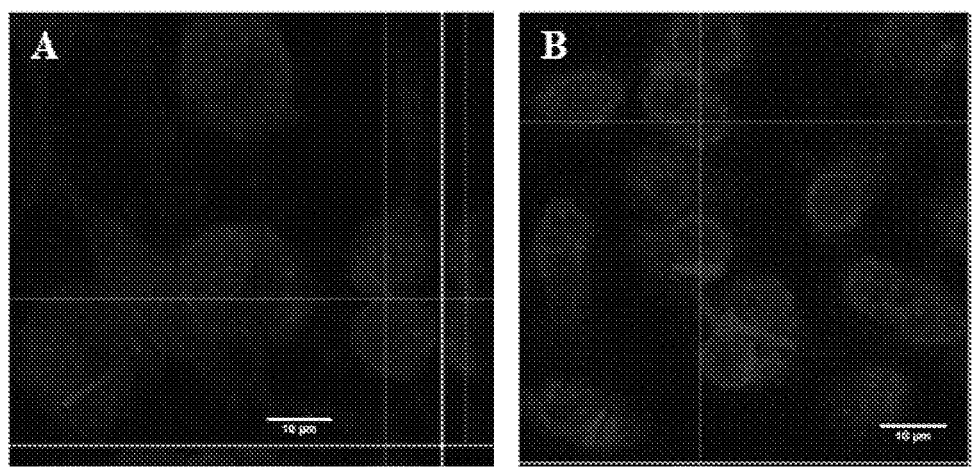
FIGS. 32A-32B: Confocal laser scanning microscopy fluorescent Z-stack orthogonal images of RAW 264.7 cells incubated with nanogels (FIG. 32A) and degraded microgels containing nanogels (FIG. 32B) (Scale bar=10 μm).

To verify internalization of nanogels, Z-stack images through the cells were taken. An orthogonal view of the Z-stacks, shown in FIGS. 32A-B, confirmed the presence of the nanogels within the artificially-colored red cell membranes. Within the orthogonal view, the main panel displays the x-y plane, the bottom panel displays the x-z plane, and the right panel displays the z-y plane. In both the cells with nanogels, FIG. 32A, and the cells with degraded microgels and nanogels, FIG. 32B, the nanogels were localized within the cells membranes, which was likely indicative of endosomal compartmentalization. In the case of the degraded microgels with nanogels, at least some of the potentially electrostatically-bound nanogel complexes were still able to be internalized by cells. Therefore, the complexation does not entirely prohibit internalization, but may affect efficacy and siRNA delivery.

Figures 33A, 33B, 33C:
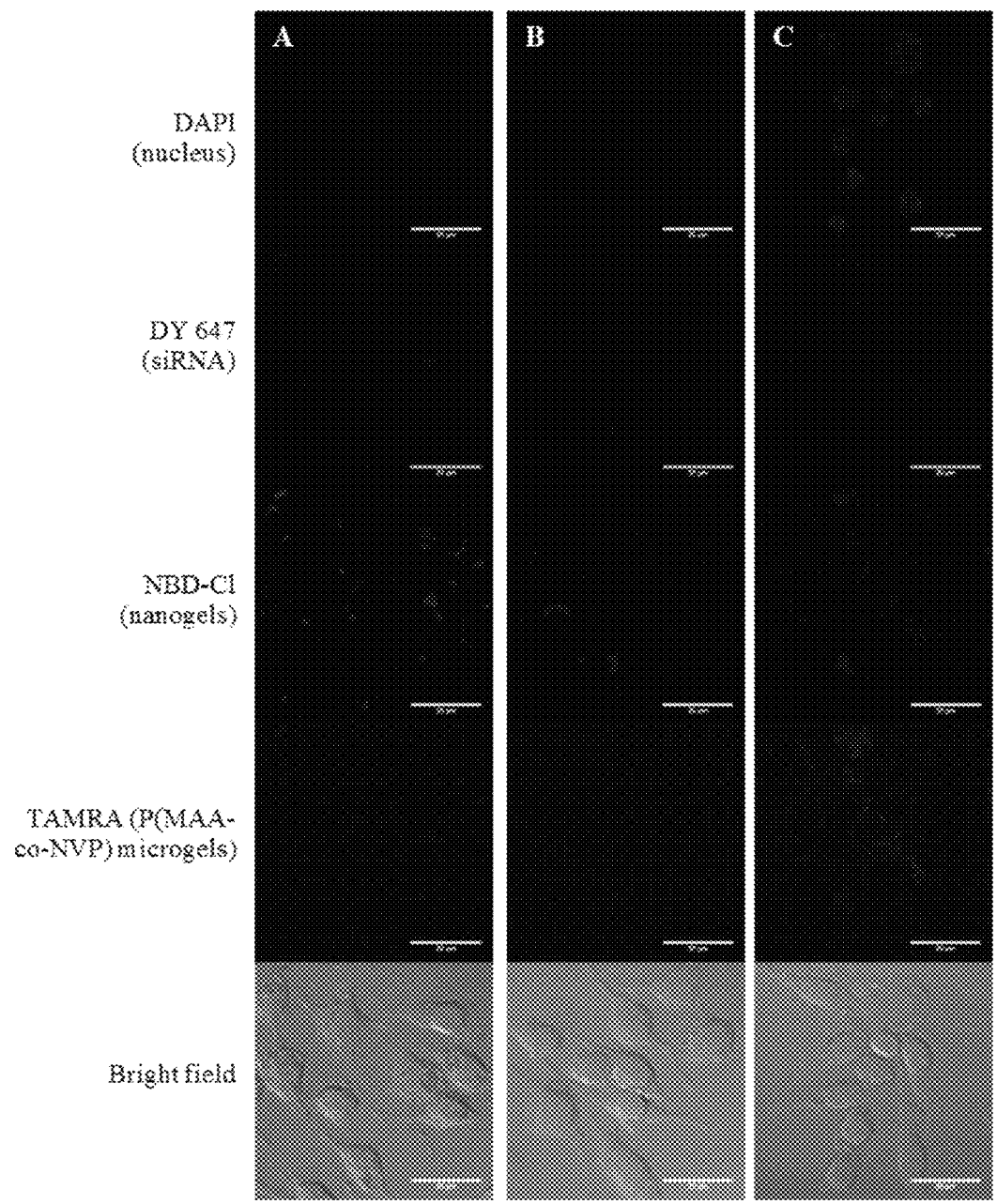
FIGS. 33A-33C: Confocal laser scanning microscopy fluorescent and bright field images of RAW 264.7 cells incubated with FIG. 33A) degraded microgels with fluorescently-tagged nanogels and fluorescently-tagged siRNA.

With the goal of getting a better idea of the electrostatic interactions between the microgels, nanogels, and siRNA, all three of which are charged species, microgels and nanogels loaded with DY 647-siRNA were also degraded and incubated with RAW 264.7 cells in the same manner. FIGS. 33A-C shows images of cells incubated with FIG. 33A) degraded microgels containing nanogels and siRNA; FIG. 33B) nanogels complexed with siRNA; and FIG. 33C) TAMRA-labeled microgels with nanogels and siRNA. Again, in all three cases the fluorescence of the nanogels in relation to the bright field image suggests that cellular uptake of the nanogels may be occurring. Additionally, the fluorescence of the siRNA is in good spatial agreement with the nanogel fluorescence, indicating complexation between the two species. As before, the relatively large clusters of degraded microgel and nanogels are visible around the cells in the bright field images of FIG. 33A and FIG. 33C, and there is associated fluorescence of each of the charged molecules corresponds to these clusters. These data support the idea that complexation is occurring between microgels, nanogels, and siRNA.

Transfection of Murine Macrophage and Human Adenocarcinoma Cells

Transfection conditions were determined by the best cytotoxicity, degradation, and siRNA stability results. RAW 264.7 murine macrophage and Caco-2 human adenocarcinoma cells were incubated with siRNA and degraded microgels (0.4 and 0.7 mg/ml), undegraded microgels (0.7 mg/ml), nanogels (0.025 mg/ml), commercially available transfection agent Lipofectamine 2000, or naked siRNA. Both cell lines were treated identically, with the exception of mouse and human variant AllStars Death siRNA. Silencing was measured by an MTS assay of cell proliferation relative to that of scrambled siRNA controls. Experiments were run in quadruplicate and were repeated across two sets of each cell line.

Figures 34A, 34B:
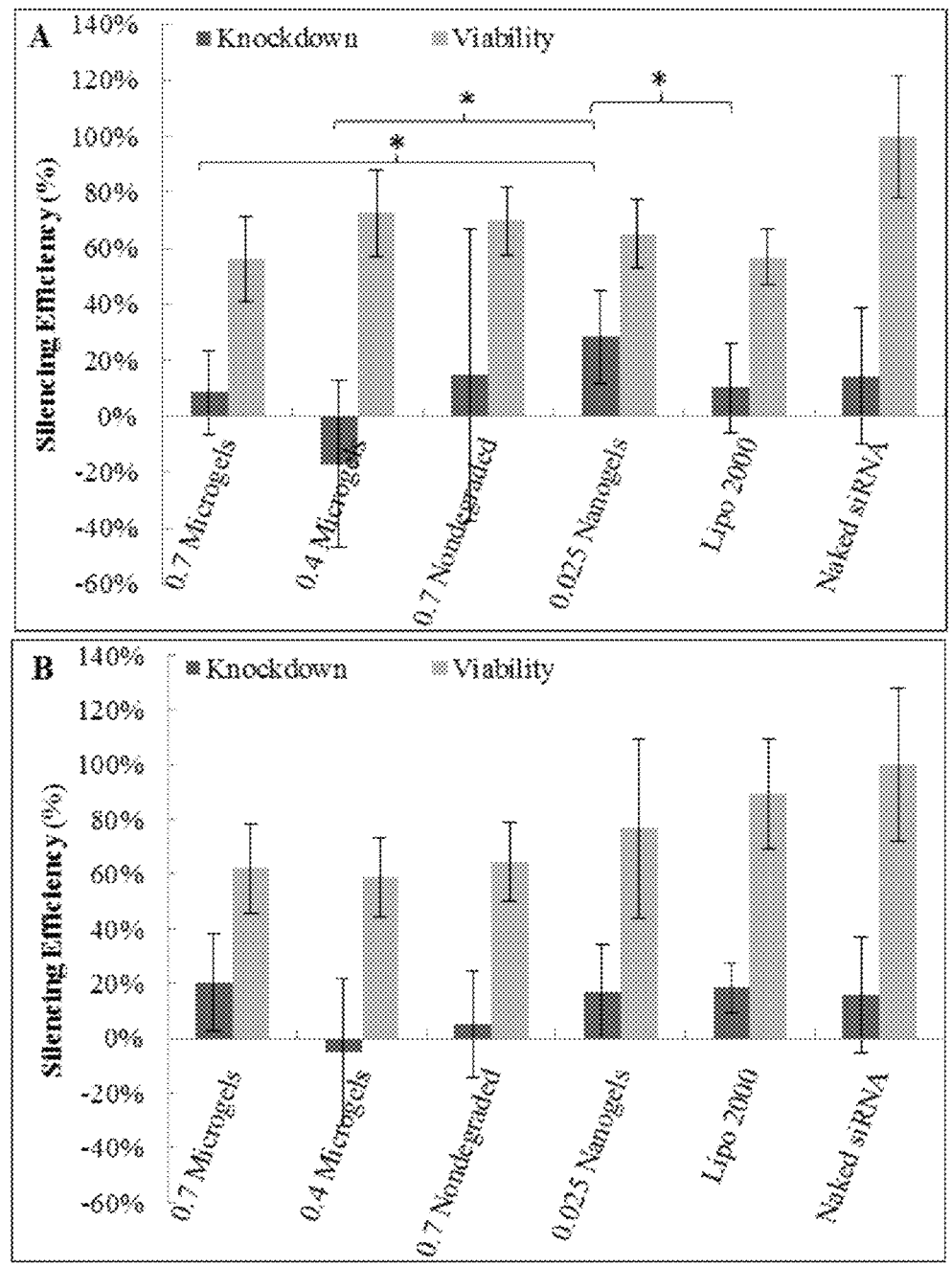
FIGS. 34A-34B: Gene knockdown by degraded and undegraded microgels containing nanogels, nanogels, commercially available Lipofectamine 2000, or naked siRNA. All-Stars Death and Negative Control (Qiagen) were used, and MTS cell proliferation assay was used to quantify silencing efficiency (N=4, *p<0.05).
Figures 35A, 35B, 35C, 35D:
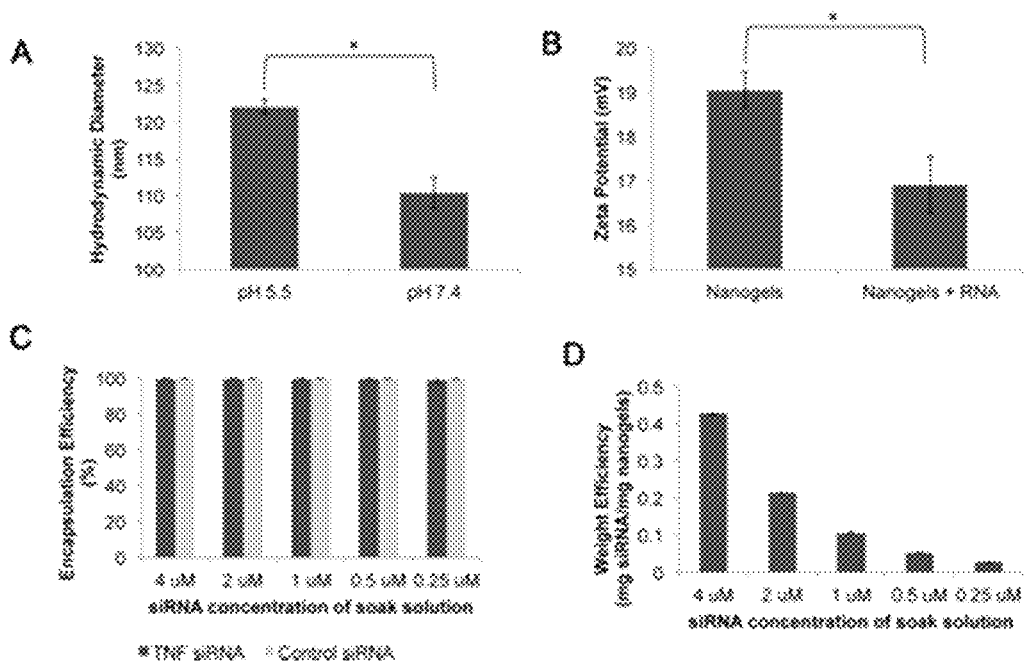
FIGS. 35A-35D. Characterization and siRNA loading of P(DEAEMA-co-tBMA) nanogels.

As shown in FIGS. 34A-B, similar gene silencing was obtained in both the FIG. 34A) RAW 264.7 and FIG. 34B) Caco-2 cell lines. At all concentrations and conditions tested, the microgels were unable to achieve greater than 20% silencing, and in some instances the variation between experiments was quite large. In fact, in the RAW cells the silencing by the degraded microgels with nanogels was significantly less than the silencing by nanogels with siRNA (T-test, $p<0.05$). Silencing efficiency was of a similar magnitude in the Caco-2 cells, but none of the samples performed significantly better than the others in this cell line.

Though the nanogels were able to achieve a significant silencing efficiency in the RAW 264.7 cells, the percentage is still much less than what has been previously reported of these particles (Forbes and Peppas, 2014), so it is possible that the experimental conditions are not conducive to high transfection and silencing. It is much more likely, however, that the electrostatic interactions between P(MAA-co-NVP), the nanogels, and the siRNA are complicating transfection and silencing. Additionally, as the MTS assay is a measure of cell metabolism rather than cell death, it may not be the ideal assay to evaluate silencing efficiency. It was used in these studies to allow for direct comparison to the previous work by Forbes and Peppas, 2014.

However, a positive aspect of the transfection studies was that the viability of the cells exposed only to the various hydrogel particles (no siRNA) was consistently at or greater than 60%. Toxicity of transfection agents is a continual challenge in delivering siRNA, and fortunately neither the nanogels nor the degradable microgels containing nanogels induced very high levels of toxicity during transfection. Also encouraging was the repeatability of these results in separate studies; though well-to-well variability was high for a few samples, the magnitude of average silencing efficiency and viability was consistent from study to study as well as across cell lines, making the results more credible.

As shown by the data above, nanogels were encapsulated in enzymatically-degradable P(MAA-co-NVP) microgels via a facile crosslinking reaction. Nanogel incorporation and distribution was confirmed by fluorescent spectroscopy and confocal microscopy. Enzyme-specific degradation of the microgels was evaluated by decrease in relative turbidity over time as well as ImageStream flow cytometry; the degradation timescale was relevant to intestinal residence time and the degradation products induced minimal cytotoxic effects at low concentrations.

siRNA was efficiently loaded into the microgel systems due to equilibrium partitioning and charge interactions. The siRNA did experience reduced stability following incubation in the microgel degradation conditions at high trypsin concentrations. Despite the attack by trypsin on the siRNA, a detectable amount was released from the microgel system and escaped degradation, especially in the physiologically relevant buffers. Thus, this microgel system may be used for in vivo applications.

Cellular uptake of nanogels released from degraded microgels was confirmed in RAW 264.7 cells by confocal microscopy. Both ImageStream analysis and confocal microscopy suggest that electrostatic complexation is occurring between the negatively charged degraded P(MAA-co-NVP) and positively charged nanogels, but some of the complexes, free nanogels, or both are internalized by the cells. The transfection efficiencies are consistent across both RAW 264.7 and Caco-2 cell lines and may be increased by optimization of the delivery system and transfection conditions.

The performance of this system may be evaluated in vivo or in conditions more closely resembling in vivo to verify the biodegradability and silencing efficiency; it is possible that a greater portion of the siRNA will remain stable at physiological trypsin concentrations, and competing charged molecules in the intestinal environment may decrease the electrostatic binding via competitive dissociation.

Example 3 siRNA Loaded Peptide Crosslinked Hydrogels

Loading of siRNA into Nanogels
NBD-labeled nanogels were loaded post-synthesis by with either Silencer® Select Negative Control No. 1 siRNA (Life Technologies) or Silencer® Pre-designed siRNA targeting TNF-α (Sense: CGUCGUAGCAAACCACCAA (SEQ ID NO: 52), Life Technologies, Gene ID: 21926). Nanogels were incubated at a concentration of 0.125 mg/ml at room temperature for 30 min in siRNA solutions ranging from 0.25 μM to 4 μM in nuclease-free PBS at pH ~5.5. Nuclease free 10×PBS was prepared by dissolving sodium chloride, potassium chloride, monobasic potassium phosphate, and sodium phosphate dibasic heptahydrate in water, treating with 0.1% v/v diethylpyrocarbonate (DEPC) overnight, and then autoclaving to remove DEPC. Following loading, nanogels were collected by centrifugation at 15,000×g for 10 minutes. Loading of siRNA was evaluated by determining siRNA concentrations left in the supernatant after loading using a Quant-iT™ RiboGreen® RNA Assay Kit. Loading conditions of 0.125 mg/ml nanogels: 1 μM siRNA were used for zeta potential measurements and subsequent transfection studies.

Synthesis of Peptide Crosslinked Hydrogels

Linear P(MAA-co-NVP) was dissolved in a 1:1 (v/v) water:ethanol solution at a concentration of 50 mg/ml. EDC was dissolved in ethanol at a concentration of 50 mg/ml and NHS was dissolved in ethanol at a concentration of 16 mg/ml. The EDC and NHS solutions were added to the polymer solution at a ratio of 6:3:1 polymer:EDC:NHS by weight. The solution was mixed by vortex briefly, and then allowed to react for ~3 min with shaking. Non-siRNA loaded nanogels in a 10 mg/ml solution in ethanol were added at 10 wt % relative to the P(MAA-co-NVP) and the solution was briefly mixed by vortex. The pH was raised to approximately 8 by the addition of 1 N sodium hydroxide (NaOH), and then a volume of 100 mg/ml peptide in ethanol solution was added to achieve a 2:1 weight ratio of polymer: peptide. The mixture was allowed to react overnight with shaking then purified by 3 wash cycles with water and centrifugation at 10,000×g for 5 minutes. These microgels with non-siRNA loaded nanogels were used for initial imaging and degradation studies.

In an analogous reaction scheme, nanogels were first loaded with either control or TNF-α siRNA before encapsulation in the P(MAA-co-NVP) hydrogel. Nanogels at 10 mg/ml in PBS pH 5.5 were mixed with 80 μM siRNA and allowed to electrostatically complex for 30 min. The reaction scheme was then followed as described above, except PBS pH 5.5 was used as the solvent instead of water/ethanol and reaction pH was not adjusted. Reaction conditions at pH 5.5 were chosen because under these conditions the siRNA will remain electrostatically complexed with the nanogels.

Following the washes, the polymer was frozen in liquid nitrogen and lyophilized for at least 24 hours. After lyophilization, the polymer was milled into a fine power by crushing with mortar and pestle. The powder was sifted to sizes of 30-75 μm and less than 30 μm by ultraprecision ASTM sieves (Precision Eforming, Cortland, N.Y.).

Transfection and TNF-α Knockdown

RAW 264.7 macrophages were seeded at a density of 10,000 cells/well in a 96-well plate and allowed to adhere for 24 hr prior to the experiment. Media volumes were maintained at 100 μl/well throughout the experiment. Four different transfection conditions were evaluated. (1) As a positive control, Lipofectamine LTX was incubated with either control or TNF-α siRNA at a concentration of 400 nM siRNA: 1 μl Lipofectamine and allowed to complex for ~10 min prior to dosing cells at 0.1 μl Lipofectamine/ml media. (2) Nanogels were loaded with control or TNF-α siRNA were dosed at a concentration of 0.0125 mg nanogels/ml media. (3) Microgels (30-75 μm) containing nanogels loaded with either control or TNF-α siRNA were degraded at a concentration of 2.5 mg/ml in 0.3 mg/ml trypsin in PBS at 37° C. for 90 minutes. Following degradation, solutions were diluted 10× in OptiMEM®, and cells were dosed at a concentration of 0.25 mg microgels/ml media. (4) Non-degraded microgels (30-75 μm) loaded with TNF-α siRNA nanogels were also dosed to cells at a concentration of 0.25 mg microgels/ml media.

Cells were incubated exposed to these various transfection agents for 24 hr. After 24 hr, media was changed to fresh OptiMEM® containing 100 ng/ml lipopolysaccharide to induce an inflammatory response. After an additional 24 hr, media was collected and assayed for TNF-α content using a Mouse TNF-α Quantikine ELISA kit (R&D Systems, Minneapolis, Minn.). After media collection, cells were lysed using RIPA buffer and total DNA content was assessed using a Quant-iT™ PicoGreen® DNA Assay Kit. Results are reported as pg secreted TNF-α normalized to the total DNA content of that group.

Characterization and siRNA loading of P(DEAEMA-co-tBMA) nanogels is shown in FIGS. 35A-D.

siRNA Transfection and TNF-α Knockdown

Figure 36:
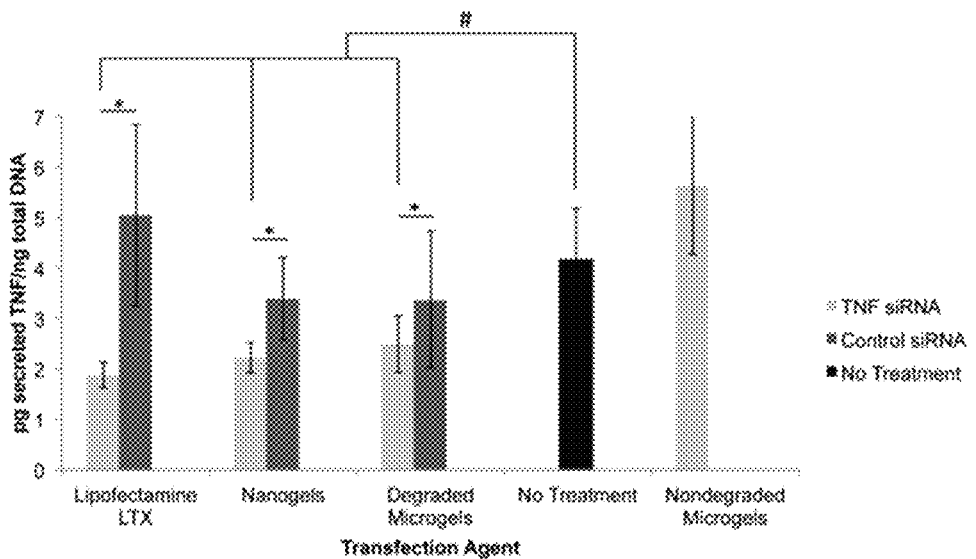
FIG. 36: TNF-α knockdown induced by siRNA carried by Lipofectamine LTX, P(DEAEMA-co-tBMA) nanogels, or degraded microgels containing P(DEAEMA-co-tBMA) nanogels. Secreted TNF-α was significantly decreased in cells incubated with carriers loaded with TNF-α siRNA vs the carrier loaded with a control siRNA (n=4-8, *p<0.05, Student's t-test) and vs no treatment. (n=4-8, #p<0.05, ANOVA). Non-degraded microgels loaded with TNF-α siRNA nanogels did not elicit any knockdown.

RAW 264.7 macrophages were exposed to five different conditions: (1) lipofectamine loaded with control or TNF-α siRNA, (2) nanogels loaded with control or TNF-α siRNA, (3) degraded microgels with control or TNF-α siRNA loaded nanogels, (4) no treatment, and (5) non-degraded microgels with TNF-α siRNA loaded nanogels. The amount of secreted TNF-α protein from cells exposed to these conditions is displayed in FIG. 36.

Lipofectamine, nanogels, and nanogels released from degraded microgels were all capable of transfecting the macrophages, inducing knockdown of TNF-α secretion when TNF-α siRNA was delivered vs. a control siRNA (p<0.05, Student's t-test). Additionally, the TNF-α secretion induced by these three conditions was significantly lower than the macrophages receiving no treatment (p<0.05, ANOVA), further validating the potential for this strategy to be used to mitigate TNF-α production under inflammatory conditions. Cells exposed to non-degraded microgels with encapsulated TNF-α siRNA loaded nanogels did not elicit any knockdown of TNF-α production, indicating the microgel platform must first be degraded before the nanogels can induce siRNA-mediated protein knockdown.

Though the nanogels that were released from the degraded microgels were able to achieve a significant silencing efficiency in the RAW 264.7 cells, they were not as effective as the non-encapsulated nanogels. It is possible that the electrostatic interactions between P(MAA-co-NVP), the nanogels, and the siRNA are complicating transfection and silencing. Additionally, the viability of the cells exposed only to the various hydrogel particles (no siRNA) was consistently at or greater than 80% for concentrations up to 4× higher than those used in transfection studies, leaving the possibility of safely increasing the particle dosage. Toxicity of transfection agents is a continual challenge in delivering siRNA, and fortunately neither the nanogels nor the degradable microgels containing nanogels induced very high levels of toxicity during transfection.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,580,579
U.S. Pat. No. 5,629,001
U.S. Pat. No. 5,641,515
U.S. Pat. No. 5,792,451
U.S. Pat. No. 6,506,559
U.S. Pat. No. 6,573,099
U.S. Pat. No. 6,673,611
U.S. Patent Publication 2002/0168707
U.S. Patent Publication 2003/0051263
U.S. Patent Publication 2003/0055020
U.S. Patent Publication 2003/0159161
U.S. Patent Publication 2004/0019001
U.S. Patent Publication 2004/0064842
U.S. Patent Publication 2004/0265839

Anderson and Shive, *Biodegradation and biocompatibility of pla and plga microspheres*. Adv Drug Deliver Rev, 2012. 64: p. 72-82.

Bae et al., Building vascular networks. Sci Transl Med, 4(160): p. 1-5, 2012.

Bohlen et al., Fluorometric assay of proteins in the nanogram range. Archives of Biochemistry and Biophysics, 155: p. 213-220, 1973.

Bouchie, A., Companies in footrace to deliver rnai. Nat Biotechnol, 30(12): p. 1154-1157, 2012.

Caldorera-Moore and Peppas, Micro- and nanotechnologies for intelligent and responsive biomaterial-based medical systems. Adv Drug Deliver Rev, 61(15): p. 1391-1401, 2009.

Carr and Peppas, Assessment of poly(methacrylic acid-co-n-vinyl pyrrolidone) as a carrier for the oral delivery of therapeutic proteins using caco-2 and ht29-mtx cell lines. J Biomed Mater Res A, 92A: p. 504-512, 2009.

Carr et al., Complexation hydrogels for the oral delivery of growth hormone and salmon calcitonin. Ind Eng Chem Res, 49: p. 11991-11995, 2010.

Cheng et al., Modeling of small-molecule release from crosslinked hydrogel microspheres: Effect of crosslinking and enzymatic degradation of hydrogel matrix. Int J Pharm, 403(1-2): p. 90-95, 2011.

Davis et al., Transit of pharmaceutical dosage forms through the small intestine. Gut, 27: p. 886-892, 1986.

Fattal and Bochot, State of the art and perspectives for the delivery of antisense oligonucleotides and sirna by polymeric nanocarriers. Int. J. Pharm., 364(2): p. 237-248, 2008.

Fischer et al., In vitro cytotoxicity testing of polycations: Influence of polymer structure on cell viability and hemolysis. Biomaterials, 24: p. 1121-1131, 2003.

Forbes and Peppas, Polycationic nanoparticles for sirna delivery: Comparing arget atrp and uv-initiated formulations. ACS Nano, 8: p. 2908-2917, 2014.

Forbes and Peppas, Polymeric nanocarriers for sirna delivery to murine macrophages. Macromol Biosci, 14(8): p. 1096-1105, 2014.

Forbes et al., Polycationic nanoparticles synthesized using arget atrp for drug delivery. Eur J Pharm Biopharm, 84(3): p. 472-478, 2013.

Guvendiren and Burdick, Engineering synthetic hydrogel microenvironments to instruct stem cells. Current Opinion in Biotechnology, 2013. 24(5): p. 841-846, 2013.

Hermanson, G. T., Bioconjugate techniques. San Diego, Calif.: Academic Press, Inc, 1996.

Hickerson et al., Stability study of unmodified sirna and relevance to clinical use. Oligonucleotides, 18: p. 345-354, 2008.

Hoffman, A. S., Environmentally sensitive polymers and hydrogels. MRS Bulletin, 16: p. 42-46, 1991.

Holzapfel et al., How smart do biomaterials need to be? A translational science and clinical point of view. Adv Drug Deliver Rev, 65(4): p. 581-603, 2013.

Hu et al., Enzyme-responsive polymeric assemblies, nanoparticles and hydrogels. Chem Soc Rev, 41(18): p. 5933, 2012.

Hwang et al., Crit. Rev. Ther. Drug Carrier Syst., 15(3):243-284, 1998.

Joshi and Himmelstein, Dynamics of controlled release from bioerodible matrices. J Controlled Release, 15: p. 95-104, 1991.

Kaplan and Bona, Proteases as mitogens: The effect of trypsin and pronase on mouse and human lymphocytes. Experimental Cell Research, 88: p. 388-394, 1974.

Kaplan and Bona, Proteases as mitogens: The effect of trypsin and pronase on mouse and human lymphocytes. Experimental Cell Research, 88: p. 388-394, 1974.

Kavimandan et al., Novel delivery system based on complexation hydrogels as delivery vehicles for insulin-transferrin conjugates. Biomaterials, 27(20): p. 3846-3854, 2006.

Kirschner and Anseth, Hydrogels in healthcare: From static to dynamic material microenvironments. Acta Materialia, 2013. 61(3): p. 931-944, 2013.

Klinger and Landfester, Enzymatic- and light-degradable hybrid nanogels: Crosslinking of polyacrylamide with acrylate-functionalized dextrans containing photocleavable linkers. J Polym Sci, Part A: Polym. Chem, 50(6): p. 1062-1075, 2012.

Klinger and Landfester, Enzymatic- and light-degradable hybrid nanogels: Crosslinking of polyacrylamide with acrylate-functionalized dextrans containing photocleavable linkers. J Polym Sci, Part A: Polym. Chem, 50(6): p. 1062-1075, 2012.

Klinger and Landfester, Photo-sensitive pmma microgels: Light-triggered swelling and degradation. Soft Matter, 7: p. 1426-1440, 2011.

Knipe and Peppas, Multi-responsive hydrogels for drug delivery and tissue engineering applications. Regenerative Biomaterials, 1(1): p. 57-65, 2014(a).

Knipe et al., Multiresponsive polyanionic microgels with inverse ph responsive behavior by encapsulation of polycationic nanogels. J Appl Polym Sci, 2014 (b).

Kolev, T., Solid-state ir-ld spectroscopic and theoretical analysis of arginine-containing peptides. Biopolymers, 83: p. 39-45, 2006.

Kost and Langer, Responsive polymeric delivery systems. Adv Drug Deliver Rev, 64: p. 327-341, 2012.

Lao et al., Modeling of drug release from biodegradable polymer blends. Eur J Pharm Biopharm, 70(3): p. 796-803, 2008.

Lechner, M. D., Influence of mie scattering on nanoparticles with different particle sizes and shapes: Photometry and analytical ultracentrifugation with absorption optics. Journal of the Serbian Chemical Society, 70: p. 361-369, 2005.

Liang et al., Endocytic ph-triggered degradation of nanoengineered multilayer capsules. Adv Mater, 26(12): p. 1901-1905, 2014.

Liechty and Peppas, Expert opinion: Responsive polymer nanoparticles in cancer therapy. Eur J Pharm Biopharm, 80(2): p. 241-246, 2012.

Lin et al., Extracellular delivery of modified oligonucleotide and superparamagnetic iron oxide nanoparticles from a degradable hydrogel triggered by tumor acidosis. Biomaterials, 34(17): p. 4387-4393, 2013.

Lopac et al., Effect of polymer chemistry and fabrication method on protein release and stability from polyanhydride microspheres. Journal of Biomedical Materials Research Part B: Applied Biomaterials, 91B(2): p. 938-947, 2009.

Lowman et al., Oral delivery of insulin using ph-responsive complexation gels. J Pharm Sci, 88: p. 933-937, 1999.

Mathiowitz et al., Nature, 386(6623):410-414, 1997.

Moret et al., Stability of pei-DNA and dotap-DNA complexes: Effect of alkaline ph, heparin and serum. J Controlled Release, 76(169-181), 2001.

Nakamura et al., Oral insulin delivery using p(maa-g-eg) hydrogels: Effects of network morphology on insulin delivery characteristics. J Controlled Release, 95(3): p. 589-599, 2004.

Olsen, J. V., Trypsin cleaves exclusively c-terminal to arginine and lysine residues. Mol Cell Proteomics, 3(6): p. 608-614, 2004.

Pace, J., Lxviii. The inactivation of trypsin by heat. Biochemical Journal, 24: p. i3, 1930.

Peppas and Kavimandan, Nanoscale analysis of protein and peptide absorption: Insulin absorption using complexation and ph-sensitive hydrogels as delivery vehicles. Eur J Pharm Sci, 29(3-4): p. 183-197, 2006(a).

Peppas et al., Hydrogels in biology and medicine: From molecular principles to bionanotechnology. Adv Mater, 18(11): p. 1345-1360(b).

Peppas et al., Hydrogels in pharmaceutical formulations. Eur J Pharm Biopharm, 50: p. 27-46, 2000.

Pharmacopeia, T.U.S., United states pharmacopeia 29 national formulary 24, in Reagents: Test Solutions. 2006.

Pharmacopeia, T.U.S., United states pharmacopeia 29 national formulary 24, in Reagents: Test Solutions. 2006.

Phelps et al., Bioartificial matrices for therapeutic vascularization. P Natl Acad Sci USA, 107(8): p. 3323-3328, 2009.

Qiu and Park, Environment-sensitive hydrogels for drug delivery. Adv Drug Deliver Rev, 53(3): p. 321-339, 2001.

Qiu et al., Temperature-induced phase transition of well-defined cyclic poly(n-isopropylacrylamide)s in aqueous solution. Macromolecules, 40: p. 7069-7071, 2007.

Rice et al., Exogenously triggered, enzymatic degradation of photopolymerized hydrogels with polycaprolactone subunits: Experimental observation and modeling of mass loss behavior. Biomacromolecules, 7: p. 1968-1975, 2006.

Schiffelers et al., Pharmaceutical prospects for ma interference. Pharm Res, 21: p. 1-7, 2003.

Schwert and Takenaka, A spectrophotometric determination of trypsin and chymotrypsin. Biochimica Et Biophysica Acta, 16: p. 570-575, 1955.

Thombre and Himmelstein, A simultaneous transport-reaction model for controlled drug delivery from catalyzed bioerodible polymer matrices. AIChE Journal, 31: p. 159-766, 1985.

Tones et al., Amphiphilic polyanhydrides for protein stabilization and release. Biomaterials, 28(1): p. 108-116, 2007.

Tones-Lugo and Peppas, Molecular design and in vitro studies of novel ph-sensitive hydrogels for the oral delivery of calcitonin. Macromolecules, 32: p. 6646-6651, 1999.

Tones-Lugo and Peppas, Preparation and characterization of p(maa-g-eg) nanospheres for protein delivery applications. J Nanopart Res, 4: p. 73-81, 2002.

Unanue, E. R., Antigen-presenting function of the macrophage. Annual Review of Immunology, 2: p. 395-428, 1984.

Unanue, E. R., Antigen-presenting function of the macrophage. Annual Review of Immunology, 2: p. 395-428, 1984.

Vlieghe et al., Synthetic therapeutic peptides: Science and market. Drug Discovery Today, 15(1-2): p. 40-56, 2010.

Whitehead et al., Knocking down barriers: Advances in sirna delivery. Nat. Rev. Drug Discovery, 8(2): p. 129-138, 2009.

Wong et al., Synthetically designed peptide-based biomaterials with stimuli-responsive and membrane-active properties for biomedical applications. Journal of Materials Chemistry B, 2(6): p. 595, 2014.

Xu et al., Synthesis of well-defined cyclic poly(n-isopropylacrylamide) via click chemistry and its unique thermal phase transition behavior. Macromolecules, 40: p. 9103-9110, 2007.

Yamagata et al., Characterization of insulin protection properties of complexation hydrogels in gastric and intestinal enzyme fluids. J Controlled Release, 112(3): p. 343-349, 2006.

Yamagata et al., Characterization of insulin protection properties of complexation hydrogels in gastric and intestinal enzyme fluids. J Controlled Release, 112(3): p. 343-349, 2006.

Yanes et al., Enzymatic measurements for the detection of trypsin and carboxypeptidase a inhibitory activity. 2007.

Yanes et al., Enzymatic measurements for the detection of trypsin and carboxypeptidase a inhibitory activity. 2007.

Zelphati et al., Mechanism of oligonucleotide release from cationic liposomes. P Natl Acad Sci USA, 93: p. 11493-11498, 1996.

What is claimed is:

1. A hydrogel composed of a polymer, wherein the polymer comprises a poly(methacrylic acid-co-N-vinylpyrrolidone) (P(MAA-co-NVP)) copolymer that is crosslinked with an enzymatically cleavable peptide linker, wherein the peptide linker consists of 3-25 amino acid residues and contains at least one lysine amino acid, wherein the hydrogel further comprises a therapeutic agent.

2. The hydrogel of claim 1, wherein the peptide linker is cleavable by a serine protease, carboxypeptidase, or aminopeptidase.

3. The hydrogel of claim 2, wherein the serine protease is trypsin, chymotrypsin, or elastase.

4. The hydrogel of claim 3, wherein the peptide linker is cleavable by trypsin, wherein the trypsin is trypsin 1, trypsin 2, or mesotrypsin.

5. The hydrogel of claim 1, wherein the peptide is 4-20 amino acid residues in length.

6. The hydrogel of claim 5, wherein the peptide is 5-15 amino acid residues in length.

7. The hydrogel of claim 6, wherein the peptide is 5-10 amino acid residues in length.

8. The hydrogel of claim 7, wherein the peptide comprises or consists of GRRRGK (SEQ ID NO: 1).

9. The hydrogel of claim 8, wherein the peptide comprises the structure:

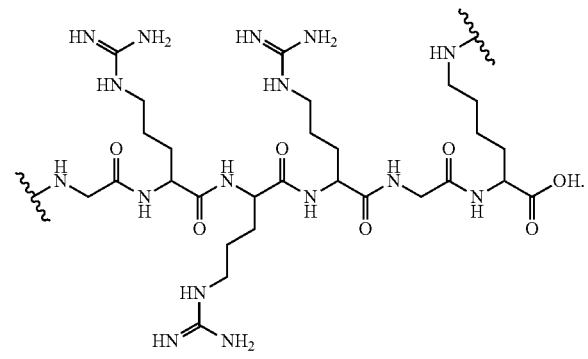 [SMILES: *NCCCCC(NC(=O)CNC(=O)C(CCCNC(=N)N)NC(=O)C(CCCNC(=N)N)NC(=O)C(CCCNC(=N)N)NC(=O)CN*)C(=O)O]

10. The hydrogel of claim 8, wherein the polymer comprises the structure:

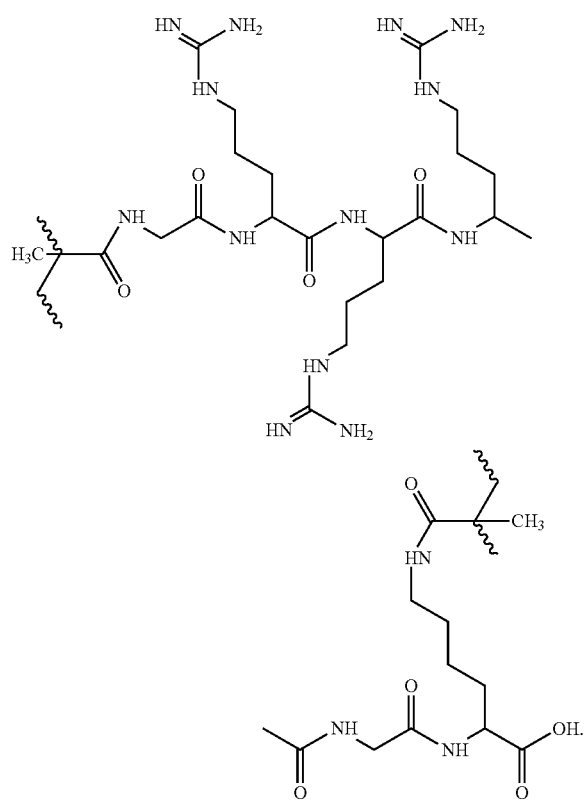

11. The hydrogel of claim 1, wherein the polymer has been crosslinked with the peptide through the use of a coupling reagent.

12. The hydrogel of claim 11, wherein the coupling reagent is a carbodiimide.

13. The hydrogel of claim 11, wherein the polymer has been crosslinked with the peptide via an EDC-NHS reaction.

14. The hydrogel of claim 1, wherein the hydrogel further comprises a polycationic nanoparticle.

15. The hydrogel of claim 14, wherein the polycationic nanoparticle is substantially comprised within the hydrogel.

16. The hydrogel of claim 14, wherein the polycationic nanoparticle comprises or consists of poly(2-methoxyethylacrylate) (PMEA), poly(2-(diethylaminoethyl) methacrylate) (PDEAEMA), chitosan, poly(ethyleneimine) (PEI), poly(amidoamine) (PAMAM), poly(dimethylaminopropyl methacrylate) (PDMAPMA), poly(2-aminoethyl methacrylate) (PAEMA), or poly(2-(dimethylaminoethyl) methacrylate) (PDMAEMA).

17. The hydrogel of claim 1, wherein the therapeutic agent is a therapeutic protein.

18. The hydrogel of claim 1, wherein the therapeutic agent is a nucleic acid.

19. The hydrogel of claim 18, wherein the nucleic acid is a small interfering RNA (siRNA), a micro RNA (miRNA), a short hairpin RNA (shRNA), or an antisense oligonucleotide.

20. The hydrogel of claim 19, wherein the nucleic acid is an siRNA.

21. A method of treating a disease comprising administering the hydrogel of claim 1 to a mammalian subject in need of such treatment.

22. The method of claim 21, wherein the administration is oral.

* * * * *

```
                        SEQUENCE LISTING

<160> NUMBER OF SEQ ID NOS: 52

<210> SEQ ID NO 1
<211> LENGTH: 6
<212> TYPE: PRT
<213> ORGANISM: Artificial sequence
<220> FEATURE:
<223> OTHER INFORMATION: Synthetic peptide

<400> SEQUENCE: 1

Gly Arg Arg Arg Gly Lys
1               5

<210> SEQ ID NO 2
<211> LENGTH: 4
<212> TYPE: PRT
<213> ORGANISM: Artificial sequence
<220> FEATURE:
<223> OTHER INFORMATION: Synthetic peptide

<400> SEQUENCE: 2

Gly Arg Gly Lys
1

<210> SEQ ID NO 3
<211> LENGTH: 4
<212> TYPE: PRT
<213> ORGANISM: Artificial sequence
<220> FEATURE:
<223> OTHER INFORMATION: Synthetic peptide

<400> SEQUENCE: 3

Gly Lys Gly Lys
1

<210> SEQ ID NO 4
<211> LENGTH: 5
<212> TYPE: PRT
<213> ORGANISM: Artificial sequence
<220> FEATURE:
<223> OTHER INFORMATION: Synthetic peptide

<400> SEQUENCE: 4

Gly Arg Arg Gly Lys
1               5

<210> SEQ ID NO 5
<211> LENGTH: 5
<212> TYPE: PRT
<213> ORGANISM: Artificial sequence
<220> FEATURE:
<223> OTHER INFORMATION: Synthetic peptide

<400> SEQUENCE: 5

Gly Arg Lys Gly Lys
1               5

<210> SEQ ID NO 6
```

```
<211> LENGTH: 5
<212> TYPE: PRT
<213> ORGANISM: Artificial sequence
<220> FEATURE:
<223> OTHER INFORMATION: Synthetic peptide

<400> SEQUENCE: 6

Gly Lys Lys Gly Lys
1               5

<210> SEQ ID NO 7
<211> LENGTH: 6
<212> TYPE: PRT
<213> ORGANISM: Artificial sequence
<220> FEATURE:
<223> OTHER INFORMATION: Synthetic peptide

<400> SEQUENCE: 7

Gly Lys Arg Arg Gly Lys
1               5

<210> SEQ ID NO 8
<211> LENGTH: 6
<212> TYPE: PRT
<213> ORGANISM: Artificial sequence
<220> FEATURE:
<223> OTHER INFORMATION: Synthetic peptide

<400> SEQUENCE: 8

Gly Lys Lys Arg Gly Lys
1               5

<210> SEQ ID NO 9
<211> LENGTH: 6
<212> TYPE: PRT
<213> ORGANISM: Artificial sequence
<220> FEATURE:
<223> OTHER INFORMATION: Synthetic peptide

<400> SEQUENCE: 9

Gly Lys Lys Lys Gly Lys
1               5

<210> SEQ ID NO 10
<211> LENGTH: 6
<212> TYPE: PRT
<213> ORGANISM: Artificial sequence
<220> FEATURE:
<223> OTHER INFORMATION: Synthetic peptide

<400> SEQUENCE: 10

Gly Arg Gly Arg Gly Lys
1               5

<210> SEQ ID NO 11
<211> LENGTH: 6
<212> TYPE: PRT
<213> ORGANISM: Artificial sequence
<220> FEATURE:
<223> OTHER INFORMATION: Synthetic peptide

<400> SEQUENCE: 11

Gly Lys Gly Lys Gly Lys
1               5

<210> SEQ ID NO 12
<211> LENGTH: 7
```

```
<212> TYPE: PRT
<213> ORGANISM: Artificial sequence
<220> FEATURE:
<223> OTHER INFORMATION: Synthetic peptide

<400> SEQUENCE: 12

Gly Arg Arg Arg Arg Gly Lys
1               5

<210> SEQ ID NO 13
<211> LENGTH: 7
<212> TYPE: PRT
<213> ORGANISM: Artificial sequence
<220> FEATURE:
<223> OTHER INFORMATION: Synthetic peptide

<400> SEQUENCE: 13

Gly Lys Arg Arg Arg Gly Lys
1               5

<210> SEQ ID NO 14
<211> LENGTH: 7
<212> TYPE: PRT
<213> ORGANISM: Artificial sequence
<220> FEATURE:
<223> OTHER INFORMATION: Synthetic peptide

<400> SEQUENCE: 14

Gly Arg Lys Arg Arg Gly Lys
1               5

<210> SEQ ID NO 15
<211> LENGTH: 7
<212> TYPE: PRT
<213> ORGANISM: Artificial sequence
<220> FEATURE:
<223> OTHER INFORMATION: Synthetic peptide

<400> SEQUENCE: 15

Gly Arg Arg Lys Arg Gly Lys
1               5

<210> SEQ ID NO 16
<211> LENGTH: 7
<212> TYPE: PRT
<213> ORGANISM: Artificial sequence
<220> FEATURE:
<223> OTHER INFORMATION: Synthetic peptide

<400> SEQUENCE: 16

Gly Arg Arg Arg Lys Gly Lys
1               5

<210> SEQ ID NO 17
<211> LENGTH: 7
<212> TYPE: PRT
<213> ORGANISM: Artificial sequence
<220> FEATURE:
<223> OTHER INFORMATION: Synthetic peptide

<400> SEQUENCE: 17

Gly Lys Lys Arg Arg Gly Lys
1               5

<210> SEQ ID NO 18
<211> LENGTH: 7
<212> TYPE: PRT
```

```
<213> ORGANISM: Artificial sequence
<220> FEATURE:
<223> OTHER INFORMATION: Synthetic peptide

<400> SEQUENCE: 18

Gly Arg Lys Lys Arg Gly Lys
1               5

<210> SEQ ID NO 19
<211> LENGTH: 7
<212> TYPE: PRT
<213> ORGANISM: Artificial sequence
<220> FEATURE:
<223> OTHER INFORMATION: Synthetic peptide

<400> SEQUENCE: 19

Gly Arg Arg Lys Lys Gly Lys
1               5

<210> SEQ ID NO 20
<211> LENGTH: 7
<212> TYPE: PRT
<213> ORGANISM: Artificial sequence
<220> FEATURE:
<223> OTHER INFORMATION: Synthetic peptide

<400> SEQUENCE: 20

Gly Arg Lys Arg Lys Gly Lys
1               5

<210> SEQ ID NO 21
<211> LENGTH: 7
<212> TYPE: PRT
<213> ORGANISM: Artificial sequence
<220> FEATURE:
<223> OTHER INFORMATION: Synthetic peptide

<400> SEQUENCE: 21

Gly Lys Arg Lys Arg Gly Lys
1               5

<210> SEQ ID NO 22
<211> LENGTH: 7
<212> TYPE: PRT
<213> ORGANISM: Artificial sequence
<220> FEATURE:
<223> OTHER INFORMATION: Synthetic peptide

<400> SEQUENCE: 22

Gly Gly Arg Arg Arg Gly Lys
1               5

<210> SEQ ID NO 23
<211> LENGTH: 7
<212> TYPE: PRT
<213> ORGANISM: Artificial sequence
<220> FEATURE:
<223> OTHER INFORMATION: Synthetic peptide

<400> SEQUENCE: 23

Gly Arg Gly Arg Arg Gly Lys
1               5

<210> SEQ ID NO 24
<211> LENGTH: 7
<212> TYPE: PRT
<213> ORGANISM: Artificial sequence
```

```
<220> FEATURE:
<223> OTHER INFORMATION: Synthetic peptide

<400> SEQUENCE: 24

Gly Arg Arg Gly Arg Gly Lys
1               5

<210> SEQ ID NO 25
<211> LENGTH: 7
<212> TYPE: PRT
<213> ORGANISM: Artificial sequence
<220> FEATURE:
<223> OTHER INFORMATION: Synthetic peptide

<400> SEQUENCE: 25

Gly Arg Arg Arg Gly Gly Lys
1               5

<210> SEQ ID NO 26
<211> LENGTH: 7
<212> TYPE: PRT
<213> ORGANISM: Artificial sequence
<220> FEATURE:
<223> OTHER INFORMATION: Synthetic peptide

<400> SEQUENCE: 26

Gly Gly Gly Arg Arg Gly Lys
1               5

<210> SEQ ID NO 27
<211> LENGTH: 7
<212> TYPE: PRT
<213> ORGANISM: Artificial sequence
<220> FEATURE:
<223> OTHER INFORMATION: Synthetic peptide

<400> SEQUENCE: 27

Gly Arg Gly Gly Arg Gly Lys
1               5

<210> SEQ ID NO 28
<211> LENGTH: 7
<212> TYPE: PRT
<213> ORGANISM: Artificial sequence
<220> FEATURE:
<223> OTHER INFORMATION: Synthetic peptide

<400> SEQUENCE: 28

Gly Arg Arg Gly Gly Gly Lys
1               5

<210> SEQ ID NO 29
<211> LENGTH: 7
<212> TYPE: PRT
<213> ORGANISM: Artificial sequence
<220> FEATURE:
<223> OTHER INFORMATION: Synthetic peptide

<400> SEQUENCE: 29

Gly Arg Gly Arg Gly Gly Lys
1               5

<210> SEQ ID NO 30
<211> LENGTH: 7
<212> TYPE: PRT
<213> ORGANISM: Artificial sequence
<220> FEATURE:
```

```
<223> OTHER INFORMATION: Synthetic peptide

<400> SEQUENCE: 30

Gly Gly Arg Gly Arg Gly Lys
1               5

<210> SEQ ID NO 31
<211> LENGTH: 7
<212> TYPE: PRT
<213> ORGANISM: Artificial sequence
<220> FEATURE:
<223> OTHER INFORMATION: Synthetic peptide

<400> SEQUENCE: 31

Gly Lys Gly Gly Gly Gly Lys
1               5

<210> SEQ ID NO 32
<211> LENGTH: 7
<212> TYPE: PRT
<213> ORGANISM: Artificial sequence
<220> FEATURE:
<223> OTHER INFORMATION: Synthetic peptide

<400> SEQUENCE: 32

Gly Gly Lys Gly Gly Gly Lys
1               5

<210> SEQ ID NO 33
<211> LENGTH: 7
<212> TYPE: PRT
<213> ORGANISM: Artificial sequence
<220> FEATURE:
<223> OTHER INFORMATION: Synthetic peptide

<400> SEQUENCE: 33

Gly Gly Gly Lys Gly Gly Lys
1               5

<210> SEQ ID NO 34
<211> LENGTH: 7
<212> TYPE: PRT
<213> ORGANISM: Artificial sequence
<220> FEATURE:
<223> OTHER INFORMATION: Synthetic peptide

<400> SEQUENCE: 34

Gly Gly Gly Gly Lys Gly Lys
1               5

<210> SEQ ID NO 35
<211> LENGTH: 7
<212> TYPE: PRT
<213> ORGANISM: Artificial sequence
<220> FEATURE:
<223> OTHER INFORMATION: Synthetic peptide

<400> SEQUENCE: 35

Gly Lys Lys Gly Gly Gly Lys
1               5

<210> SEQ ID NO 36
<211> LENGTH: 7
<212> TYPE: PRT
<213> ORGANISM: Artificial sequence
<220> FEATURE:
<223> OTHER INFORMATION: Synthetic peptide
```

```
<400> SEQUENCE: 36

Gly Gly Lys Lys Gly Gly Lys
1               5

<210> SEQ ID NO 37
<211> LENGTH: 7
<212> TYPE: PRT
<213> ORGANISM: Artificial sequence
<220> FEATURE:
<223> OTHER INFORMATION: Synthetic peptide

<400> SEQUENCE: 37

Gly Gly Gly Lys Lys Gly Lys
1               5

<210> SEQ ID NO 38
<211> LENGTH: 7
<212> TYPE: PRT
<213> ORGANISM: Artificial sequence
<220> FEATURE:
<223> OTHER INFORMATION: Synthetic peptide

<400> SEQUENCE: 38

Gly Gly Lys Gly Lys Gly Lys
1               5

<210> SEQ ID NO 39
<211> LENGTH: 7
<212> TYPE: PRT
<213> ORGANISM: Artificial sequence
<220> FEATURE:
<223> OTHER INFORMATION: Synthetic peptide

<400> SEQUENCE: 39

Gly Lys Gly Lys Gly Gly Lys
1               5

<210> SEQ ID NO 40
<211> LENGTH: 7
<212> TYPE: PRT
<213> ORGANISM: Artificial sequence
<220> FEATURE:
<223> OTHER INFORMATION: Synthetic peptide

<400> SEQUENCE: 40

Gly Arg Lys Gly Gly Gly Lys
1               5

<210> SEQ ID NO 41
<211> LENGTH: 7
<212> TYPE: PRT
<213> ORGANISM: Artificial sequence
<220> FEATURE:
<223> OTHER INFORMATION: Synthetic peptide

<400> SEQUENCE: 41

Gly Gly Arg Lys Gly Gly Lys
1               5

<210> SEQ ID NO 42
<211> LENGTH: 7
<212> TYPE: PRT
<213> ORGANISM: Artificial sequence
<220> FEATURE:
<223> OTHER INFORMATION: Synthetic peptide
```

```
<400> SEQUENCE: 42

Gly Gly Gly Arg Lys Gly Lys
1               5

<210> SEQ ID NO 43
<211> LENGTH: 7
<212> TYPE: PRT
<213> ORGANISM: Artificial sequence
<220> FEATURE:
<223> OTHER INFORMATION: Synthetic peptide

<400> SEQUENCE: 43

Gly Gly Arg Gly Lys Gly Lys
1               5

<210> SEQ ID NO 44
<211> LENGTH: 7
<212> TYPE: PRT
<213> ORGANISM: Artificial sequence
<220> FEATURE:
<223> OTHER INFORMATION: Synthetic peptide

<400> SEQUENCE: 44

Gly Arg Gly Lys Gly Gly Lys
1               5

<210> SEQ ID NO 45
<211> LENGTH: 7
<212> TYPE: PRT
<213> ORGANISM: Artificial sequence
<220> FEATURE:
<223> OTHER INFORMATION: Synthetic peptide

<400> SEQUENCE: 45

Gly Lys Arg Gly Gly Gly Lys
1               5

<210> SEQ ID NO 46
<211> LENGTH: 7
<212> TYPE: PRT
<213> ORGANISM: Artificial sequence
<220> FEATURE:
<223> OTHER INFORMATION: Synthetic peptide

<400> SEQUENCE: 46

Gly Gly Lys Arg Gly Gly Lys
1               5

<210> SEQ ID NO 47
<211> LENGTH: 7
<212> TYPE: PRT
<213> ORGANISM: Artificial sequence
<220> FEATURE:
<223> OTHER INFORMATION: Synthetic peptide

<400> SEQUENCE: 47

Gly Gly Gly Lys Arg Gly Lys
1               5

<210> SEQ ID NO 48
<211> LENGTH: 7
<212> TYPE: PRT
<213> ORGANISM: Artificial sequence
<220> FEATURE:
<223> OTHER INFORMATION: Synthetic peptide

<400> SEQUENCE: 48
```

```
Gly Gly Lys Gly Arg Gly Lys
1               5

<210> SEQ ID NO 49
<211> LENGTH: 7
<212> TYPE: PRT
<213> ORGANISM: Artificial sequence
<220> FEATURE:
<223> OTHER INFORMATION: Synthetic peptide

<400> SEQUENCE: 49

Gly Lys Gly Arg Gly Gly Lys
1               5

<210> SEQ ID NO 50
<211> LENGTH: 7
<212> TYPE: PRT
<213> ORGANISM: Artificial sequence
<220> FEATURE:
<223> OTHER INFORMATION: Synthetic peptide

<400> SEQUENCE: 50

Gly Lys Lys Lys Lys Gly Lys
1               5

<210> SEQ ID NO 51
<211> LENGTH: 21
<212> TYPE: RNA
<213> ORGANISM: Artificial sequence
<220> FEATURE:
<223> OTHER INFORMATION: Synthetic oligoribonucleotide

<400> SEQUENCE: 51
uaaggcuaug aagagauacu u                                          21

<210> SEQ ID NO 52
<211> LENGTH: 19
<212> TYPE: RNA
<213> ORGANISM: Artificial sequence
<220> FEATURE:
<223> OTHER INFORMATION: Synthetic oligoribonucleotide

<400> SEQUENCE: 52
cgucguagca aaccaccaa                                             19
```